(12) United States Patent
Heasman et al.

(10) Patent No.: US 11,590,343 B2
(45) Date of Patent: Feb. 28, 2023

(54) ELECTRICAL TECHNIQUES FOR BIOMARKER DETECTION IN A COCHLEA

(71) Applicant: COCHLEAR LIMITED, Macquarie University (AU)

(72) Inventors: John Michael Heasman, Macquarie University (AU); Peter Gibson, Macquarie University (AU); Riaan Rottier, Macquarie University (AU); Mary-Beth Brinson, Macquarie University (AU); Stephen John O'Leary, Macquarie University (AU); Christofer William Bester, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 154 days.

(21) Appl. No.: 17/042,607

(22) PCT Filed: Mar. 25, 2019

(86) PCT No.: PCT/IB2019/052414
§ 371 (c)(1),
(2) Date: Sep. 28, 2020

(87) PCT Pub. No.: WO2019/186373
PCT Pub. Date: Oct. 3, 2019

(65) Prior Publication Data
US 2021/0093852 A1    Apr. 1, 2021

Related U.S. Application Data

(60) Provisional application No. 62/647,896, filed on Mar. 26, 2018.

(51) Int. Cl.
*A61N 1/05* (2006.01)
*A61N 1/36* (2006.01)
(Continued)

(52) U.S. Cl.
CPC .............. *A61N 1/0541* (2013.01); *A61B 5/24* (2021.01); *A61B 5/6815* (2013.01); *A61N 1/36038* (2017.08)

(58) Field of Classification Search
CPC .... A61N 1/05; A61N 1/0541; A61N 1/36038; A61B 5/24; A61B 5/6815
See application file for complete search history.

(56) References Cited

U.S. PATENT DOCUMENTS

2011/0087085 A1* 4/2011 Tsampazis ........... A61B 5/0538
600/379
2011/0196245 A1   8/2011 Poupko et al.
(Continued)

FOREIGN PATENT DOCUMENTS

KR    20080015212 A    2/2008
KR    20160149878 A    12/2016

OTHER PUBLICATIONS

International Search Report & Written Opinion for PCT/IB2019/052414, dated Aug. 2, 2019.
(Continued)

*Primary Examiner* — Christopher A Flory
(74) *Attorney, Agent, or Firm* — Pilloff Passino & Cosenza LLP; Martin J. Cosenza

(57) ABSTRACT

A method, including energizing one or more electrodes of a cochlear electrode array to induce a current flow in the cochlea at a plurality of temporal locations, measuring one or more electrical properties at one or more locations in the cochlea resulting from the induced current flow at the plurality of different temporal locations and determining whether or not trauma has occurred based on a change between the measured electrical properties from the first temporal location to the second temporal location.

24 Claims, 36 Drawing Sheets

(51) Int. Cl.
   *A61B 5/24*   (2021.01)
   *A61B 5/00*   (2006.01)

(56)         References Cited

U.S. PATENT DOCUMENTS

2015/0289787 A1    10/2015  Buchman et al.
2015/0320550 A1    11/2015  Downing et al.
2016/0367195 A1    12/2016  Park et al.
2019/0030323 A1*   1/2019   Koka .................. A61N 1/0541
2020/0171301 A1*   6/2020   Koka ....................... A61N 1/08
2020/0206507 A1*   7/2020   Koka .................. A61N 1/0541
2020/0375667 A1*  12/2020   Polak .................. A61N 1/0541

OTHER PUBLICATIONS

Jan Kiefer et al., "Representation of acoustic signals in the human cochlea in presence of a cochlear implant electrode," Hearing Research, Nov. 2006, pp. 36-43, vol. 221.
Alicia M. Quesnel et al., "Delayed loss of hearing after hearing preservation cochlear implantation: Human temporal bone pathology and implications for etiology," Hearing Research, Mar. 2016, pp. 1-10.
Kyeung A. Ryu et al. , "Intracochlear bleeding enhances cochlear fibrosis and ossification: An animal study," PLoS ONE, Aug. 2015, pp. 1-13, vol. 10, No. 8.
H. Smeds et al., "Endolymphatic hydrops is prevalent in the first weeks following cochlear implantation," Hearing Research, Sep. 2015, pp. 48-57, vol. 327.

* cited by examiner

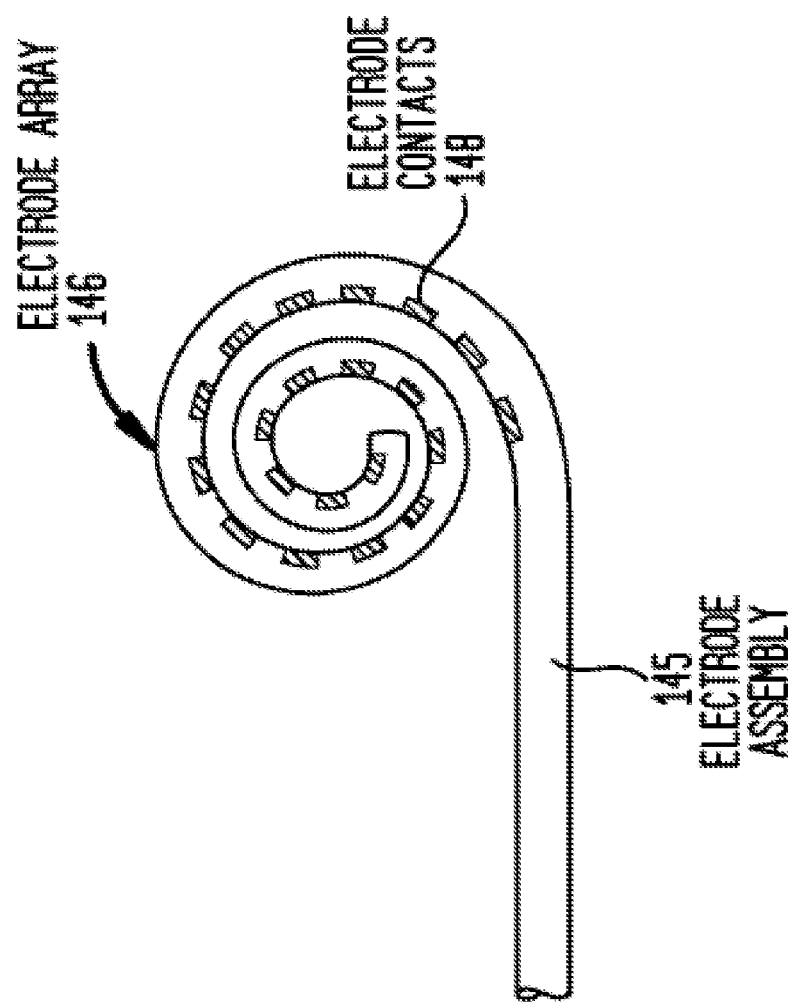

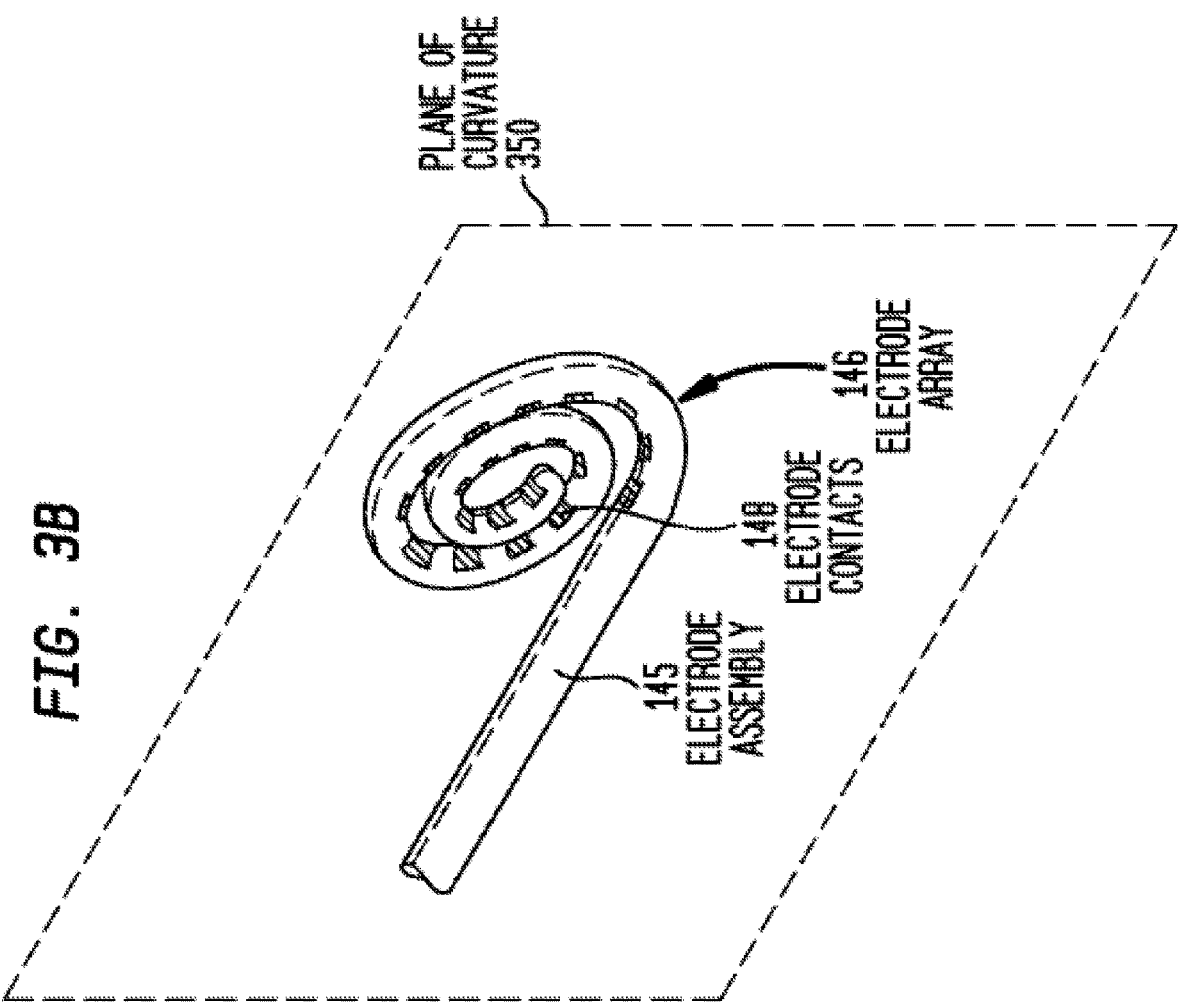

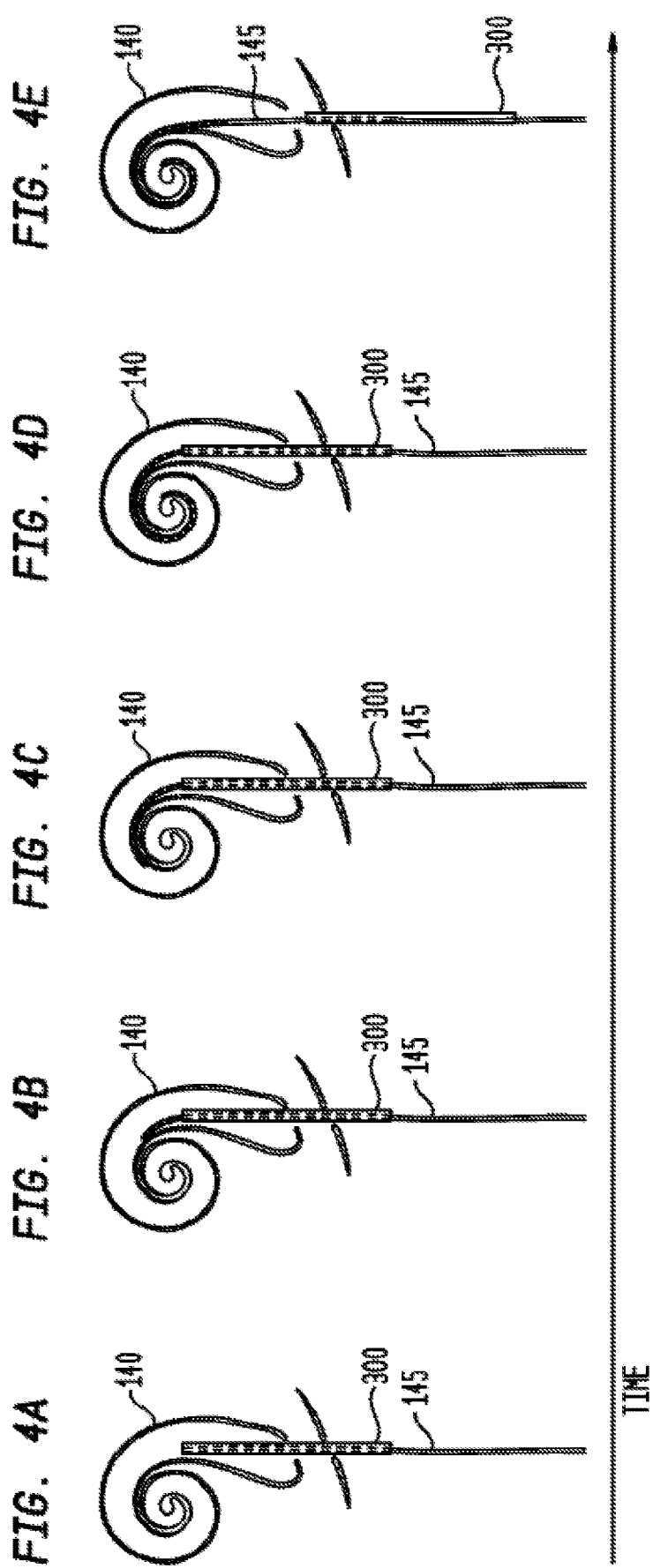

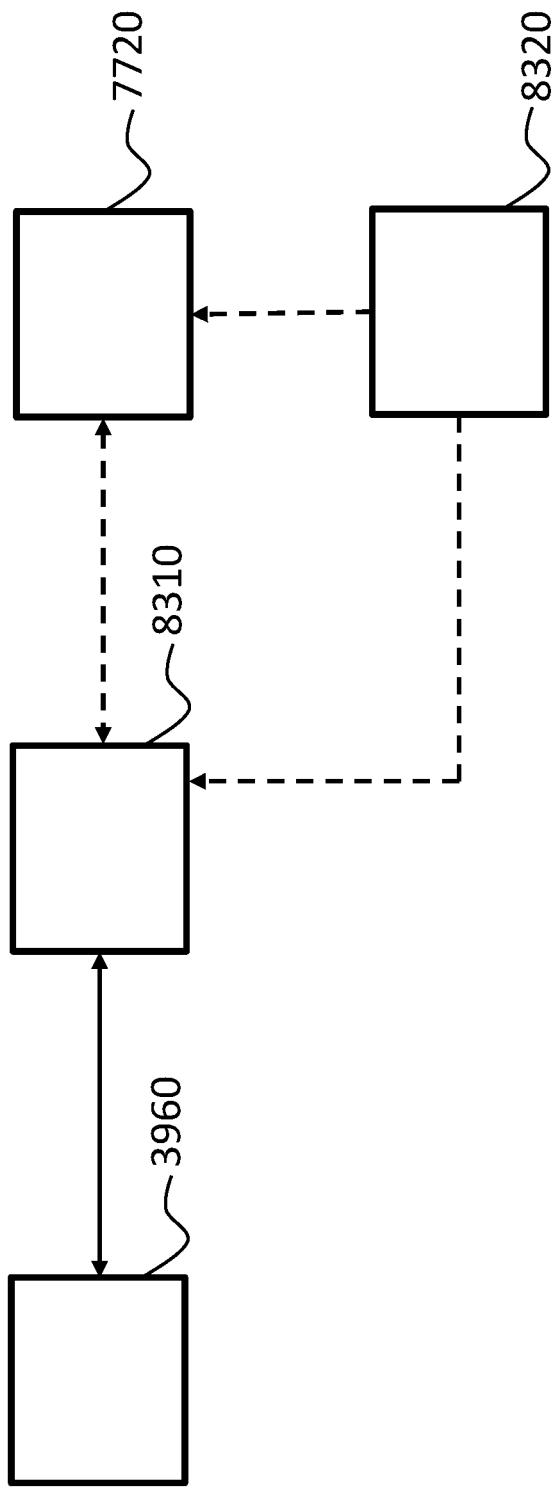

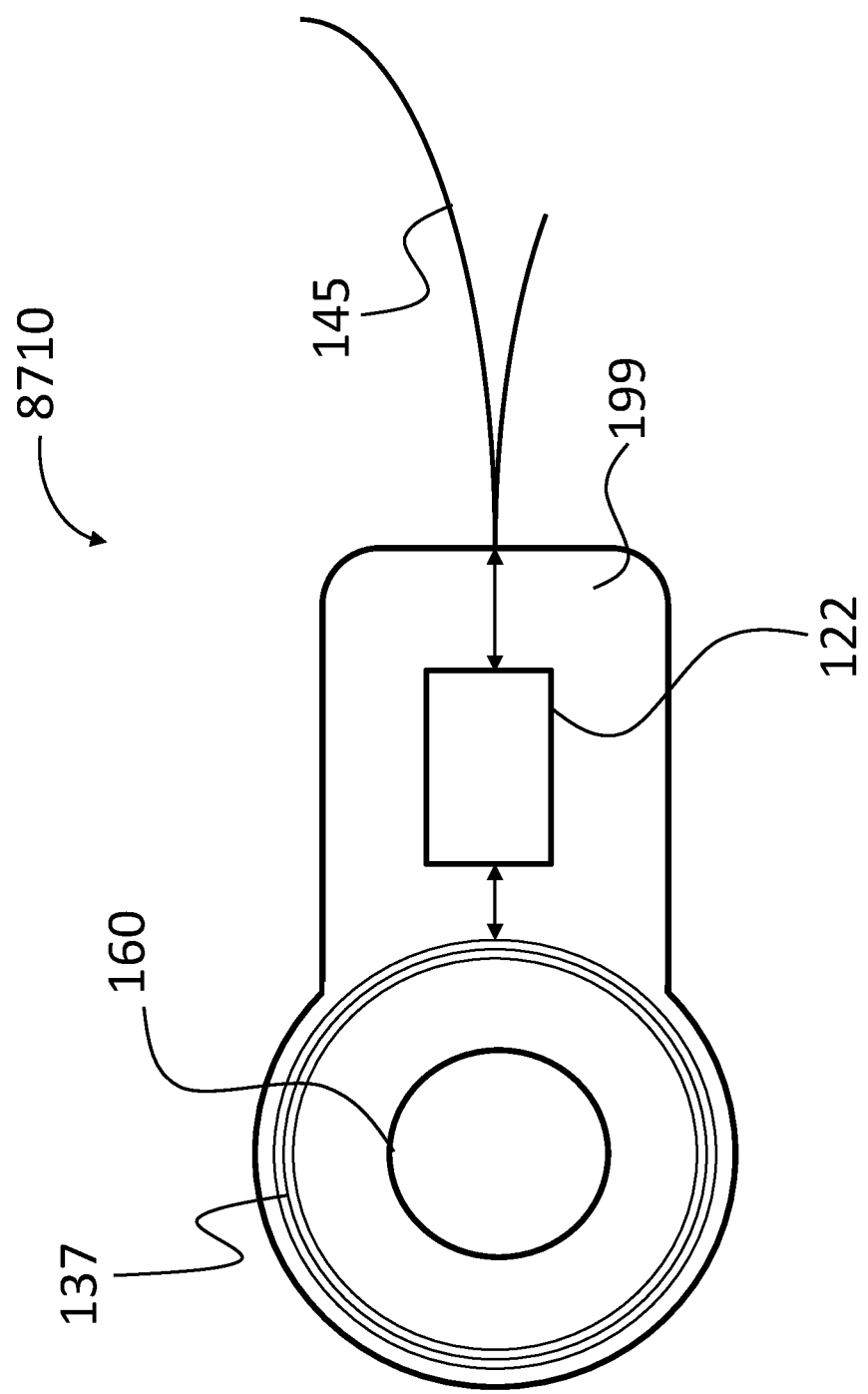

ELECTRICAL TECHNIQUES FOR BIOMARKER DETECTION IN A COCHLEA

BACKGROUND

This application claims priority to U.S. Provisional Application No. 62/647,896, entitled ELECTRICAL TECHNIQUES FOR BIOMARKER DETECTION IN A COCHLEA, filed on Mar. 26, 2018, naming John Michael Heasman of East Melbourne, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. A hearing prosthesis can be a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting.

SUMMARY

In accordance with an exemplary embodiment, there is a method, comprising energizing one or more electrodes of a cochlear electrode array to induce a current flow in the cochlea at a plurality of temporal locations, measuring one or more electrical properties at one or more locations in the cochlea resulting from the induced current flow at the plurality of different temporal locations, and determining whether or not trauma has occurred based on a change between the measured electrical properties from the first temporal location to the second temporal location.

In accordance with an exemplary embodiment, there is a method, comprising causing current to flow from a first electrode of an intra-cochlea electrode array to a second electrode of the intra-cochlea electrode array at a plurality of temporal locations, measuring, at a third electrode and a fourth electrode of the intra-cochlea electrode array, respective voltages induced by the flowing current at the plurality of temporal locations, determining that a change between the voltage measurements at the third electrode and the fourth electrode has occurred between the temporal locations, determining a time period between the temporal locations, and determining whether or not a phenomenon has occurred within the cochlea based on the determined time period.

In accordance with an exemplary embodiment, there is a method, comprising applying at first and second temporal locations respective electrical currents to one or more electrodes located in a cochlea of a recipient, obtaining first and second data indicative of an electrical property at a location within the cochlea, the first and second data corresponding to data obtained, respectively, at the first and second temporal locations, evaluating whether or not there is an existence of a temporal change in an electrical property within the cochlea at the location based on the obtained data, and determining whether or not there is blood and/or a clot in the cochlea based on the temporal change in the electrical property.

In accordance with an exemplary embodiment, there is a method, comprising applying at a plurality of temporal locations respective electrical currents to respective one or more electrodes located in a cochlea of a cochlear electrode array, and obtaining a plurality of respective measurement readings from electrodes within the cochlea located along the electrode array for the respective electrical currents, wherein the method includes moving the electrode array in the cochlea, and the action of obtaining the plurality of respective measurement readings is executed such that the readings are focused at a same location within the cochlea relative to other locations within the cochlea.

In accordance with an exemplary embodiment, there is a method, comprising inserting a cochlear implant electrode array into a cochlea; and interleaving neural response measurements with impedance measurements between electrodes of the cochlear implant electrode array during the insertion.

In accordance with an exemplary embodiment, there is a method, comprising applying an electrical current to one or more electrodes of an electrode array located in a cochlea of a recipient, obtaining data indicative of impedances between a plurality of groups of two electrodes corresponding respectively to different locations along the electrode array, evaluating electrical conductivity between the respective electrodes of the respective groups, determining the existence of an impedance change between the respective electrodes of the respective groups, and determining a location, density, and temporal feature of the impedance change.

BRIEF DESCRIPTION OF THE DRAWINGS

Embodiments are described below with reference to the attached drawings, in which:

1A is a perspective view of an exemplary hearing prosthesis in which at least some of the teachings detailed herein are applicable;

FIGS. 3A and 3B are side and perspective views of an electrode assembly extended out of an embodiment of an insertion sheath of the insertion guide illustrated in FIG. 2;

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIGS. 5-9 are exemplary system components of an exemplary embodiment;

DETAILED DESCRIPTION

Figure 1A:
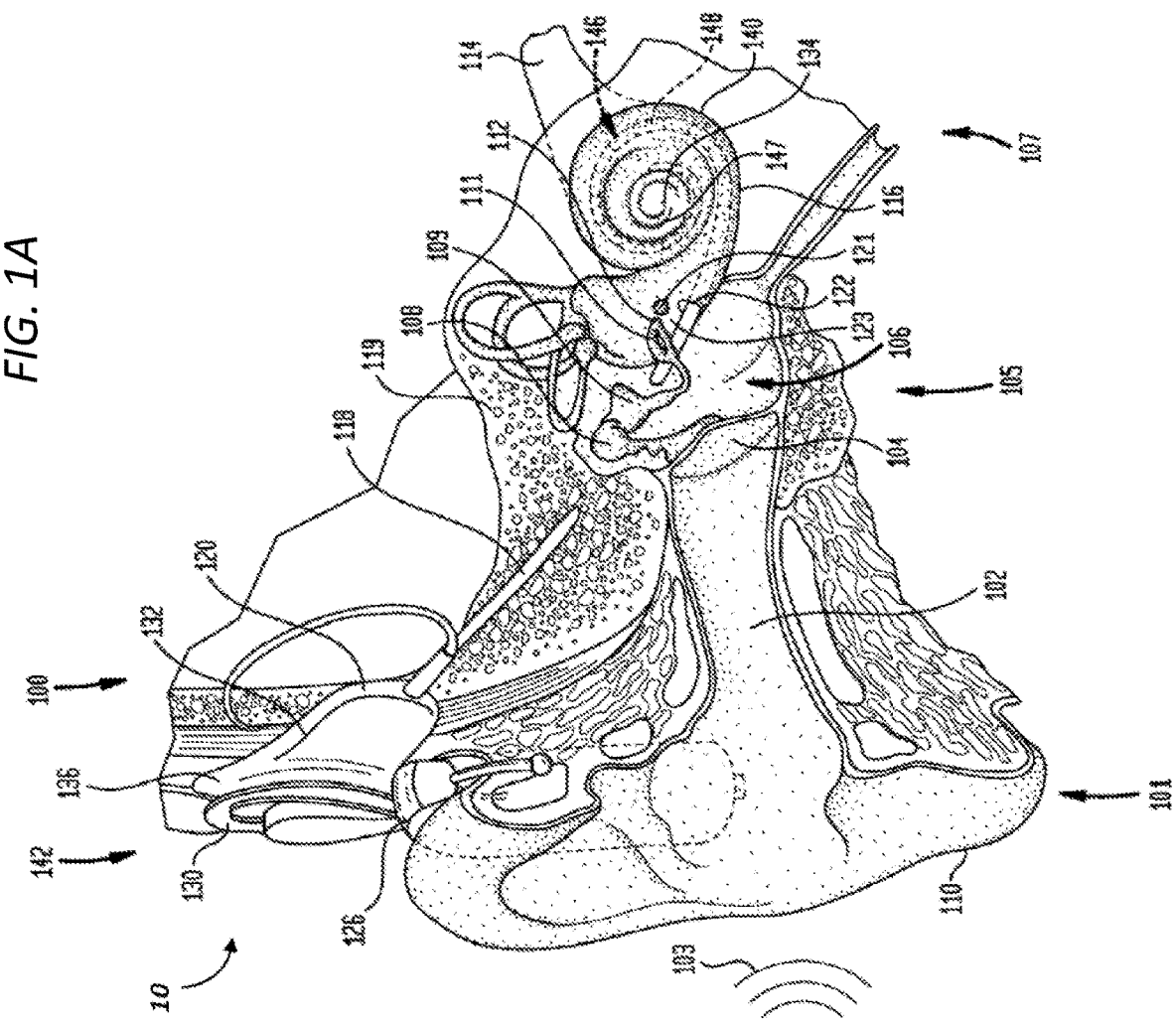
FIG. 1B depicts a side view of the cochlear implant 100 outside of the recipient.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, pacemakers, visual prostheses (e.g., bionic eyes), sensors, drug delivery systems, defibrillators, functional electrical stimulation devices, etc.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is rechargeable via the transcutaneous link.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
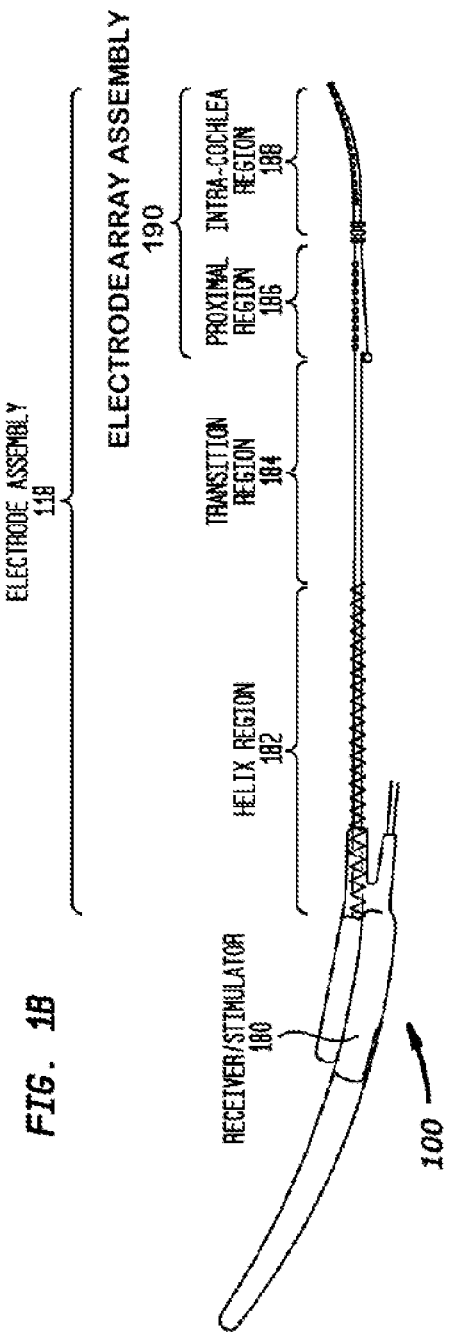

FIG. 1B is a side view of a cochlear implant 100 without the other components of system 10 (e.g., the external components). Cochlear implant 100 comprises a receiver/stimulator 180 and an electrode assembly or lead 118. Electrode assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Electrode array 146 may be inserted into cochlea 140 with the use of an insertion guide. It is noted that while the embodiments detailed herein are described in terms of utilizing an insertion guide or other type of tool to guide the array into the cochlea, in some alternate insertion embodiments, a tool is not utilized. Instead, the surgeon utilizes his or her fingertips or the like to insert the electrode array into the cochlea. That said, in some embodiments, alternate types of tools can be utilized other than and/or in addition to insertion guides. By way of example only and not by way of limitation, surgical tweezers like can be utilized. Any device, system, and/or method of inserting the electrode array into the cochlea can be utilized according to at least some exemplary embodiments.

The teachings detailed herein are directed towards identifying phenomenon inside a cochlea. Some embodiments can include utilizing imaging (e.g., CT scan, X-ray, etc.), which require the patient to be exposed to radiation during the process of obtaining medical images, as well as the need for medical equipment in the operating room to provide and otherwise obtain the imaging, as well as a subsequent analysis by an expert to assess the correct insertion of the electrode holder. Some embodiments of the teachings detailed herein utilize such, while other embodiments specifically do not utilize such, but instead utilize other methods to evaluate or otherwise obtain information indicative of a given electrode array insertion scenario. Some embodiments include the action of measuring neuronal activation after stimulation. This exemplary embodiment can require subjective expert analysis and/or can also be dependent on having a good/acceptable neural response. However, in some instances, such is not always obtainable. Again, as with the aforementioned imaging, some embodiments herein utilize such while other embodiments specifically do not utilize such methods. In at least some exemplary embodiments, methods of determining an insertion scenario can utilize voltage measurements in the cochlea. In an exemplary embodiment of such embodiments, the interpretation of the obtained voltage measurements still requires subjective analysis by an expert. In addition, these measurements can be rendered more difficult to interpret than otherwise might be the case by the presence of so-called air bubbles, open electrodes, shorted electrodes, and/or electrode extrusion. Some embodiments of the teachings detailed herein utilize the aforementioned voltage measurements coupled with expert analysis, while in other embodiments some of the teachings detailed herein specifically avoid utilization of expert analysis to obtain or otherwise analyze and electrode array insertion scenario.

Some embodiments include obtaining voltage measurements from inside and/or outside the cochlea and analyzing them in, by way of example only and not by way of limitation, an automated manner, by comparing the voltage measurements to statistical data.

Figure 2A:
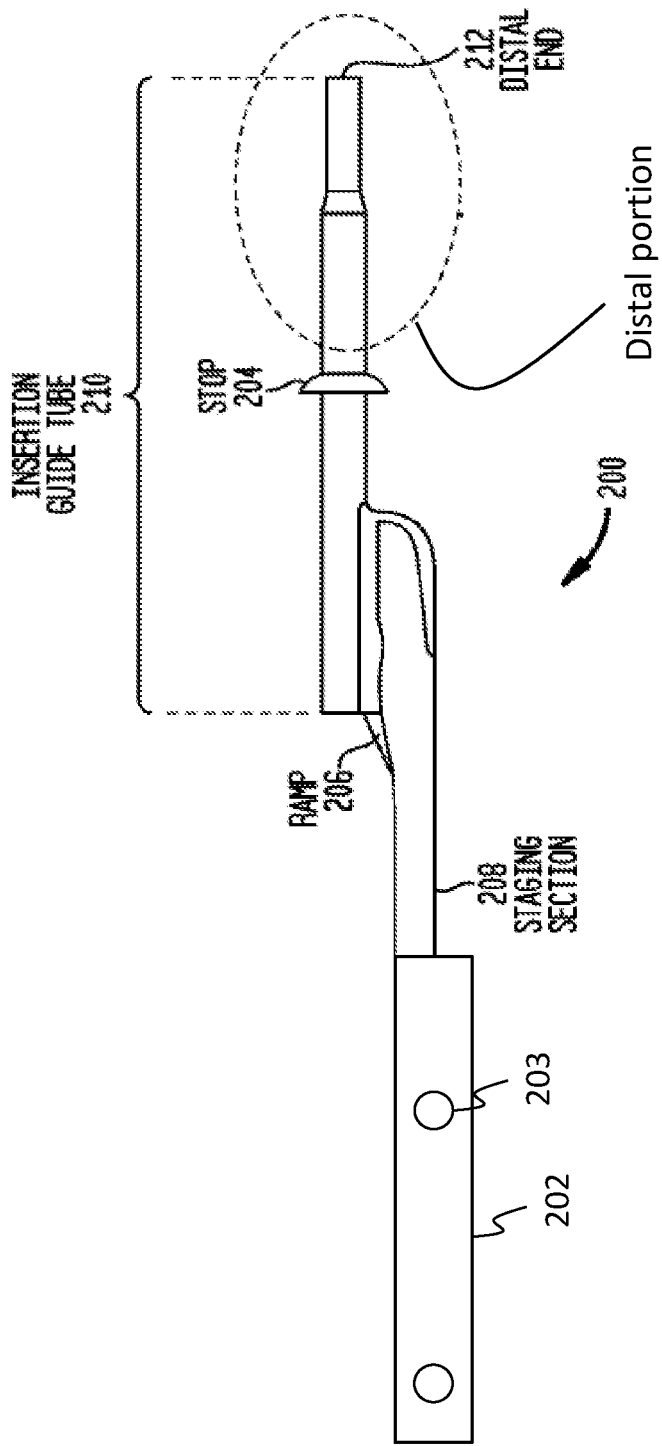
FIGS. 2A and 2B are side views of an embodiment of an insertion guide for implanting a cochlear implant electrode assembly such as the electrode assembly illustrated in FIG. 1.

FIG. 2A presents a side view of an embodiment of an insertion guide for implanting an elongate electrode assembly generally represented by electrode assembly 145 (corresponding to assembly 190 of FIG. 1B) into a mammalian cochlea, represented by cochlea 140. The illustrative insertion guide, referred to herein as insertion guide 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A robotic arm adapter 202 is mounted to a proximal end of staging section 208 to facilitate attachment of the guide to a robot, which adapter includes through holes 203 through which bolts can be passed so as to bolt the guide 200 to a robotic arm, as will be detailed below. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

Figure 2B:
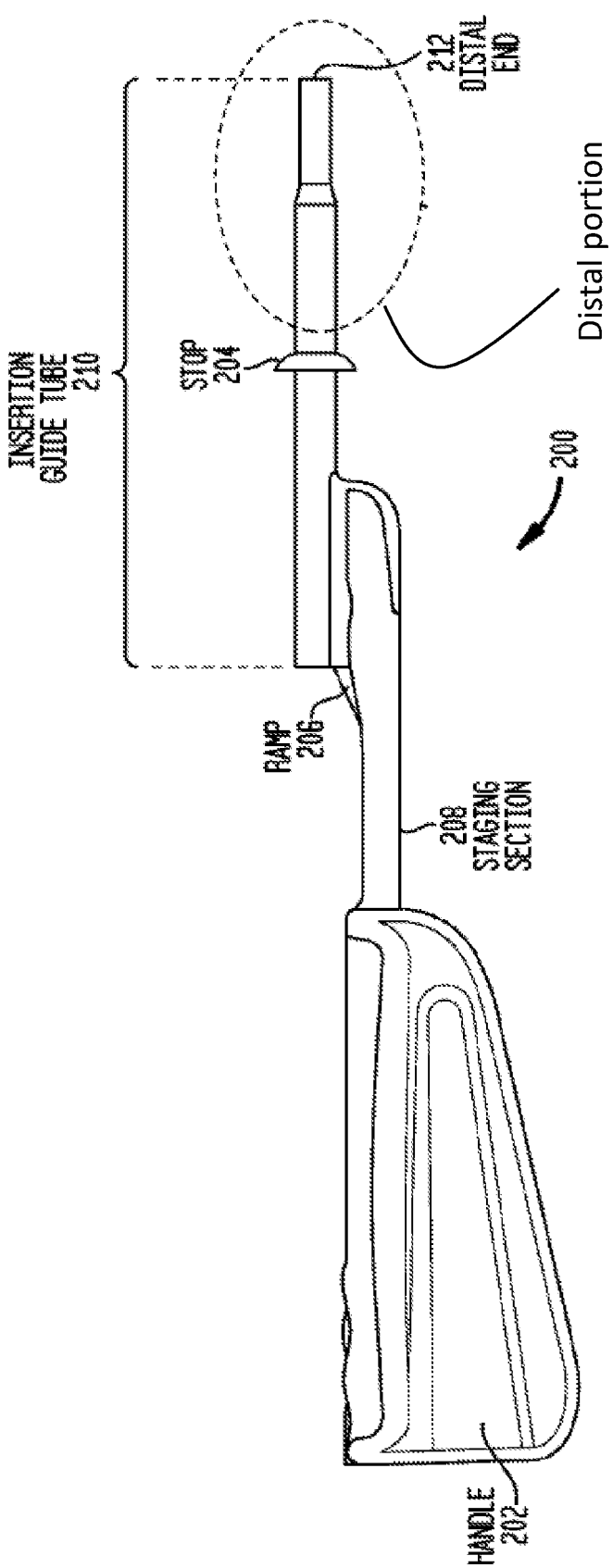

FIG. 2B depicts an alternate embodiment of the insertion guide 200, that includes a handle 202 that is ergonomically designed to be held by a surgeon. This in lieu of the robotic arm adapter 202.

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube, etc., but instead remains straight.

FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. Insertion guide tube 300 retains electrode assembly 145 in a substantially straight configuration, thereby preventing the assembly from taking on the configuration shown in FIG. 3B.

It is noted that while the embodiments above disclose the utilization of an insertion tool, in some other embodiments, insertion of the electrode array is not executed utilizing an insertion tool. Moreover, in some embodiments, when in insertion tool is utilized, the insertion tool is not as intrusive as that detailed in the figures. In an exemplary embodiment, there is no distal portion of the tool. That is, the insertion tool stops at the location where the distal portion begins. In an exemplary embodiment, the tool stops at stop 204. In this regard, there is little to no intrusion of the tool into the cochlea. Any device, system and/or method that can enable the insertion of the electrode array can be utilized in at least some exemplary embodiments.

As can be recognized from the above, the electrode array can be utilized to obtain the data utilized in the methods herein, such as by way of example only and not by way of limitation, the voltages at the read electrodes, and can also be used to provide the stimulating electrode (just in case for some reason that was not clear). FIG. 5 depicts an exemplary system for utilizing the cochlear implant to obtain such information. Presented in functional terms, there is a test unit 3960 in signal communication with unit 8310, which in turn is in signal communication, optionally with a unit 7720 and a unit 8320, the details of which will be described below.

Unit 3960 can correspond to an implantable component of an electrode array, as seen in FIG. 1. More specifically, FIG. 6 depicts an exemplary high-level diagram of a receiver/stimulator 8710 (the implantable portion of 100) of a cochlear implant, looking downward. As can be seen, the receiver/stimulator 8710 includes a magnet 160 that is surrounded by a coil 137 that is in two-way communication (although in other embodiments, the communication is one-way) with a stimulator unit 122, which in turn is in communication with the electrode array 145. Receiver/stimulator 8710 further includes a cochlear stimulator unit 122, in signal communication with the coil 137. The coil 137 and the stimulator unit 122 are encased in silicon as represented by element 199. In an exemplary embodiment, receiver/stimulator 8710 is utilized as test unit 3960, and is used to acquire information about electrode array position.

Figure 8:
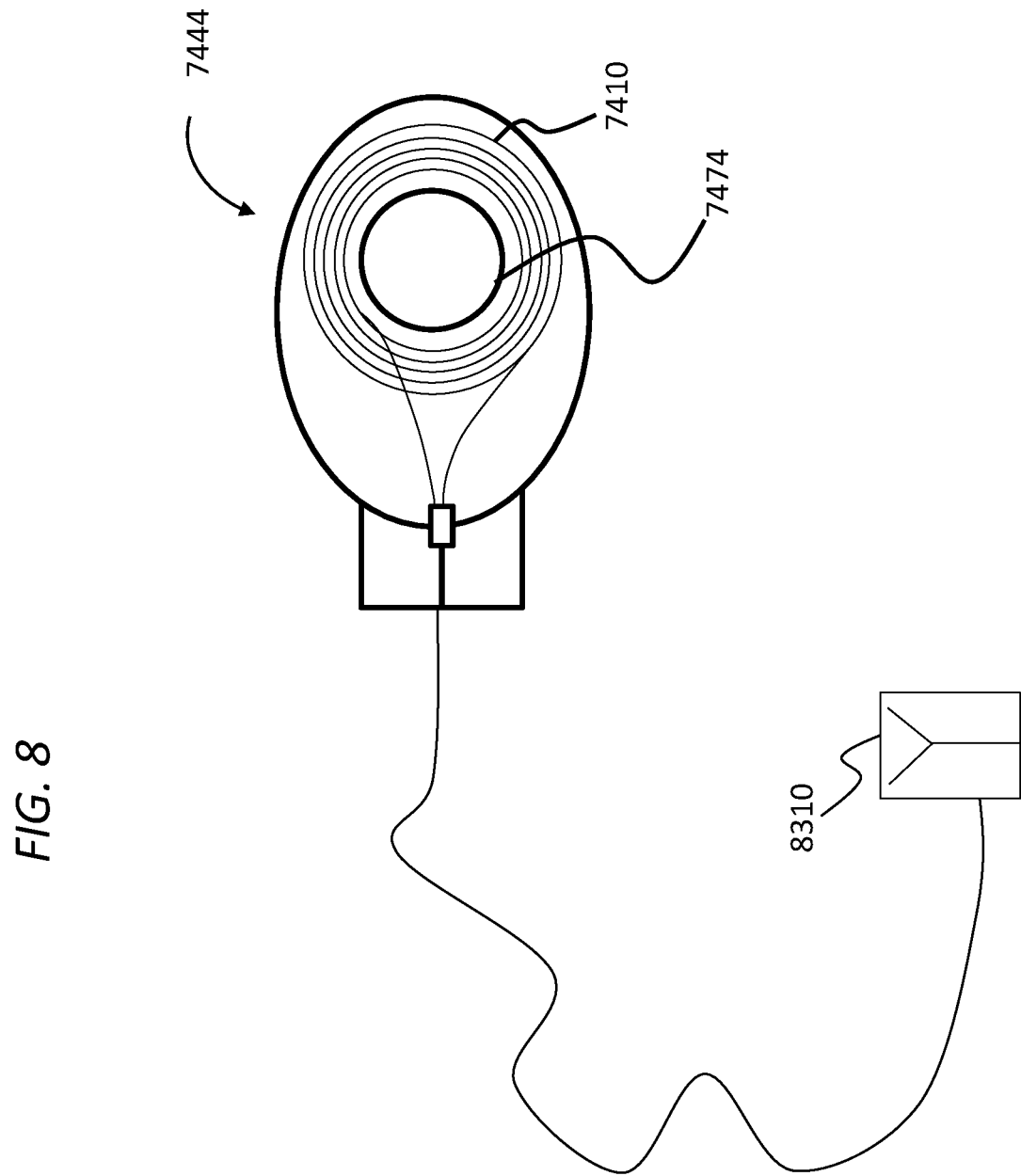

FIG. 8 depicts an exemplary RS (receiver/stimulator) interface 7444 which is presented by way of concept. An inductance coil 7410 is configured to establish a magnetic inductance field so as to communicate with the corresponding coil of the receiver-stimulator of the cochlear implant. Interface 7444 includes a magnet 7474 so as to hold the inductance coil 7410 against the coil of the receiver/stimulator of the cochlear implant in a manner analogous to how the external component of the cochlear implant is held against the implanted component, and how the coils of those respective components are aligned with one another. As can be seen, an electrical lead extends from the coil 7410 to control unit 8310, representing signal communication between interface 7444, and control unit 8310. It is noted that in an alternative embodiment, 7444 can be the external component of FIG. 1, and can have some and/or all of the functionalities just described, such that data can be obtained from the implanted portion outside of a clinical setting, such as during everyday life of the recipient.

Figure 9:
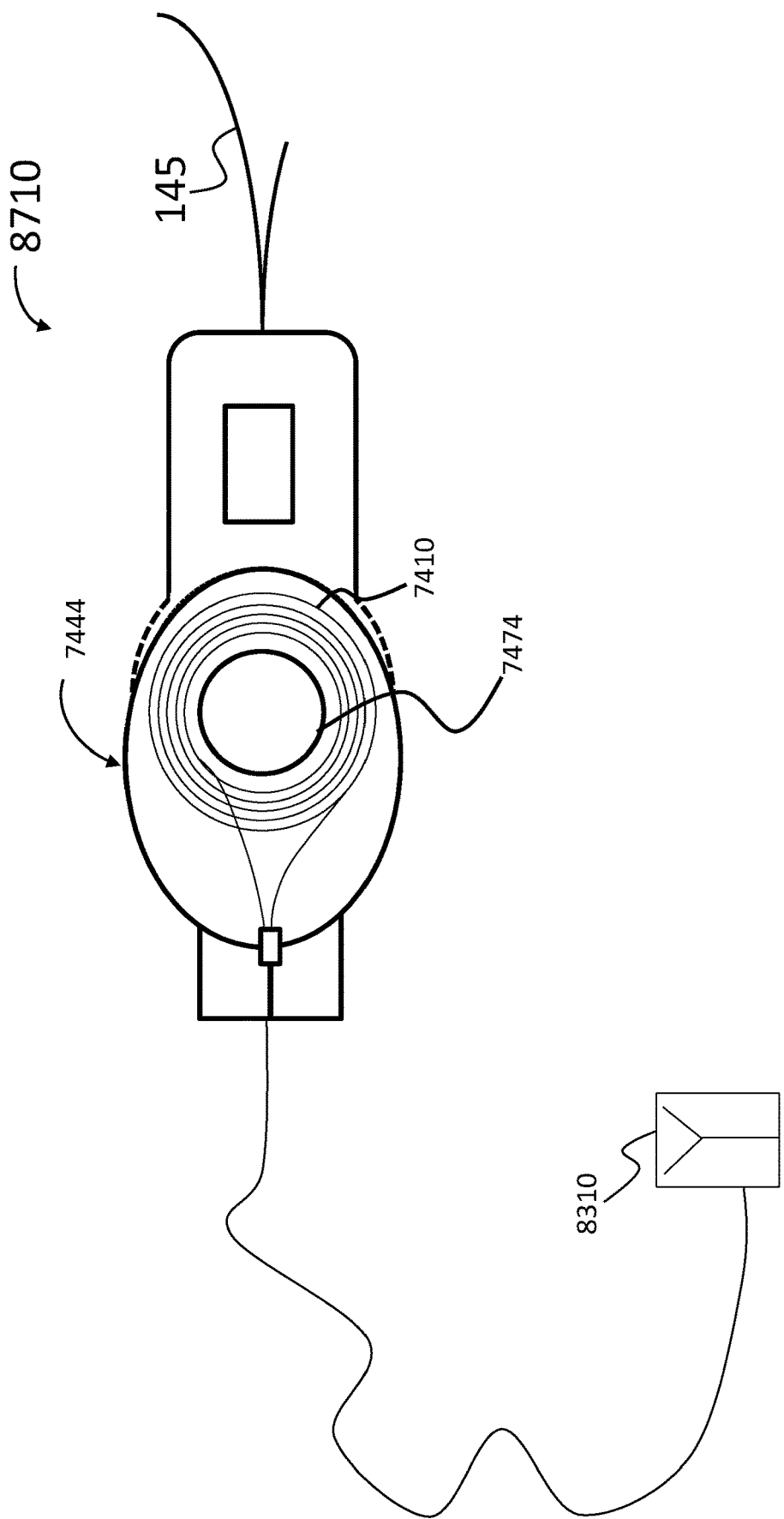

FIG. 9 depicts an exemplary embodiment of the receiver/stimulator 8710 in signal communication with the control unit 8310 via electrical lead that extends from the interface device 7444 having coil 7410 about a magnet 7474 as can be seen. The interface device 7444 communicates via an inductance field with the inductance coil of the receiver/stimulator 8710 so that the data acquired by the implantable component 8710 (receiver/stimulator) can be transferred to the control unit 8310.

Note also that in at least some alternate exemplary embodiments, control unit 8310 can communicate with the so-called "hard ball" reference electrode of the implantable component of the cochlear implant so as to enable communication of data from the receiver/stimulator 8710 to control unit 8310 and/or vice versa.

It is noted that in the embodiment of FIG. 9, control unit 8310 is in signal communication with the various other components as detailed herein, which components are not depicted in FIG. 9 for purposes of clarity.

Also functionally depicted in FIG. 5 is the optional embodiment where an electrode array insertion robotic system/actuator system 7720 and an input device 8320 is included in the system. In an exemplary embodiment, the input device 8320 could be a trigger of a hand held device that controls the actuator system 7720 and can stop and/or start the actuator for insertion of the electrode array. In an exemplary embodiment, the input device 8320 could be a trigger on the tool 8200.

Figure 7:
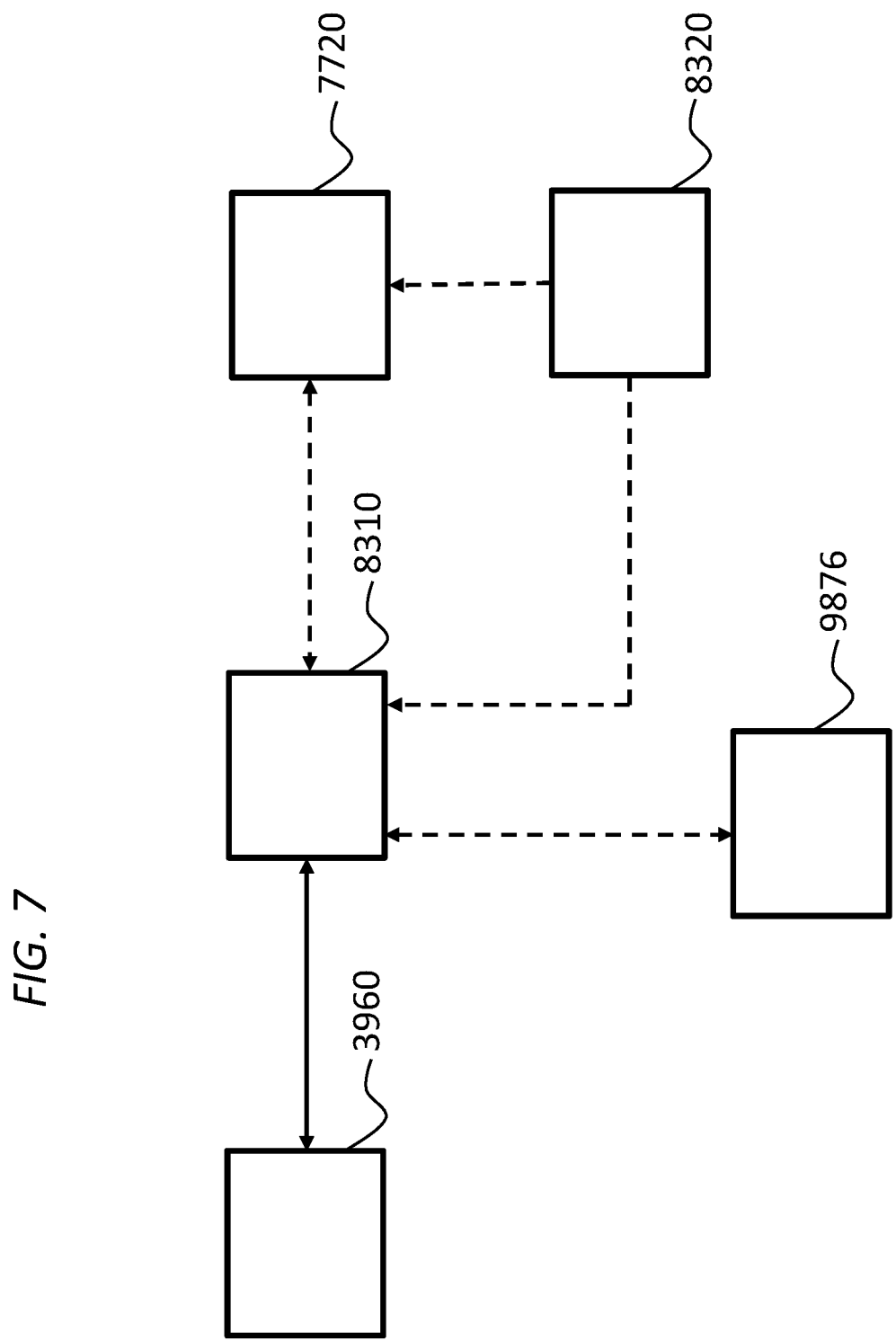

Control unit 8310 can be a signal processor or the like, or a personal computer or the like, or a mainframe computer or the like, etc., that is configured to receive signals from the test unit 3960 and analyze those signals to evaluate the data obtained (it can also be used to control the implant/control the application of current). More particularly, the control unit 8310 can be configured with software or the like to analyze the signals from test unit 3960 in real time and/or in near real time as the electrode array is being advanced into the cochlea by actuator assembly 7720 (if present, and if not present, while the array is being inserted/advanced by hand). The control unit 8310 analyzes the input from test unit 3960, after partial and/or full implantation and/or after the surgery is completed and/or as the electrode array advanced by the actuator assembly 7720 and/or as the electrode array is advanced by the surgeon by hand. The controller/control unit can be programmed to also control the stimulation/control the providing of current to the electrodes during the aforementioned events/situations. The controller 8310 can evaluate the input to determine if there exists a phenomenon according to the teachings detailed herein. The controller can evaluate telemetry, or otherwise receive telemetry, form the implant, via the device that communicates with the implant. That said, in an alternate embodiment, as depicted in FIG. 7, or in addition to this, the controller 8310 can output a signal to an optional monitor 9876 or other output device (e.g., buzzer, light, etc.), that can provide the surgeon or other healthcare professional performing the operation or evaluating the data postoperatively, etc., indicative of the data obtained and/or indicative of a conclusion reached by the control unit 8310. Note also that in an exemplary embodiment, the control unit 8310 can be a dumb unit in the sense that it simply passes along signals to the implant (e.g., the control unit can instead be a series of, for example, buttons where a surgeon depression is one button to provide stimulation to a given electrode). The control unit 8310 can be an external component of the cochlear implant.

Still, in some embodiments, the control unit 8310 is configured or otherwise programmed to evaluate input and determine if the input indicates that the electrode array is positioned in a given manner were otherwise that the electrode array is positioned in a manner different than that which was desired or otherwise determine any of the features detailed herein. In an exemplary embodiment, upon such a determination, control unit 8310 could halt the advancement of the array into the cochlea by stopping the actuator(s) of actuator assembly 7720 and/or could slow the actuator(s) so as to slow rate of advancement of the electrode array into the cochlea and/or could reverse the actuator(s) so as to reverse or otherwise retract the electrode array within the cochlea (either partially or fully). Alternatively, in embodiments where actuator assembly 7720 is not present, control unit 8310 could provide an indication to the surgeon or the like (via an integrated component, such as a buzzer or a light on the control unit, or an LDC screen, or via device 9876) to halt and/or slow the insertion, etc. In at least some exemplary embodiments, control unit 8310 can be configured to override the input from input unit 8320 input by the surgeon or the user.

Some exemplary embodiments utilize the receiver/stimulator 8710 as a test unit 3910 that enables the action of obtaining the data and the action of providing current to the electrode, and/or any one or more of the method actions detailed herein. In an exemplary embodiment, the receiver/stimulator 8710 and/or control unit 3810 and/or actuator assembly 7720 and/or input device 8320 are variously utilized to execute one or more or all of the method actions detailed herein, alone or in combination with an external component of a cochlear implant, and/or with the interface 7444, which can be used after the receiver/stimulator 8710 is fully implanted in the recipient and the incision to implant such has been closed (e.g., days, weeks, months or years after the initial implantation surgery). The interface 7444 can be used to control the receiver/stimulator to execute at least some of the method actions detailed herein (while in some other embodiments, the receiver/stimulator can execute such in an autonomous or semi-autonomous manner, without being in communication with an external component) and/or can be used to obtain data from the receiver/stimulator after execution of such method actions.

Some exemplary utilizations of the embodiments of FIGS. 5-9 will now be described, along with some modifications thereto.

Extensive fibrosis formation post-cochlear implantation can be less than utilitarian, and, in some instances, deleterious, to hearing preservation. In some instances, very early tissue response post-implantation, 1 day, for example, can be used to predict a tissue response. Severe hair cell (HC) loss, ossification and formation of the early tissue response (leading to fibrosis) may be dictated by the amount of intra-cochlear trauma sustained during the surgical approach and insertion of the electrode array.

In some instances, intra-cochlear blood contamination can trigger an intracochlear inflammation, or otherwise can be an indication that trauma has occurred, such as, for example, as a result of insertion into the electrode array. The source of the intra-cochlea blood can be, for example, from micro-tears on the lateral wall or from the cochleostomy in the bony wall of the cochlea. As HC loss, extensive fibrosis, and ossification may be directly related to hearing loss, there can be utilitarian value in finding methods to either remove this contaminating blood from the cochlea or disrupt the intra-cochlear inflammatory cascade in an effort to minimize possible deleterious effects described above. Some embodiments are directed to identifying the presence of blood, or a blood clot, or the presence of trauma, in the cochlea. In some embodiments, there are methods and/or devices to remove or at least minimize the deleterious effects of intra-cochlear blood contamination during either cochlear implant surgery or immediately post-operatively. In some embodiments, there are methods and/or devices to detect the blood contamination, and, in some embodiments, to do so at a temporally utilitarian manner in general, and in some embodiments, to do so in a temporally utilitarian manner that is more utilitarian than when done in another temporal manner. In some embodiments, there is the use of one or more biomarkers to detect the onset, location, and/or blood clot formation of an intra-cochlear bleed, which can be caused by cochlear array implantation. Some embodiments also include methods of how this blood clot may be minimized in volume at the time of surgery and/or post-implantation.

In view of the above, some embodiments include the utilization of, for example, one or more of the systems detailed above, to obtain electrode voltage measurements along the electrode array inserted into the cochlea and/or as the electrode array is inserted into the cochlea. Some embodiments also include the identification of electrode voltages that indicate the local presence of blood and/or clotting. Some embodiments also include an analysis, such as an automatic analysis and/or semiautomatic analysis, such as by the systems detailed above, of the electrode voltages to determine the source of the blood flow, the temporal spread of the blood and/or the evolution of the blood clot further, some embodiments include utilizing the aforementioned data to make a determination that there should be removal and/or remediation of the blood clot (or resultant inflammatory processes) by physical or pharmacological methods, and also embodiments herein include doing so.

Bipolar stimulation of a cochlear implant, such as where two electrodes of the electrode array implanted in the cochlea or otherwise in the cochlea at the time that bipolar stimulation is executed are respectively utilized as the source and a sink, produces a dipole within the cochlea. The quantity of current flowing out of a current source is at least effectively equal (including equal) to the current flowing back into the current source, in some embodiments where the source and sink are located in a cochlea with perilymph immersing both the source and a sink in a contiguous manner. By ensuring or otherwise utilizing current flow in the path of least impedance, the introduction of blood into a homogenous medium can cause an increase in the impedance between the source and the sink. In at least some exemplary embodiments, the cochlear implant electrode array 146 provides stimulation to tissue utilizing a current source and sink established by two electrodes of the electrode array. In an exemplary embodiment, this current source provides sufficient current into tissue of the recipient to evoke a hearing percept. In some embodiments according to the teachings detailed herein, irrespective of whether or not a hearing percept is executed, although some embodiments apply a current that creates current flow within the cochlea where no hearing percept is evoked and/or the threshold level at a given frequency for that recipient is higher than the current utilized, while in other embodiments, a hearing percept is evoked, the current flow generated by the stimulating electrodes will flow according to an impedance within the cochlea.

Figure 10:
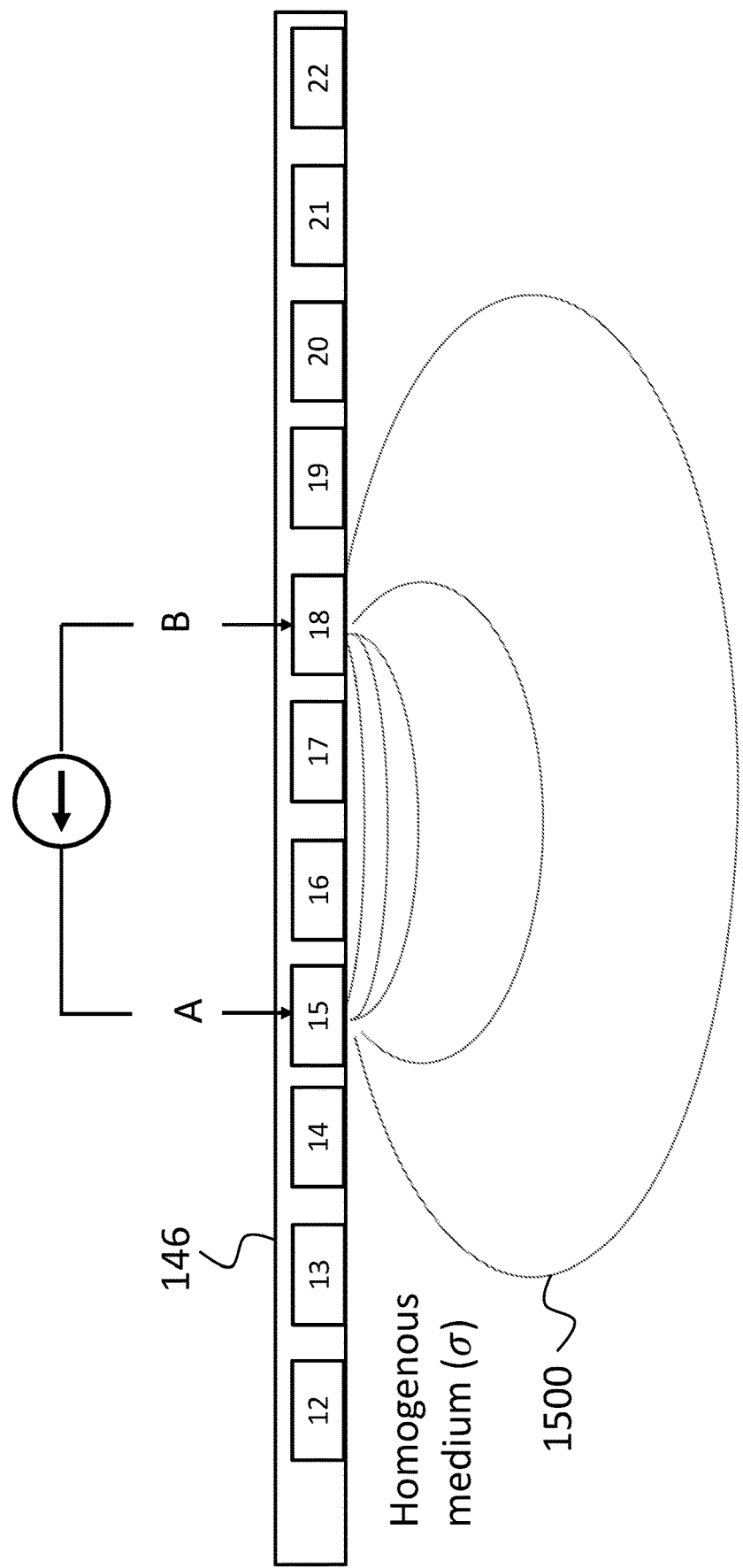
FIG. 10 depicts an exemplary 4 point impedance measurement.

FIG. 10 shows an exemplary conceptual diagram of current flow between a source and a sink of an electrode array within the cochlea. Thus if the relative voltage is measured between ICE16 (ICE being intra-cochlear electrode—as distinguished from an electrode that is not in the cochlea, at least not when the measurement is executed) and ICE17, where electrodes 15 and 18 (ICE electrodes 15 and 18) are the stimulating electrodes (source and sink), in some exemplary scenarios, the voltage difference would be a certain value with respect to a cochlea in which no blood is present and another value (a higher value, in at least some instances), where there is blood in the cochlea. Thus, FIG. 10 depicts a 4-point impedance measurement regimes. By using such measurement regimes, differences between the 4-point (bulk) measures due to different biological mediums can be detected, and used to utilitarian value.

Figure 11:
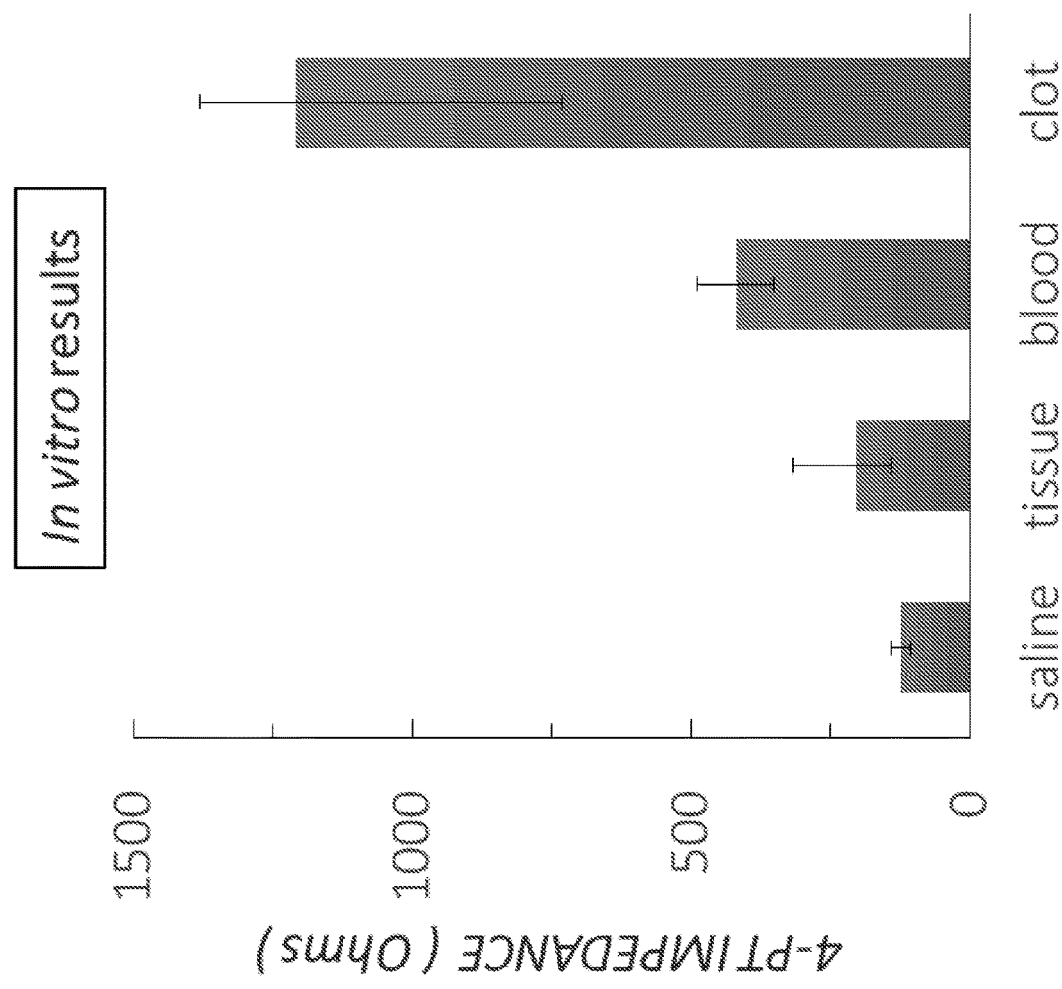
FIGS. 11-13 present exemplary data according to some embodiments.

More particularly, FIG. 11 depicts exemplary in-vitro measures of 4-point impedance using an electrode array immersed in saline, tissue, blood, and clotted blood. The elevated 4-point measures for blood and clotted blood are distinguishable above that of saline and tissue measures. Thus, by evaluating the impedance between the read electrodes, the presence and/or absence of certain phenomenon in the cochlea can be inferred or otherwise deduced.

Embodiments include a multi-contact cochlea electrode array, such as those detailed above, an implant with extra-cochlear electrodes (or another component, such as one that works in conjunction with the implanted portion of the cochlear implant, a receiver stimulator (such as that of the implanted portion), which can be either fully implanted or powered by an external behind the ear (BTE) processor or other external device. The implanted portion can include a built in-built amplifier configured to measure electrode voltages concurrent to the delivery of electrical current to either the same or adjacent electrode contacts.

In some instances, a method is executed whereby the implanted portion of the cochlear implant (e.g., receiver stimulator) or another device, such as the control unit detailed above, coordinates measurement electrode voltages in response to electrical stimulation to one or more contacts such that a measure of bulk impedance between two electrode contacts can be estimated. This bulk impedance is calculated for a number of locations along the electrode array in some embodiments. These measurements may be repeated continuously over time, either during the insertion of the electrode array or post-insertion when the electrode is static in position (either during the surgery or post-operatively).

Methods further include detection and analysis, wherein, in some embodiments, the system or external apparatus (BTE or computer/control unit, for example) analyzes the measured impedances/measured voltages along the array (at one or more or all possible locations) to determine the location, density and/or temporal nature of the bulk impedance changes. These changes in bulk impedance are employed to determine or otherwise infer that blood is present around the electrode array.

Figure 12:
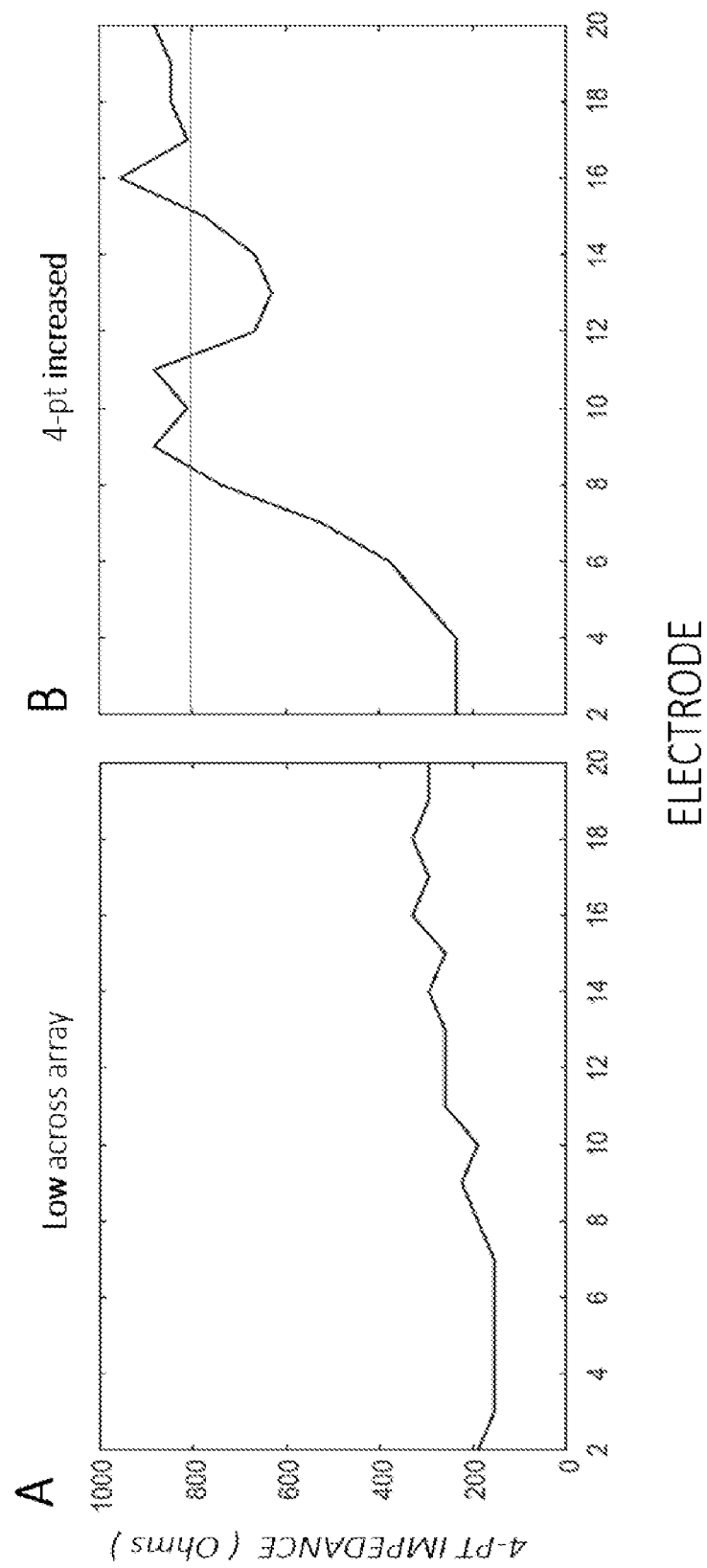

FIG. 12 depicts graphs of impedance between read electrodes at two different times (Time A and Time B, for charts A and B, respectively). The graphs depict the impedances between two electrodes, where the number presents the electrode with the lower number (i.e., 2 represents the read pair of electrodes 2 and 3, 20 represents the read pair of electrodes 20 and 21, etc.). This number is referred to as the base electrode (for no other reason than to establish a standard—if the base electrode was the higher number, the charts would start with 3 and end with 21, but the data would be the same). As can be seen, the impedance increases, in some instances, significantly, between time A and time B for the various read pairs, and in some instances, more for some pairs than others.

With respect to FIG. 12, the respective two plots of 4-point impedances across the entire electrode array are for measurements immediately after the electrode insertion in the operating room and then a time period less than 10 minutes (e.g., less than 1, 2, 3, 4, 5, 6, 7, 8, 9, or 10 minutes) after the initial inserting/after the measurements for plot A.

Figure 13:
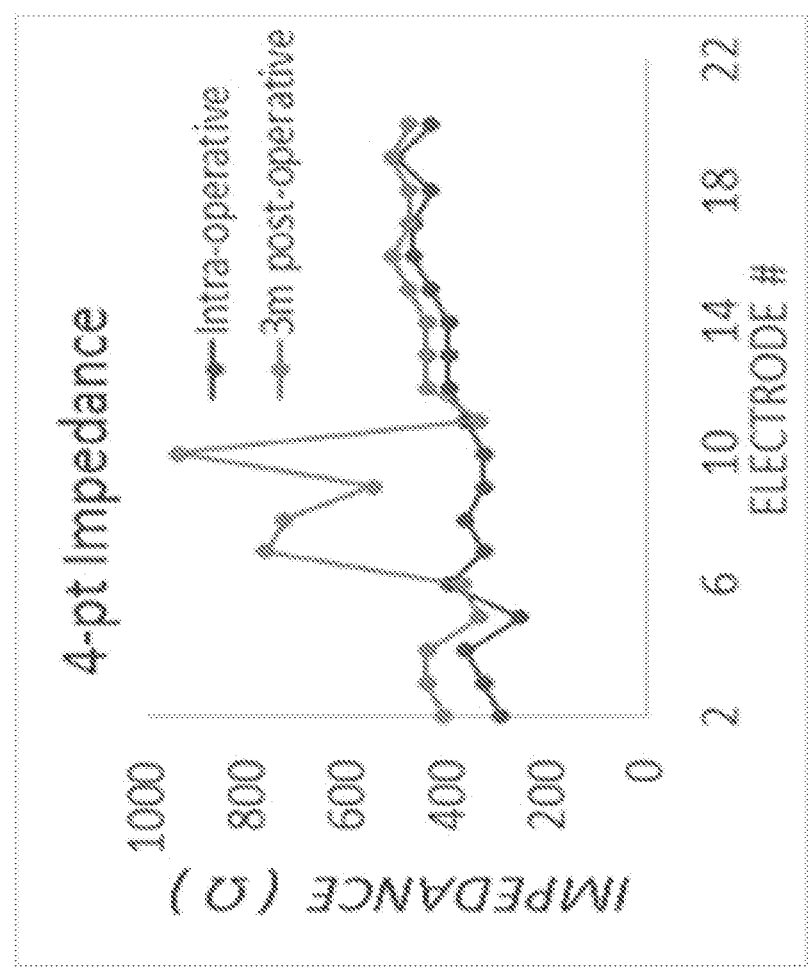

Some embodiments include analysis that can detect the spread of the blood along the array and/or characterize the evolution of the blood clotting process. In some embodiments, there is an analysis that includes blood source localization techniques to identify the anatomical source (location) of the bleeding in the cochlea. For measures conducted post-operatively, the bulk impedance measures are analyzed along with the ECoG signal to determine the progressive development of a fibrotic response around the electrode array; the ECoG component can be utilized to determine if the biomechanics (such as the displacement of the basilar membrane) of the cochlear are impacted by this fibrotic growth, as seen in FIG. 13. Specifically, the graph of FIG. 13 depicts the 4-point and cochlear microphonic response changes between an intra-operative and three month post-operative measure. As can be seen, FIG. 13 illustrates a significant change in 4-point impedance profile between electrodes 6 and 11 of the array only visible three months post-op. The increase in 4-point profile indicates the development of extensive fibrosis proximal to electrodes 6-11.

Figure 14:
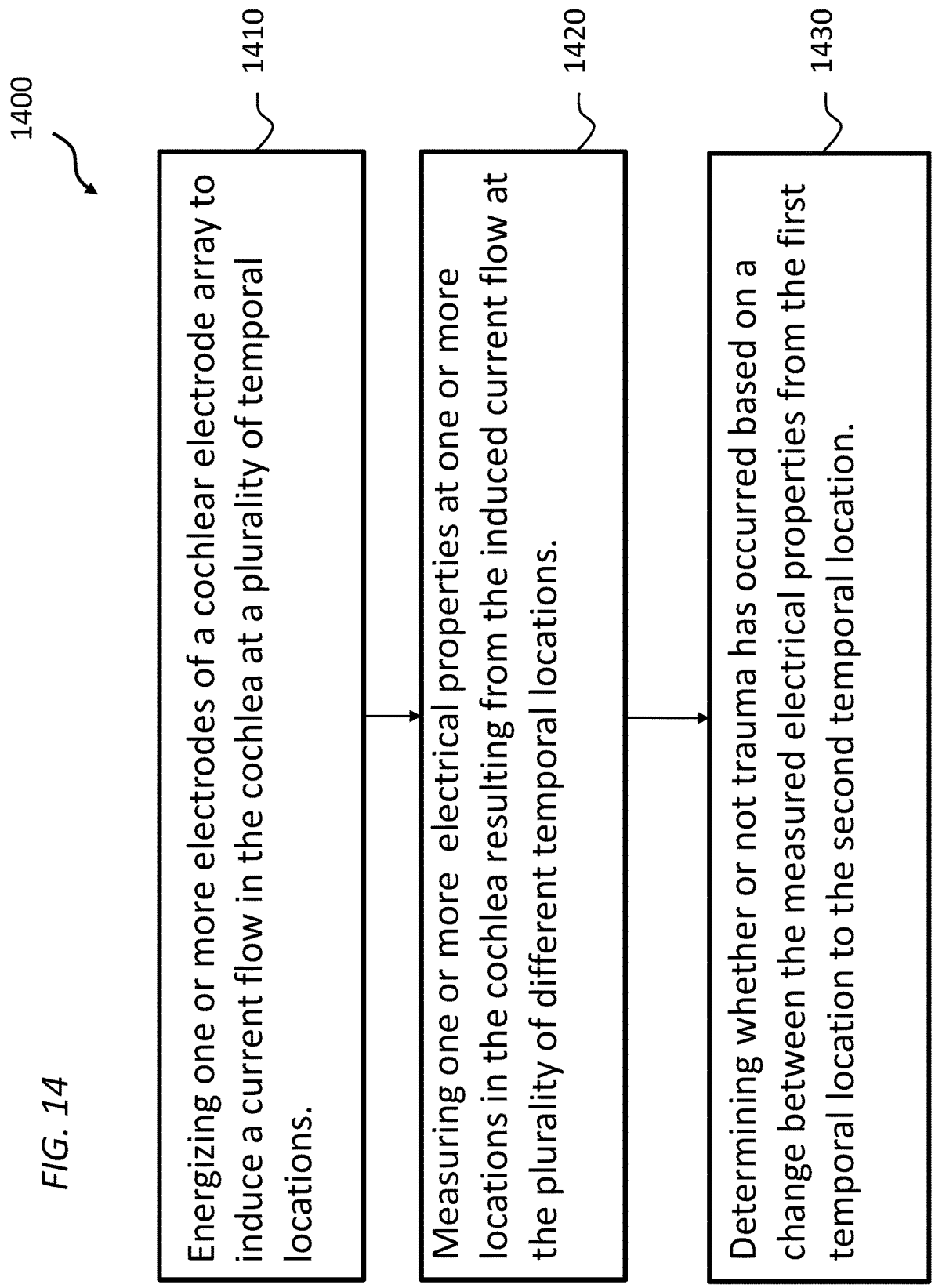
FIGS. 14-19 present exemplary algorithms for exemplary methods.

In view of the above, FIG. 14 presents an exemplary flowchart for an exemplary algorithm for a method, method 1400, which includes method action 1410, which includes energizing one or more electrodes of a cochlear electrode array to induce a current flow in the cochlea at a plurality of temporal locations. By way of example only and not by way of limitation, in an exemplary embodiment, this can include energizing electrode 19 and/or 22 (where 19 and 22 are alternatingly utilized as a source and sink when both are energized). Other electrode(s) can be energized. In some exemplary embodiments, the electrodes that are energized of electrodes and are located at about the middle of the electrode array (e.g., electrodes 9 and 12), because, in an exemplary embodiment, that represents a middle ground for blood flow in the cochlea from any direction. In some exemplary embodiments, the electrodes that are energized by the electrodes that are as proximate as utilitarian to the basal turn (keeping in mind that there is utility with respect to having the read electrodes to the basal turn—more on this below). Any energizement regime that can enable the teachings detailed herein can be utilized in at least some exemplary embodiments. Note further that method action 1410 can include energizing different pairs of the electrodes in a temporally spaced apart manner but where collectively, the energizement corresponds to a single temporal location. For example, in embodiments where the basal turn is the focus of interest, various electrode pairs can be energized as different sections of the electrode array pass by the turn during insertion. Accordingly, in an exemplary embodiment, for the first temporal location, the temporal location can span a time period where electrodes 19 and 22 are energized, then electrodes 18 and 21 are energized, then electrode 17 and 20 are energized, and so on, where the last electrode pair that is energized can end the time period of the first temporal location. Note also that in an exemplary embodiment, the aforementioned energizement regime need not necessarily occur only during insertion. Such can be executed while the electrode array is stationary, such as immediately after full insertion thereof.

With respect to the different temporal locations, the first temporal location can be executed shortly after the electrode array is fully inserted into the cochlea, and the second temporal location can be executed about 1, 2, 3, 4, 5, 6, 7, 8, 9, 10, 11, 12, 13, 14, or 15 minutes or any value or range of values therebetween in 1 second increments, e.g., about 4 minutes and 13 seconds, between 2 minutes and 33 seconds to 3 minutes 22 and seconds, etc.). In some embodiments, the first temporal location can be during the insertion process and the second temporal location can be any of the aforementioned values after the first temporal location.

Method 1400 also includes method action 1420, which includes measuring one or more electrical properties at one or more locations in the cochlea resulting from the induced current flow at the plurality of different temporal locations. In an exemplary embodiment, the location can be at the basal turn of the cochlea, and the measured properties can be properties that are measured as various electrodes become proximate to the basal turn during insertion of the electrode array. In an exemplary embodiment, the measured electrical properties are at different locations along the electrode array after the electrode after the electrode array is fully inserted, which could result in data according to plots A and B of FIG. 12. That said, the data according to plots A and B of FIG. 12 can also be obtained by reading the read electrodes as those electrodes become proximate to the specific location in the cochlea. That is, the first temporal location can correspond to a period of time that it takes from the first pair of read electrodes to become proximate to a given location to the time that it takes from a less pair of read electrodes to become proximate to a given location during electrode insertion. With respect to the aforementioned basal turn location, it could be that in some embodiments, the plots of A and/or B will begin only at electrode 7 or 8 or 9 or 10 or 11 or 12 or so, as the electrodes below those values may not reach the basal turn, ever.

Method 1400 also includes method action 1430, which includes determining whether or not trauma has occurred based on a change between the measured electrical properties from the first temporal location to the second temporal location. In an exemplary embodiment, method action 1430 can include the action of analyzing the change in the measured electrical property to identify indications of blood (and/or clot) in the cochlea, and upon a determination that an indication of blood in the cochlea is present, determining that trauma has occurred (or, upon a determination that an indication of blood (and/or clot) in the cochlea is not present, determining that trauma has not occurred).

Method action 1430 can be executed by the control unit of FIG. 5, or by the external component of the cochlear electrode array, providing that such is programmed to execute such. This can be done automatically or manually.

A variation of method 1400 can include the action of evaluating a time period between the first temporal location and the second temporal location, and, based on the evaluation of the time period, determining that trauma has occurred. By way of example only and not by way of limitation, the second temporal location can be any time after the first temporal location. Note that the embodiment of method 1400 can be such that the second temporal location can occur after a third, a fourth, fifth, a sixth, a seventh, an eighth, a ninth, or more temporal locations. In this regard, the second temporal location can be a temporal location with the measurements indicate a significant event as compared to other temporal locations. By way of example only and not by way of limitation, the application of electrical current and the measurements can be executed for, for example, 10 different temporal locations, where the seventh temporal location after the first temporal location is the first temporal location that indicates a significant change in the impedance at the location(s) of interest in the cochlea. In this regard, by way of example only and not by way of limitation, with respect to the plots of FIG. 12, the seventh temporal location could be the first temporal location where the measurements results in one or more impedances that are above 800 ohms, as is represented by way of example only and not by way of limitation, in plot B. Accordingly, the time period between the first temporal location and the seventh temporal location can be evaluated, and upon a determination that the time between the two meets a certain criteria (or does not meet a certain criteria), a determination can be made that trauma has occurred (for example, trauma resulting at the time of insertion or otherwise proximate thereto). By way of example only and not by way of limitation, if the time period between the temporal locations is less than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes), depending on other circumstances in some instances, a determination can be made that trauma has occurred, and if the time period between the temporal locations is greater a value, a determination can be made that trauma has not occurred. Note also that the latter temporal location can simply be a final temporal location. There need not be a rise in impedance. The lack of a rise in impedance by the second temporal location can indicate no trauma. That is, based on the evaluation of the time period between the pertinent temporal locations, a determination is made that trauma has not occurred.

Figure 15:
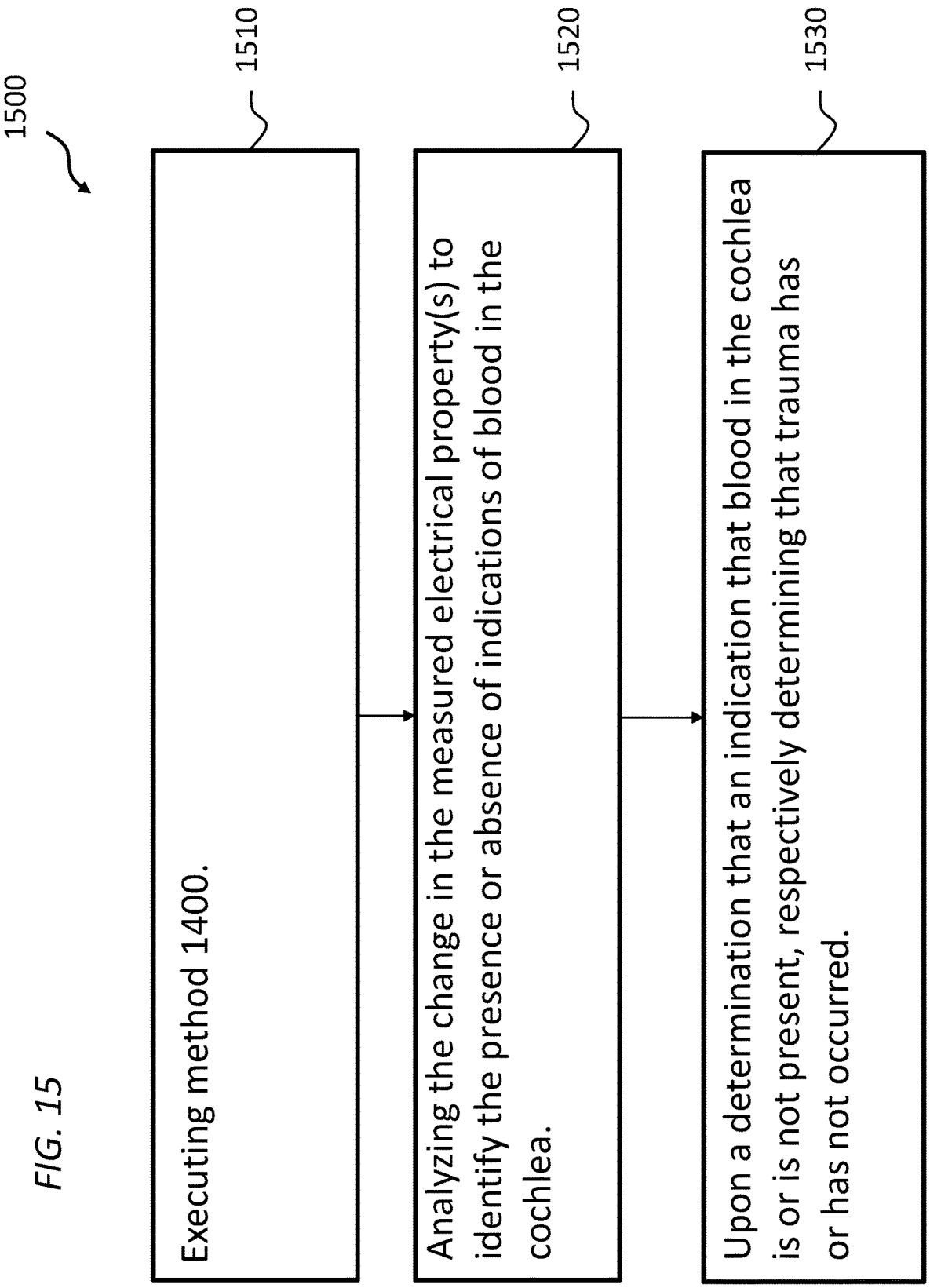
Figure 16:
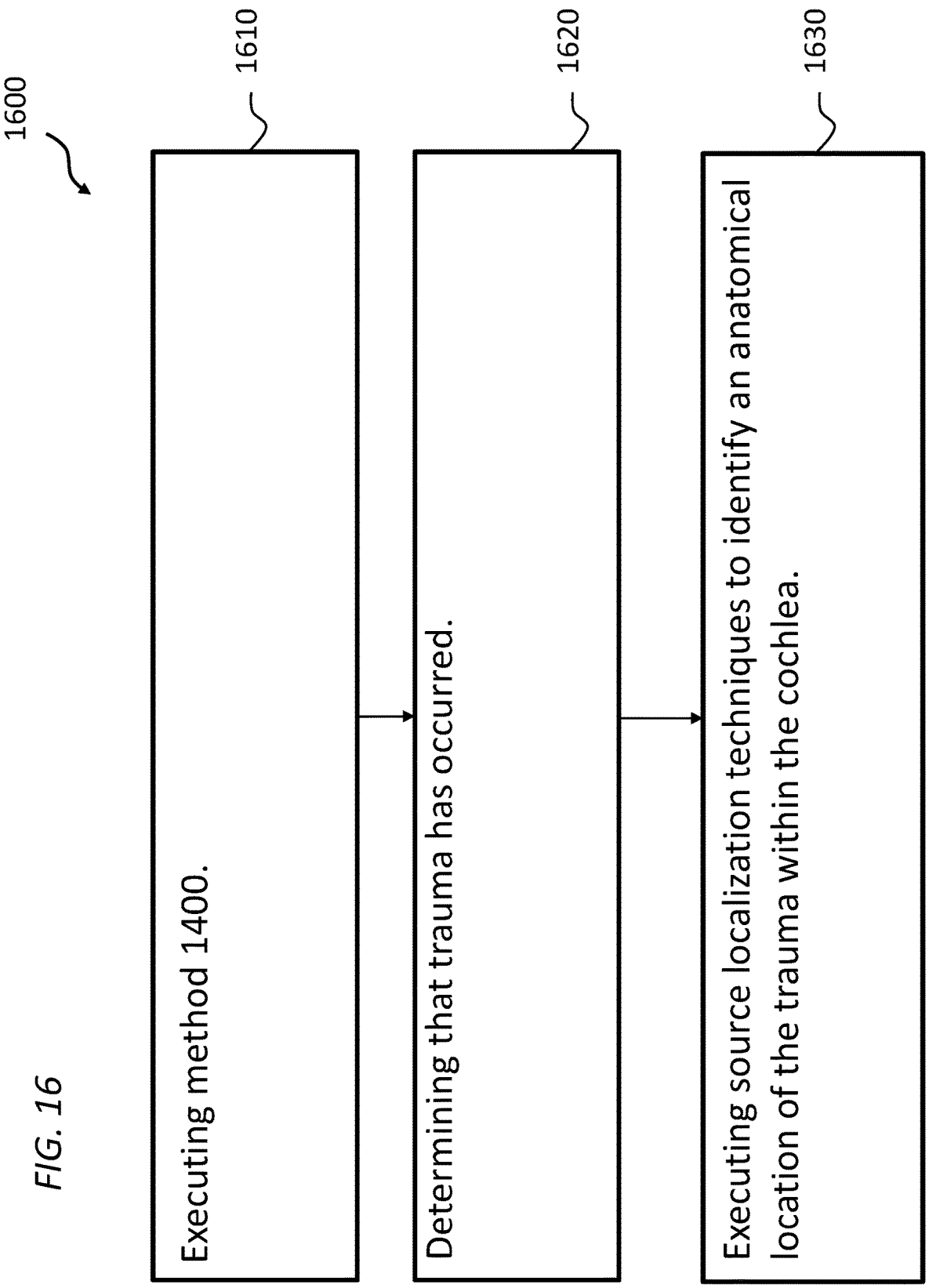

FIG. 15 presents another exemplary algorithm for an exemplary method, method 1500, which includes method 1510, which includes executing method 1400. Method 1500 also includes action 1510, which includes analyzing the change in the measured electrical property(s) to identify the presence or absence of indications of blood in the cochlea, and includes method action 1520, which includes, upon a determination that an indication that blood in the cochlea is or is not present, determining that trauma has nor has not occurred, respectively. It is noted that a variation of the method 1500 includes analyzing the change in the measured electrical property(s) to identify indications of blood in the cochlea and upon a determination that an indication that blood in the cochlea is present, determining that trauma has occurred, while another variation includes analyzing the change in the measured electrical property(s) verify that there are no indications of blood in the cochlea and upon a determination that an indication that no blood in the cochlea is present, determining that trauma has not occurred.

FIG. 1600 presents an exemplary method, method 1600, according to an exemplary embodiment. Method 1600 includes method action 1610, which includes executing method 1400. Method 1600 also includes method action 1620, which includes determining that trauma has occurred, and executing method action 1630, which includes executing source localization techniques to identify an anatomical location of the trauma within the cochlea. In an exemplary embodiment, a spike in the measurements readings at certain electrodes can be used to indicate or otherwise localize the point where the bleeding occurs or where there is a tear in the outer wall of the cochlea. (It is noted that in at least some instances, the 90° curve of the cochlea is a location that tends to be, statistically speaking, more prone to trauma than other locations within the cochlea. As will be described in greater detail below, embodiments include focusing on this location, and upon a determination that a localized increase in impedance is present at that location as opposed elsewhere, a determination can be made there is a high likelihood that trauma has occurred at the location. The focus on this location can also be utilized as a manner to eliminate false positives—if the localized increases occur at this location and not elsewhere, it is likely an indication that the data is correct, as opposed to the existence of increases in impedance at other locations as opposed to this location—not that that cannot happen, but such would be indicative of potentially another problem other than a tear in the cochlea wall.)

In this regard, in an exemplary embodiment, the impedances between read electrodes closer to a source of blood flow into the cochlea will increase, in some embodiments, at temporal locations before impedance increases between read electrodes at locations further away to a source of blood flow into the cochlea. Accordingly, in an exemplary embodiment, there is a method of evaluating the temporal locations of increases in impedance measurements at different spatial locations along the electrode array and comparing the spatial locations and the temporal locations to each other to determine the location of the trauma. For example, in an exemplary embodiment where there is an electrode array that is fully inserted in the cochlea, where for the purposes of discussion herein, electrode 1 is the most basal electrode and electrode 22 is the most apical electrode, and increase at temporal location 10 of impedance between read electrodes 10 and 11 that is greater than any impedance increase between read electrodes 7 and 8 and/or, for example, at read electrodes 14 and 15, at temporal location 10, where, for example, subsequently after temporal location 10, at temporal location 11 for example, an increase in impedance is seen between the read electrodes 7 and 8 and 14 and 15 relative to that which existed at location 10, a determination can be made that the source of the trauma is at a location proximate read electrodes 10 and 11.

Another way of identifying an anatomical location of the trauma within the cochlea could be to look at the different impedances between read electrodes for a single given temporal period. By way of example, plot B of FIG. 12 indicates that there could be trauma at a location around electrodes 7, 8, 9, 10, 11, and 12 and/or around electrodes 15, 16, 17, and 18, based on the fact that the impedances are higher at those locations.

In at least some exemplary embodiments, the underlying physical phenomenon upon which some of the teachings detailed herein rely, without being bound by theory, is that the trauma can be a tear or laceration in a wall of the cochlea, and that the blood will first enter the cochlea at that location, and thus there will be an increase in the impedance of the fluids inside the cochlea beyond that which would be the case for normal perilymph, and that this would be localized, initially, at the trauma location, and then, over time (over seconds or minutes), the blood would defuse or otherwise disperse throughout the cochlea in a more uniform manner. By obtaining readings in close temporal proximity to the beginning of blood flow into the cochlea relative to later temporal periods, the location of the intrusion, and thus the trauma, can be identified.

Note also that in an exemplary embodiment, it is possible that diffusion techniques are not utilized per se. In this regard, by way of example, putting cold water into a pool where the body of water has a higher temperature than the cold water will result in the temperature near the introduction of the cold water being lower than it locations elsewhere from the pool, even though the cold water is constantly being diffused throughout the pool. Indeed, plot B of FIG. 12 can represent this phenomenon, or, in another scenario, the impedances can be elevated at many if not all locations along the array, but the most pronounced impedance increase could be at the location proximate the trauma.

By utilizing any of the various known techniques to correlate location electrodes and an electrode array with the local anatomy of the cochlea (e.g., by electrode wetting, by counting the number of electrodes that have been inserted into the cochlea or the number of electrodes that are not inserted into the cochlea, and thus determining how far the electrode array has been inserted into the cochlea, and thus the relative location of various electrodes from the entrance point into the cochlea, by imaging techniques, impedance techniques, etc.), the location of the trauma can be identified by identifying the electrodes experiencing the impedance increase.

It is noted that in at least some exemplary embodiments, techniques are utilized to evaluate whether the increased impedances due to blood flow or due to some other phenomenon, such as, by way of example only and not by way of limitation, those particular electrodes of interest being closer to the modiolus wall of the cochlea relative to other electrodes, an open circuit in the implant, etc. Accordingly, in some exemplary embodiments, the action of determining the presence or absence of trauma is combined with other techniques to evaluate the underlying cause of the impedance increase to increase the likelihood that the impedance increase is a result of trauma and not some other physical phenomenon.

In view of the above, being that in an exemplary embodiment, there is a method that includes determining that trauma has occurred, analyzing a change in measured electrical properties to identify a location along the electrode array of the measured electrical properties, and determining a location of the trauma within the cochlea based on location along the electrode array.

Figure 17:
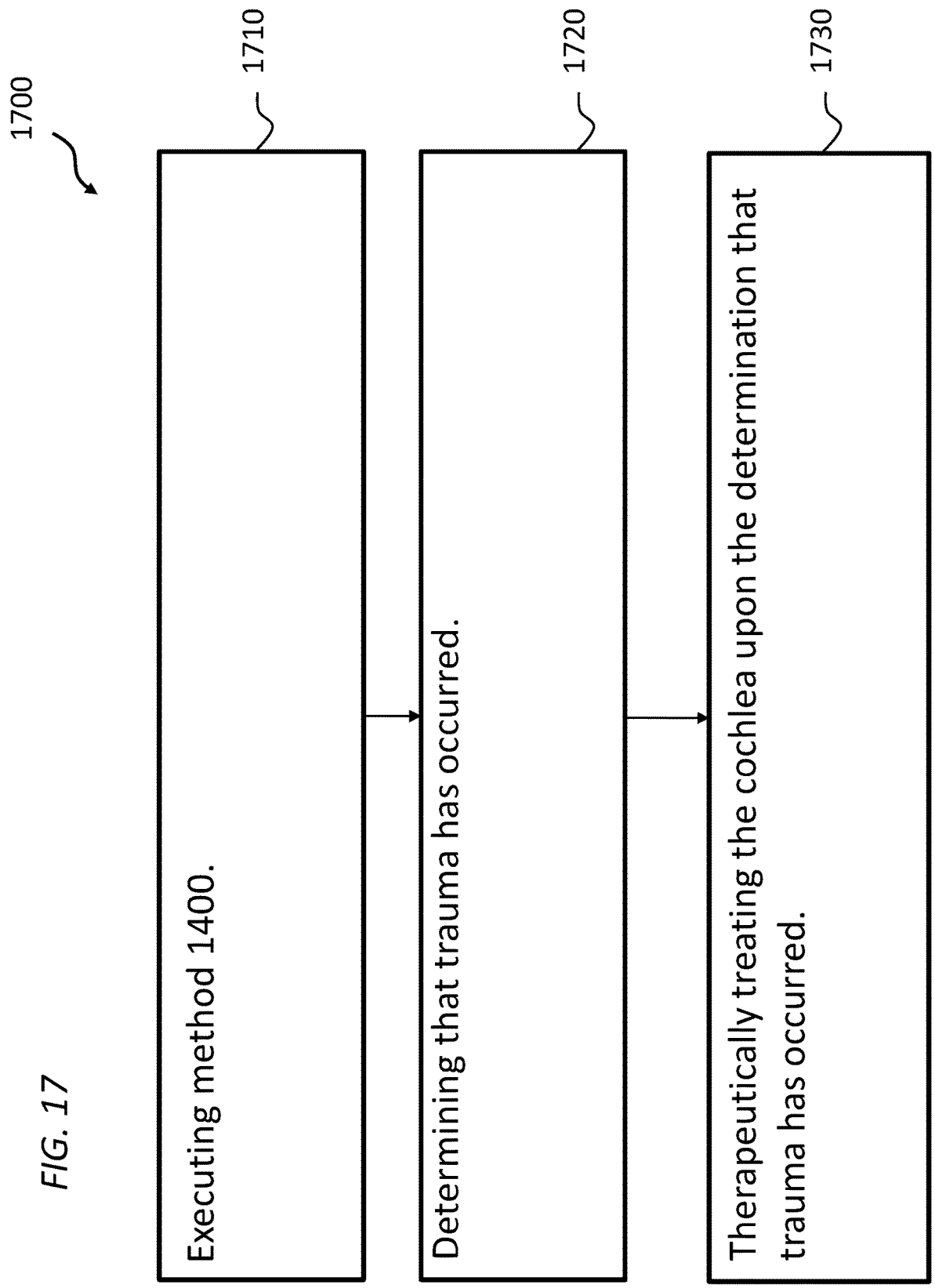

FIG. 17 presents another exemplary algorithm for an exemplary method, method 1700, which includes method action 1710 and method action 1720, which respectively include executing method 1400 and determining that trauma has occurred. Method 1700 also includes method action 1730, which includes therapeutically treating the cochlea upon a determination that trauma has occurred.

In an exemplary embodiment, method action 1730 is executed by mitigating an inflammatory response, where, once blood is detected in the cochlea, a series of actions are undertaken to at least attempt to remove the contaminant (blood/clot). Alternatively, and/or in addition to this, especially if such is unsuccessful, actions are taken to treat the cochlea locally with a drug agent that is configured to minimize or interrupt any inflammatory cascade that leads to the eventual fibrosis. By way of example only and not by way of limitation, method action 1730 can be achieved by one or more or all of the actions:

a. Flushing the cochlea with a saline solution using a fine catheter, or the electrode array itself (via an electrode lumen with exiting hole at the apex of the array, or any other device or system that can have utilitarian value.
b. Bulk impedances are again measured to determine if the presence of the blood or blood clot has been removed successfully, and a comparison between these new readings can be made to other data (for example, the impedance between electrodes for a saline solution can be known (either based on analytic or empirical prior evaluations, and/or based on the fact that as the saline is inserted into the cochlea, the saline will eventually overwhelm the blood, and thus the saline will be a driver of impedance values until the blood begins to take a more dominant role)).
c. In the event blood or clots remain, either in full or in part thereof, a pharmacological intervention is undertaken. Here a measured quantity of drug agent can be released into the cochlea using methods such as charge activated elution or catheter connected to a pump, or any other therapeutic treatment, such as a systemic treatment, can be utilized.

It is noted that the above therapies can have utilitarian value with respect to preserving residual hearing. In this regard, the blood introduction can be something that leads to fibrous tissue growth or other growth of tissue in the cochlea that ultimately reduces the amount of residual hearing the recipient can have or otherwise retain after the cochlear implant electrode array is implanted into the cochlea. In this regard, recipients of cochlear implants can sometimes have residual hearing at the low and medium frequencies. It is the higher frequencies that a recipient can have problems hearing which could result in a utilitarian value of a cochlear implant. Accordingly, by identifying the presence of blood in the cochlea according to the teachings detailed herein and/or variations thereof, and taking actions or otherwise at least accounting for such, exemplary embodiments include improving the percentage chance that the recipient will retain at least 30, 40, 50, 60, 70, 80, 90 or 100 percent of his or her residual hearing that is present one week after the insertion of the electrode array 3 or 4 or 5 or 6 or 7 or 8 or 9 or 10 or 11 or 12 months after the insertion of the electrode array by at least 30, 35, 40, 45, 50, 55, 60, 65, 70, 75, 80, 85, 90, 95 or 100%, relative to that which was the case in the absence of implementing the methods detailed herein, all other things being equal.

In view of the above, it is to be understood that in some exemplary embodiments, the action of measuring an electrical property(s) at a location in the cochlea resulting from the induced current flow at the plurality of different temporal locations is part of an action of measuring respective electrical properties at a plurality of locations in the cochlea using four point impedance measurements, the plurality of locations corresponding to locations of, respectively, at least X electrodes of the electrode array, where X can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 3, 37, 38, 39, or 40 or more. The method further includes the action of determining whether or not trauma has occurred based on a change between the measured electrical properties from the first temporal location to the second temporal location includes identifying a change in impedance between at least some neighboring electrodes of the at least X electrodes. In an exemplary embodiment, the aforementioned method can further include identifying a location of the trauma based on a comparison of the change in impedance between groups of the at least some neighboring electrodes.

Figure 18:
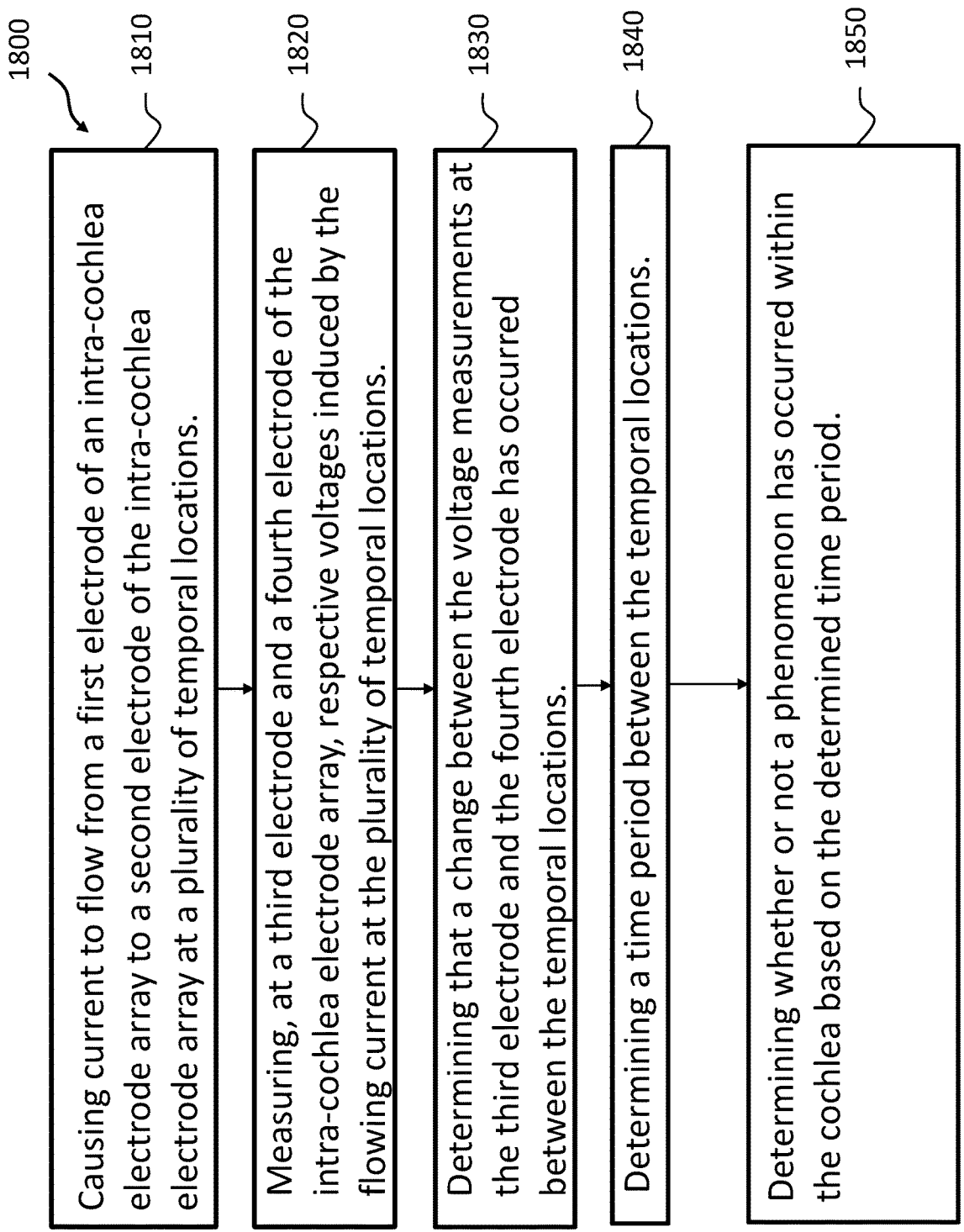

FIG. 18 presents an exemplary algorithm for another exemplary method, method 1800, which includes method action 1810, which includes causing current to flow from a first electrode of an intra-cochlea electrode array to a second electrode of the intra-cochlea electrode array at a plurality of temporal locations, and method action 1820, which includes measuring at a third electrode and a fourth electrode of the intra-cochlea electrode array, respective voltages induced by the flowing current at the plurality of temporal locations. Collectively, method actions 1810 and 1820 can be executed utilizing, for example, a four point impedance measurement scheme.

Method 1800 also includes method action 1830, which includes the action of determining that a change between the voltage measurements at the third electrode and the fourth electrode has occurred between the temporal locations, and method action 1840, which includes determining a time period between the temporal locations. This is followed by method action 1850, which includes determining whether or not a phenomenon has occurred within the cochlea based on the determined time period. By way of example only and not by way of limitation, if the time period is within a few seconds, it might be determined that the changes are based on the normal reaction when an electrode array is being moved into the cochlea. By way of example only and not by way of limitation, if the time period is within a few minutes, it might be determined that the changes are based on a true phenomenon that has occurred within the cochlea.

Consistent with the teachings detailed above, in an exemplary embodiment, the phenomenon is blood entry into the cochlea. In an exemplary embodiment, the phenomenon is trauma to the cochlea due to electrode array insertion. In an exemplary embodiment, the phenomenon is trauma that results during a period of time starting with the time that the first electrode is fully inserted into the cochlea and ending at or after or before electrode 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 3, 37, 38, 39, or 40 (if the electrode array has such number, and if not, reduced accordingly). It is noted that the aforementioned temporal locations noted above can be locations within or bound by this aforementioned time. It is also noted that in an exemplary embodiment, the first and/or the second or any other temporal location can be Z long, where Z is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 3, 37, 38, 39, 40, 41, 42, 43, 44, 45, 46, 47, 48, 49, 50, 51, 52, 53, 54, 55, 56, 57, 59, 60 seconds, or minutes or hours or days (or combinations thereof (e.g., 2 days, 8 hours and 10 minutes) after any of the events herein that would begin a temporal period, or any value or range of values therebetween in 1 second increments). In some embodiments, the determined time period is a period between about (which includes exactly) Z and about Z (where the second Z is larger than the first Z, such as 1 to about 2, 2.5, 3, 3.5, 4, 4.5, 5, 5.5, or 6 minutes), and the method further includes determining that the phenomenon has occurred based on that time period. It is noted that the beginnings and/or ends of the time period need not be keyed to a distinctive event or occurrence. These values can be values where, at the end of a given time period, statistically speaking, if certain things are present, certain things can be inferred, irrespective of the fact that the certain things could be present prior to the end of the time period or the beginning of the time period.

In an exemplary embodiment, the change in voltage measurements results from an increase in impedance between the electrodes and the determined time period is a period between about Z and about Z (about 1 to about 2, 2.5, 3, 3.5, 4, 4.5, 5, 5.5, or 6 minutes, for example), and the method further includes determining that the phenomenon has occurred based on that time period.

In an exemplary embodiment, the determined time period can be longer than Z, and the method further includes determining that the phenomenon has not occurred based on the determined time period, where Z could be about 3.5, 4, 4.5, 5, 5.5, 6, 6.5, 7, 7.5, 8, 8.5, 9, 9.5, 10, 11, 12, 13, 14, 15, 16, 17, 18, 19, or 20 minutes. In some embodiments, the phenomenon is blood entry into the cochlea.

In an exemplary embodiment, the change between the voltage measurements at the third electrode and the fourth electrode is a change that is indicative of fibrous tissue growth within the cochlea if the temporal period was longer than a value of Z (e.g., 1, 2, 3, 4, 5, 6, 7, 8, 9, 10, 11, 12, 13, 14, 15 days, or weeks). The method further includes determining that insertion trauma has occurred because the determined time period is less than Z (e.g., 1, 2, 3, 4, 5, 6, 7, 8, 9, 10, 11, 12, 13, 14, 15 seconds, or days). That is, by way of example only and not by way of limitation, plot B of FIG. 12 can, for all intents and purposes, look like what would occur as a result of fibrous tissue growth (or would be difficult if not impossible to distinguish therefrom). The difference is that the plot B of FIG. 12 exists at a temporal location where fibrous tissue did not have time to grow. In this regard, by evaluating the time period, one can distinguish between phenomena. For example, if the time period is more than 3 or 4 or 5 or 6 or 7 or 8 or 9 or 10 or 11 or 12 or 13 or 14 or 15 minutes or more, in at least some exemplary embodiments, the phenomenon is likely something other than blood in the cochlea or something other than trauma resulting from the insertion process of the electrode array, etc., and thus the teachings detailed herein include method of determining such.

In an exemplary embodiment, method 1800 further includes the action of determining that trauma has occurred, wherein the phenomenon is trauma to the cochlea due to electrode array insertion (as opposed to post insertion trauma that occurs after the electrode array is fully inserted, or after the skin is closed during surgery, etc.), and the method further includes determining a location of the trauma within the cochlea based on the location of the third electrode and the forth electrode relative to other electrodes where a change in voltage measurements between such is less than that between the third and the fourth electrodes during the determined time period. In an exemplary embodiment, the difference in voltage measurements is such that the lower voltage is no more than about 5, 6, 7, 8, 9, 10, 15, 20, 25, 30, 40, 50, 60, 70, 80, or 90 percent of the higher voltage, or any value or range of values therebetween in 1% increments).

Figure 19:
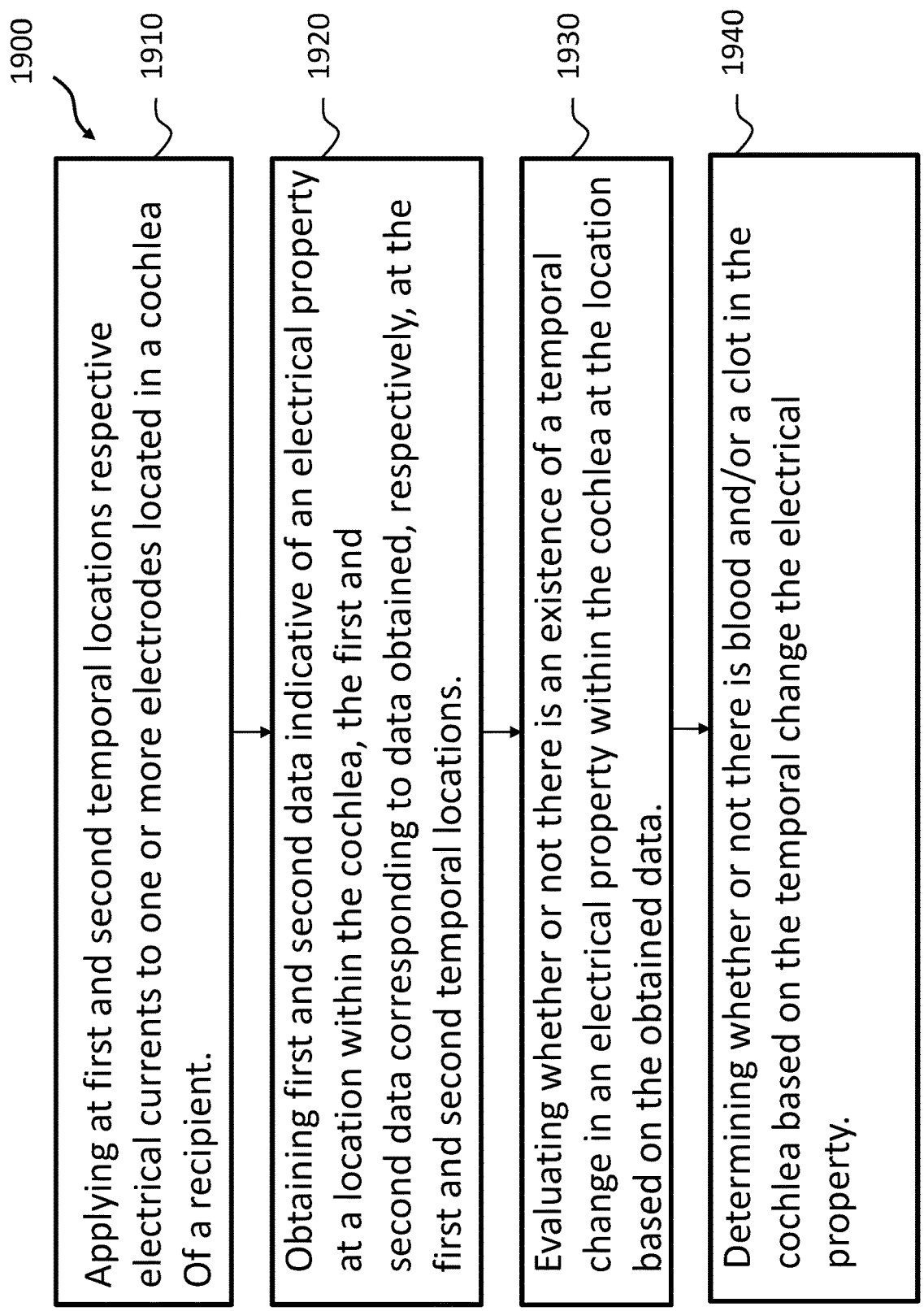

FIG. 19 presents an algorithm for an exemplary method, method 1900, which includes method action 1910, which includes the action of applying at first and second temporal locations respective electrical currents to one or more electrodes located in a cochlea of a recipient. This can be done by applying electrical currents to only one group of a source and sink at a first temporal location and then applying electrical currents to that group or another group of a source and a sink without applying current to any other electrodes. This can be done by applying electrical currents to more than only one group of a source and a sink, such as by way of example only and not by way of limitations, 2 groups, 3 groups, 4, 5, 6, 7, 8, 9, 10, 11, 12, 13, 14, 15, 16, 17, 18, 19, 20, 21, 22, 23, 24, 25, 26, 27, 28, 29, or 30 or more groups (where the application of electrical current is staggered temporally, but all within the first temporal location) where every group has a source or sink that is different from that of another group, during a first temporal location, and then repeating that at the second temporal location, or using more or less groups or doing a variation of those groups or utilizing completely different groups. Any regime of applying electrical currents to electrodes can be used in some embodiments if enabled. Note also that in an exemplary embodiment, method action 1910 can be executed utilizing one intracochlear electrode and one extra cochlear electrode, or more than one intracochlear electrode while utilizing the extra cochlear electrode as part of all the groups, and so on. Method 1900 also includes method action 1920, which includes obtaining first and second data indicative of an electrical property at a location within the cochlea (in some embodiments, this is more generically at a location away from the electrodes—which could be the 4 point impedance regime), the first and second data corresponding to data obtained, respectively, at the first and second temporal locations. By way of example only and not by way of limitation, in an exemplary embodiment, the result of method action 1920 can result in the plots A and B of FIG. 12. Method 1900 also includes method action 1930, which includes evaluating whether or not there is an existence of a temporal change in an electrical property within the cochlea at the location based on the obtained data (note that this is no exclusive to only one property/one change—as long as the evaluation includes an evaluation of a change in one property, such as covered). Method 1900 also includes method action 1940, which includes determining whether or not there is blood and/or a clot in the cochlea based on the temporal change in electrical conductivity. Method action 1940 can be executed by evaluating the change in impedances at the location between the first temporal period and the second temporal period.

As noted above, method 1900 includes obtaining electrical properties at a location within the cochlea. It is noted that this does not exclude obtaining electrical properties at more than one location within the cochlea. As long as there is one location within the cochlea where the properties are obtained, and that is consistent (within capabilities of the art) between the first and second temporal periods, such as encompassed by this feature. As will be detailed below, in an exemplary embodiment, a location of interest can be the first basal turn, and in an exemplary embodiment, method 1900 includes analyzing the change in an electrical property at that location. The method can include evaluating changes in properties at other locations as well.

Figure 20:
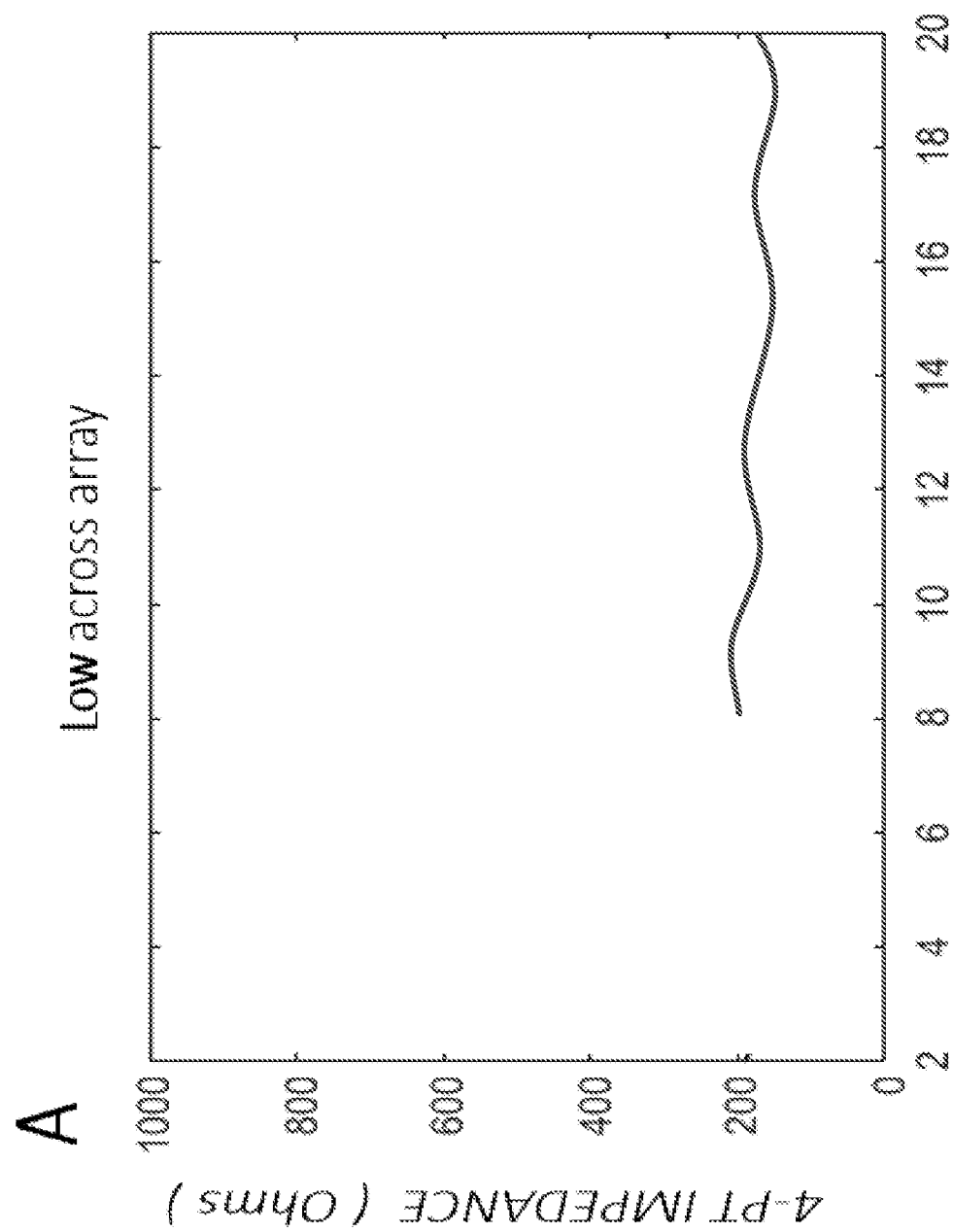
FIGS. 20-28 present exemplary data according to some embodiments.
Figure 21:
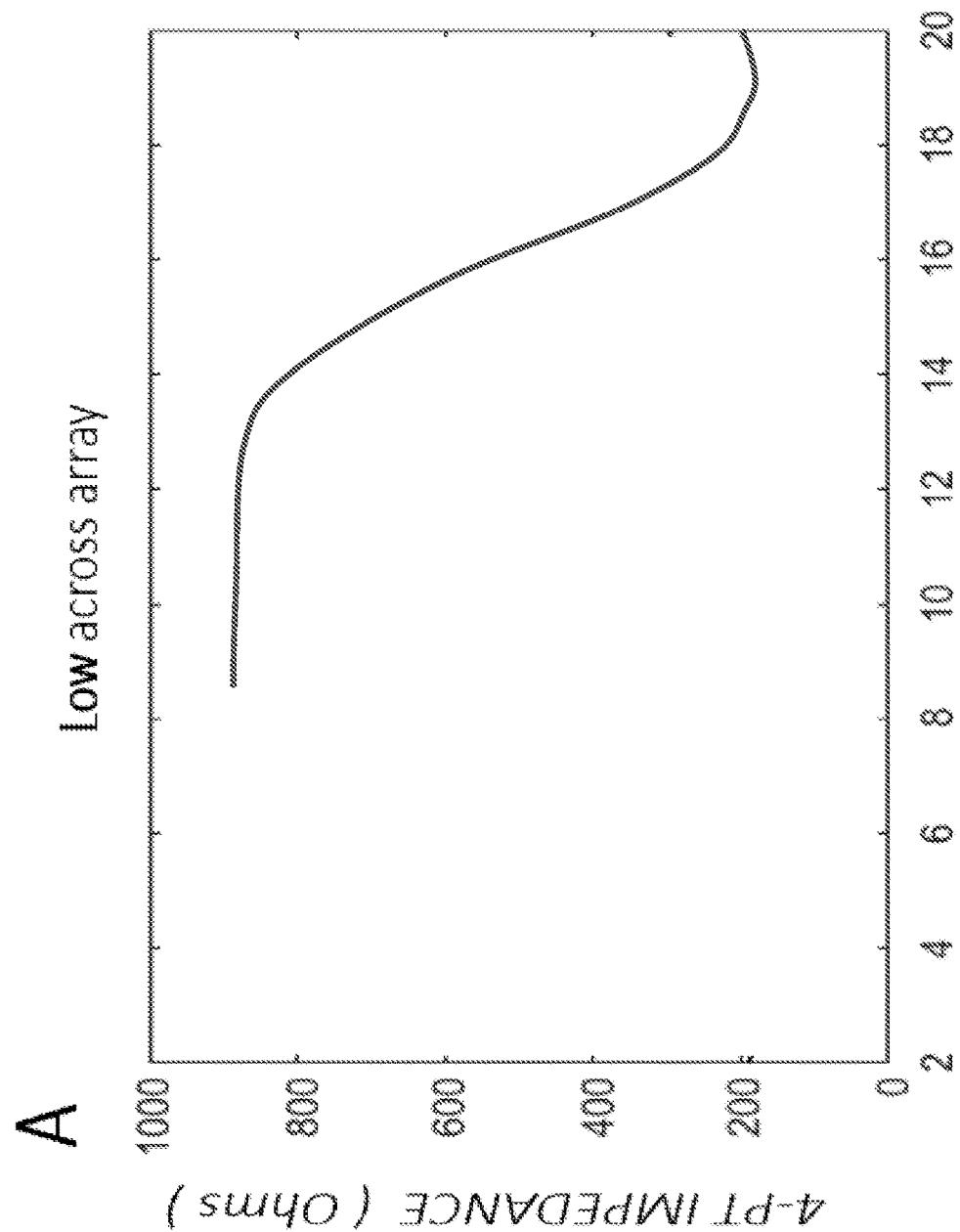
Figure 22:
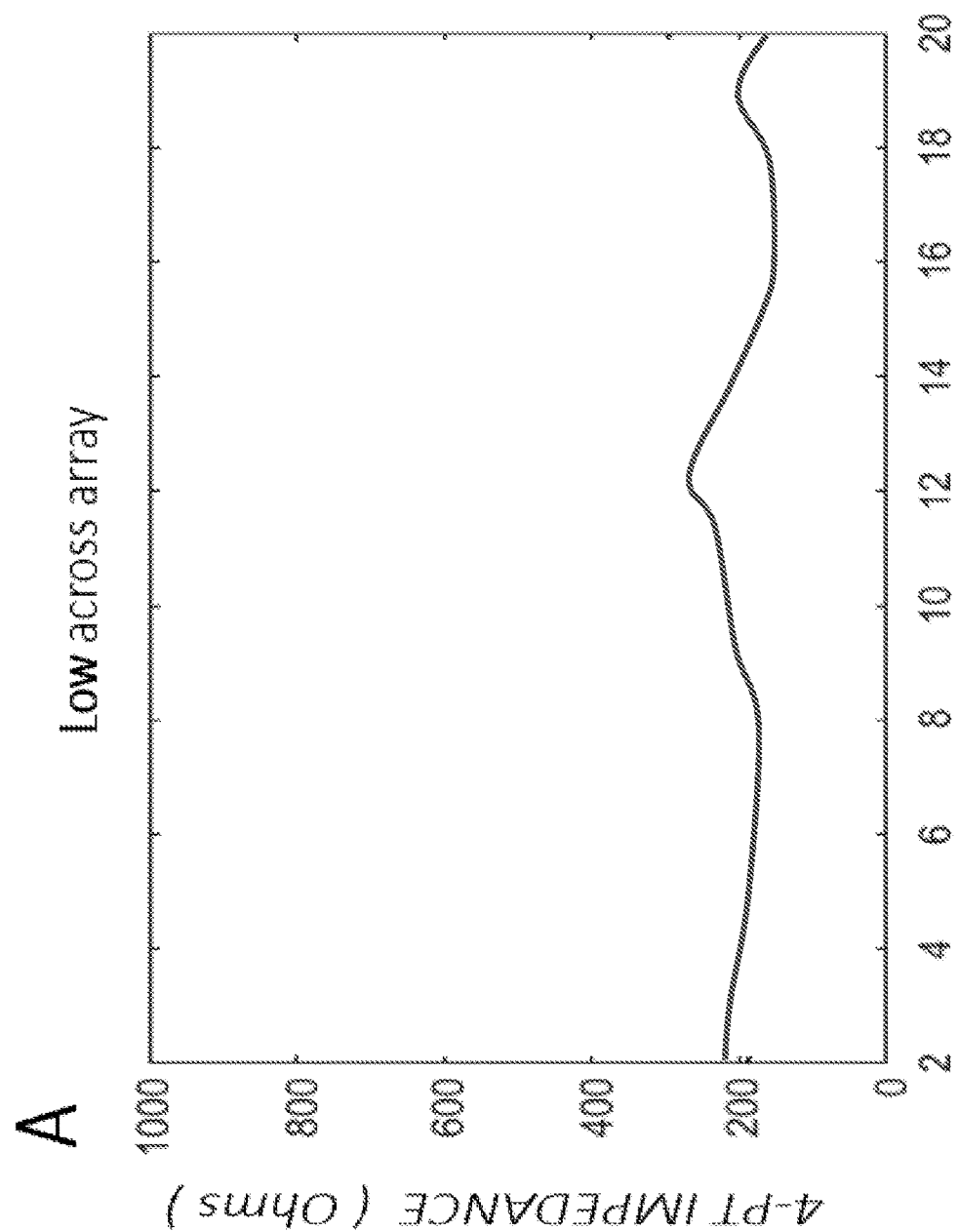
Figure 23:
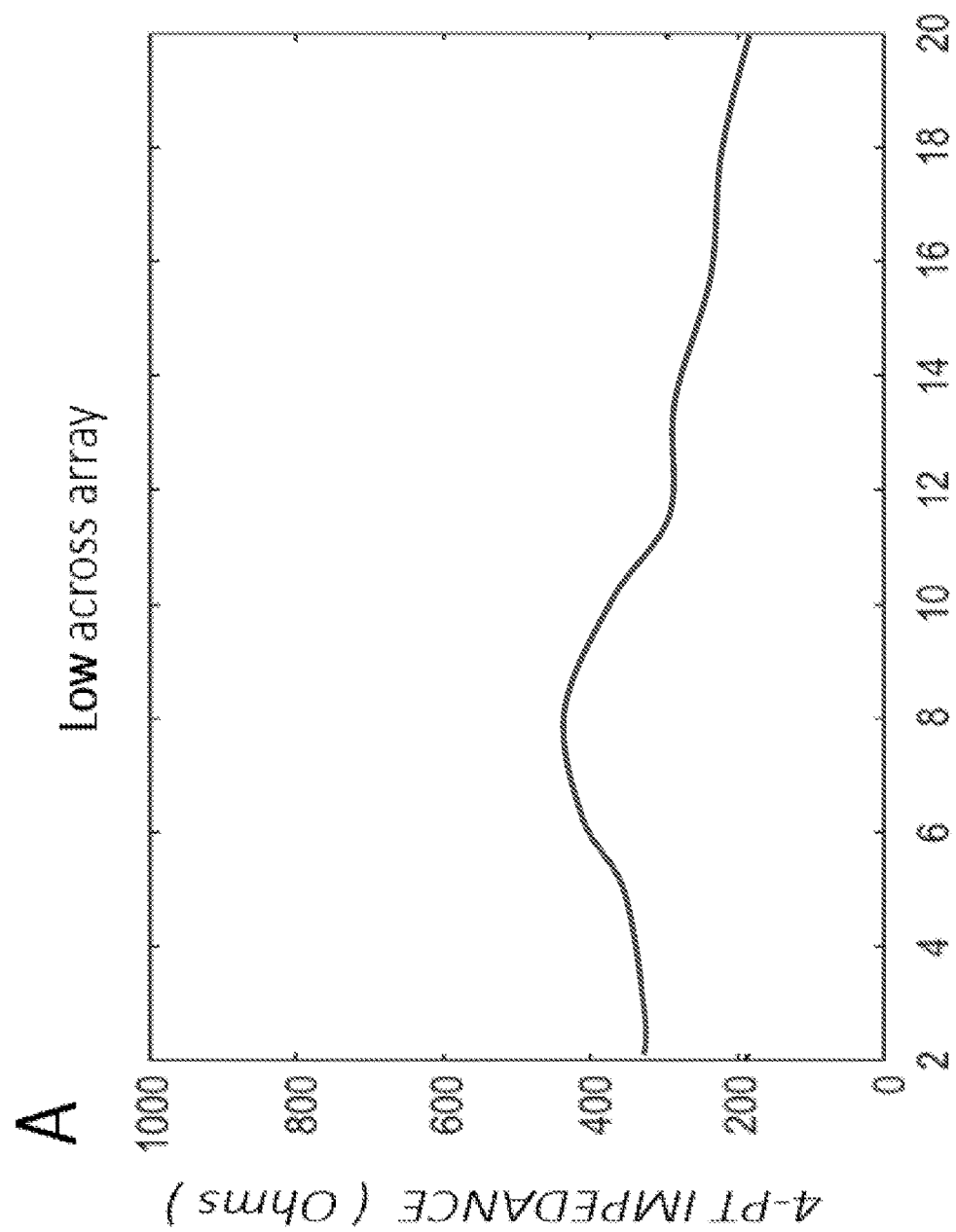
Figure 24:
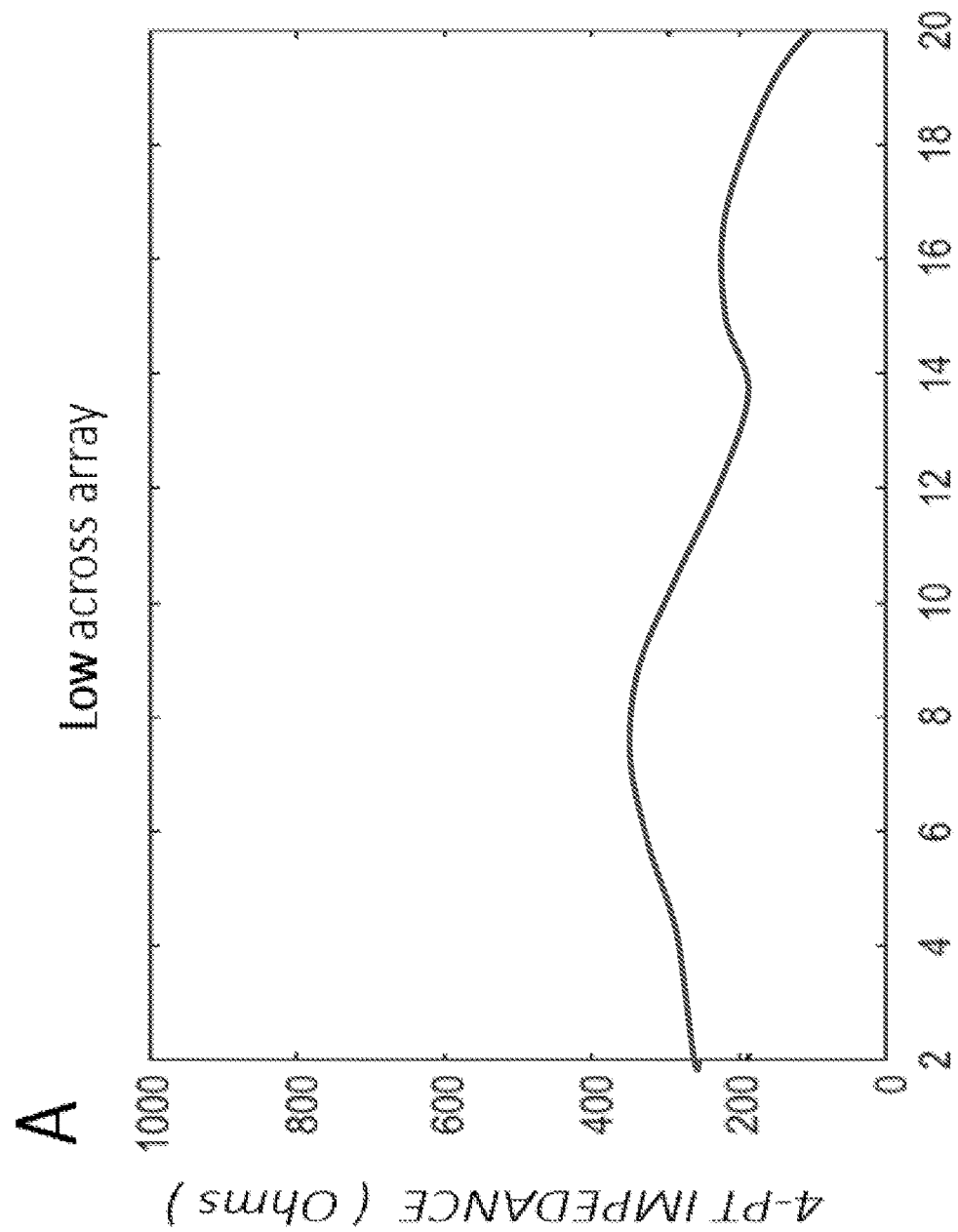
Figure 25:
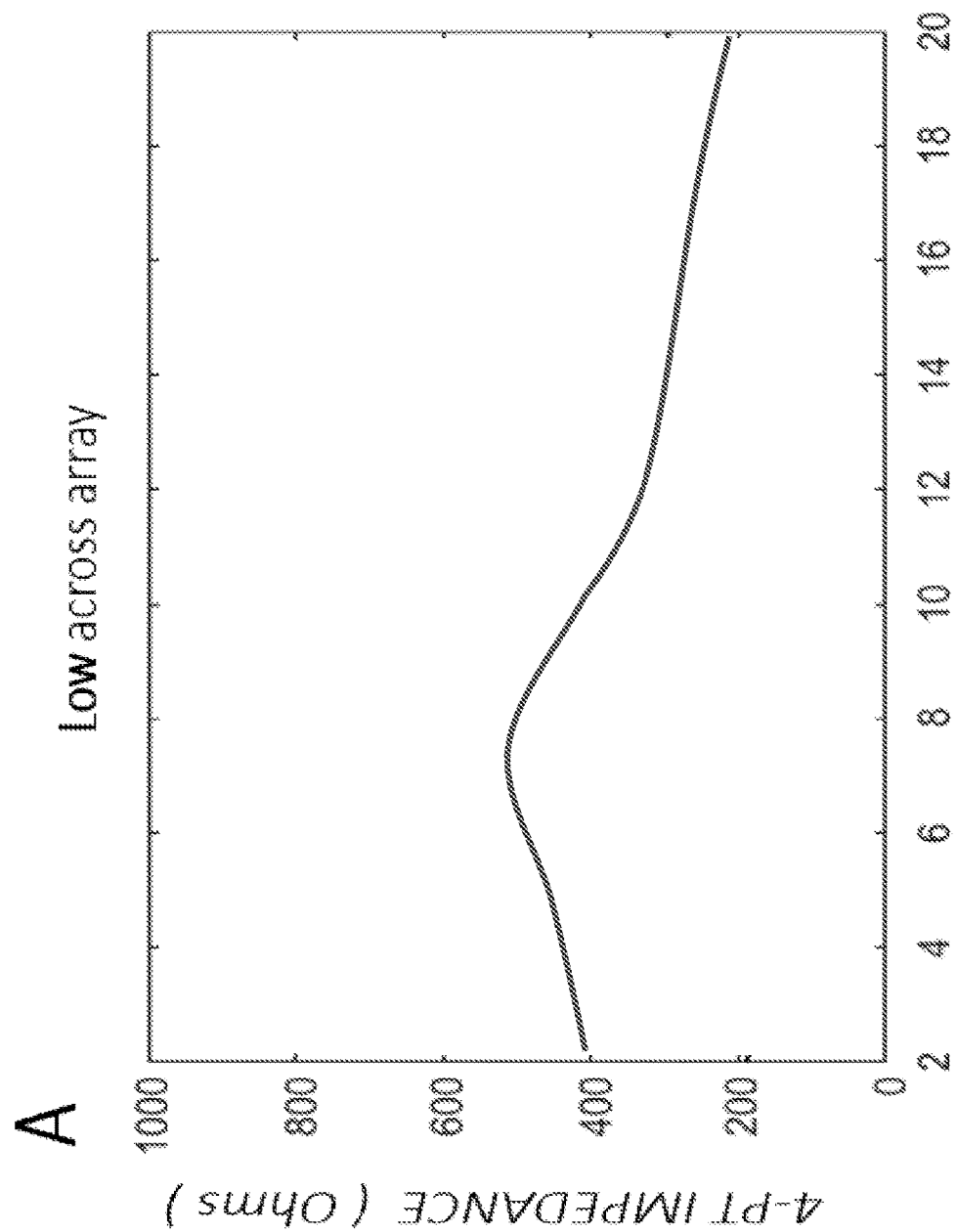
Figure 26:
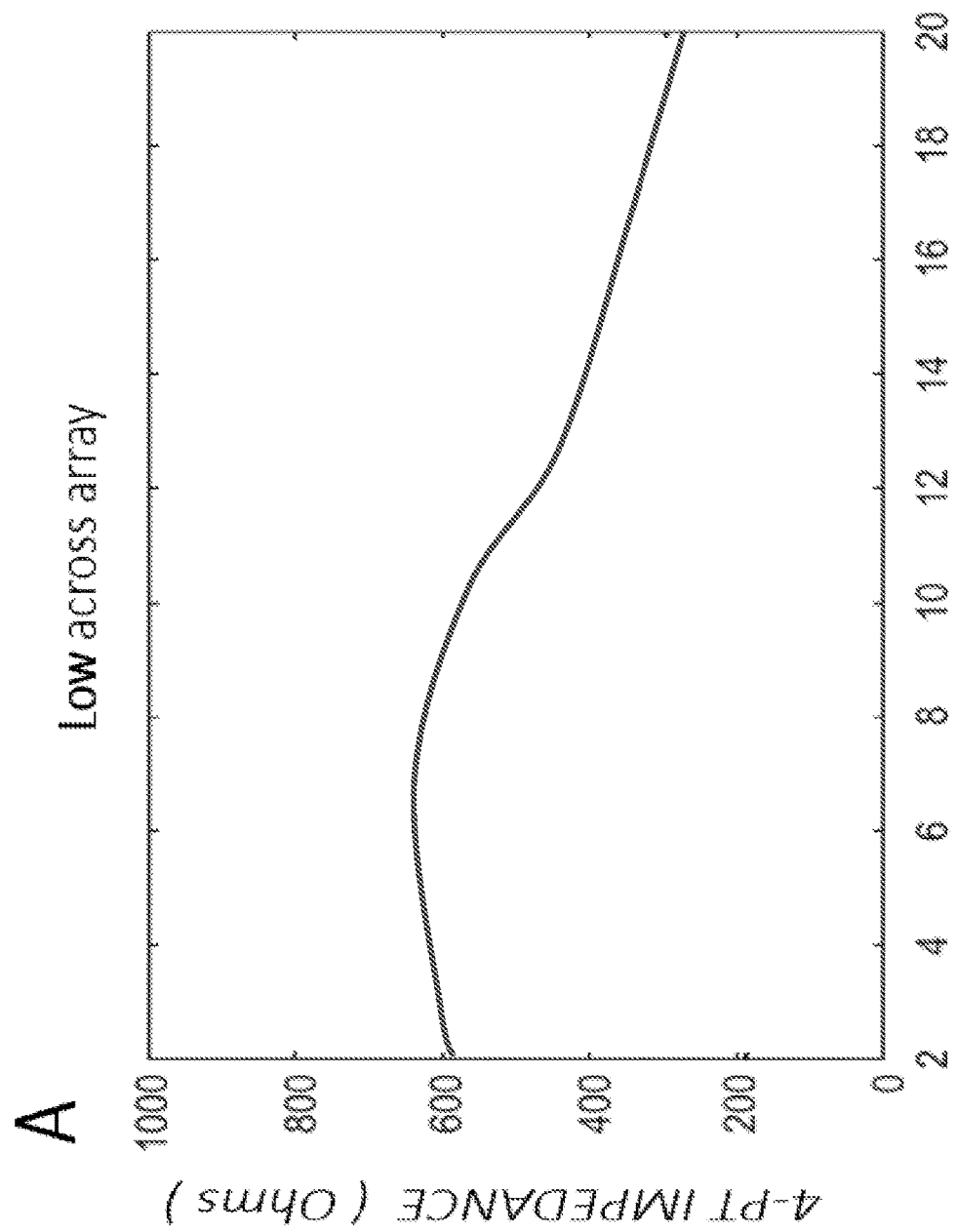
Figure 27:
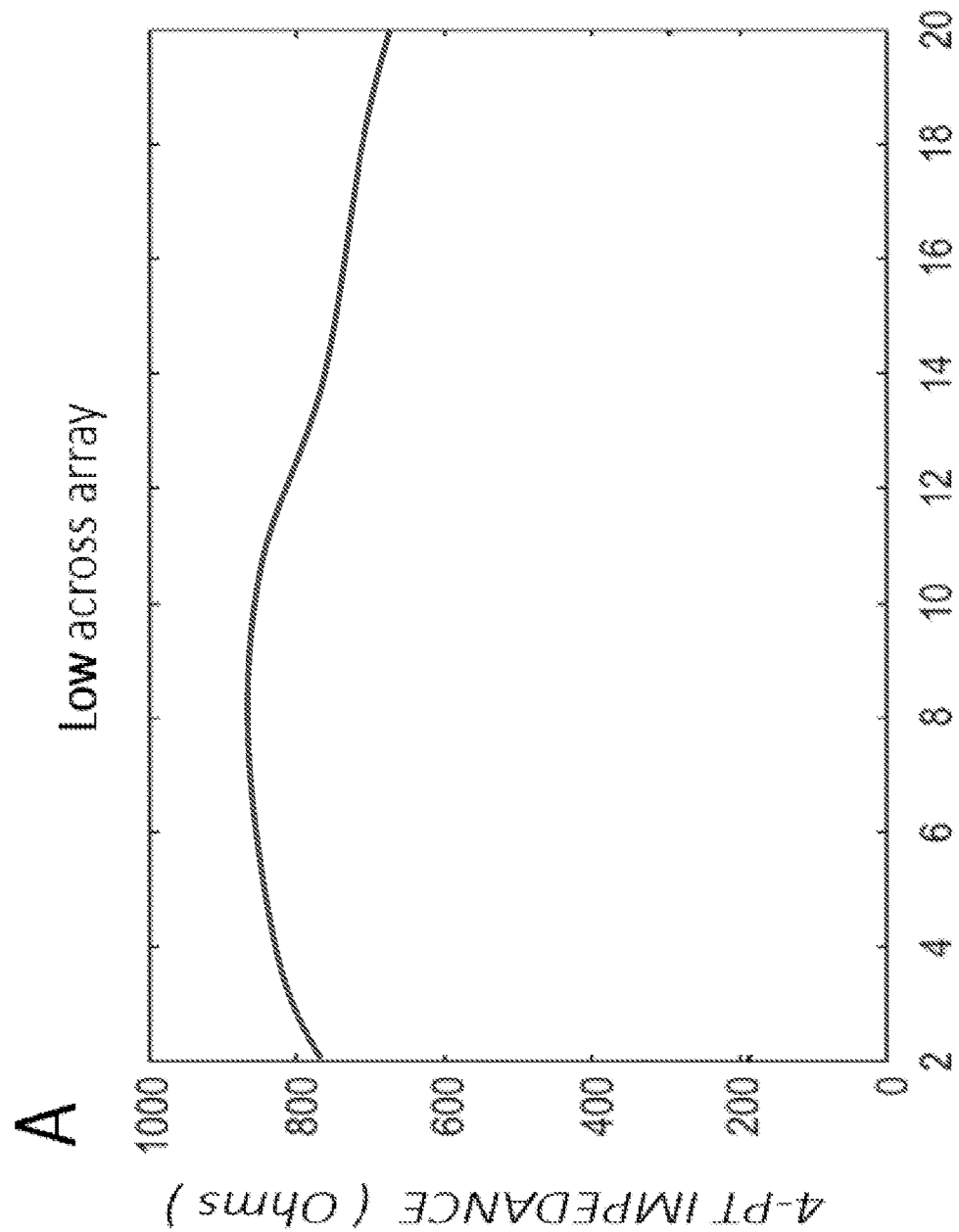

Briefly, as will be explained in greater detail below, in some exemplary embodiments, method 1900 and/or the other methods detailed herein are directed towards focusing only a limited number of locations within the cochlea relative to the entire cochlea. Again, in an exemplary embodiment, the location of the first basal turn can be the focus of attention. In this regard, in an exemplary embodiment, as the electrodes are moved to the location within the cochlea, the pertinent electrodes can be energized and the pertinent read electrodes can be utilized, such as the read electrodes at the location/adjacent to the location of interest, and a data set can be developed for that location. By way of example only and not by way of limitation, in an exemplary embodiment, the first temporal location can be a location where the most apical electrode, electrode 22, first reaches the basal turn of the cochlea to the where the most basal electrode that reaches the basal turn (e.g., electrode 8 or 9 or 10 or 11 or so) has indeed reached the basal turn (e.g., electrode array is fully inserted). FIG. 20 represents an exemplary plot A resulting from the first temporal location being the location where the most apical electrodes, electrodes 18-22, first reach the basal turn of the cochlea, where subsequent temporal locations correspond to the other electrodes first reaching the basal turn. In this regard, each data point represents a different temporal location. In an exemplary embodiment, the first temporal location can correspond to the data points associated with electrode 20 and the second temporal location can correspond to the data point associated with electrode 9. As can be seen, the electrical property does not change in a significant matter, and thus a determination can be made that there is no blood at the location or otherwise blood in general in the cochlea. Conversely, FIG. 21 represents another plot based on the same temporal locations except that as the electrode array is being inserted into the cochlea, it is induces a laceration in the wall and blood flows into the cochlea at the first basal turn. Accordingly, as the temporal locations progress, and thus the various electrodes come into the location corresponding to the basal turn, the impedance increases as time progresses until it levels off. In this regard, the comparison would reveal that a change of impedance has occurred between the two temporal locations, and thus a determination would be made that there is a blood and/or, plot in the cochlea in general, and at that particular location.

Note that the scenario of FIG. 21 represents a relatively large cut where relatively large amounts of blood into the cochlea in a period of time (less than or equal to the time that it takes to get the electrode array fully inserted into the cochlea—note that in this exemplary embodiment, because the location of interest is the first basal turn, the electrodes basal of the first basal turn are not utilized, although in other embodiments, these electrodes can be utilized as well). In an exemplary embodiment where FIG. 21 represents data obtained as the given electrodes pass by the given location (i.e., the data of FIG. 21 represents a single spatial location over various temporal locations), as the blood begins to flow from the laceration, there will be more blood at that particular location, hence the increase from electrodes 17 to electrodes 9 as those electrodes reach that location. Conversely, FIGS. 20 and 21 can represent a method where the electrical properties are obtained at many different locations over to temporal periods. In this regard, in an exemplary embodiment, FIG. 20 can correspond to that which results from taking the four point impedance measurements at a temporal location immediately or close thereto after full insertion (e.g., within 1 or 2 or 3 or 4 seconds), and FIG. 21 can correspond to that which results from taking the four point impedance measurements at a temporal location 2 or 3 or 4 or 5 or more minutes after full insertion. Thus, electrical properties for approximately 10 or 11 locations in the cochlea are obtained at both of the temporal locations, and the temporal change in the electrical property at those locations can be seen. Here, some locations do not show a significant change in resistivity/productivity, while others do show such a change. Based on such an analysis, one can determine that there is blood and/or a clot in the cochlea.

In any event, referring back to method 1900, in an exemplary embodiment, the temporal change is a rapid change in impedance within the cochlea. In an exemplary embodiment, by way of limitation, and impedance change within the cochlea can correspond to an increase of 50, 75, 100, 125, 150, 175, 200, 250, 300, 350, 400, 450, 500, 550, 600, 700, 800, 900 or more percent over that temporal period, and depending on the increase, a determination can be made that there is blood and/or a clot in the cochlea (or trauma, etc.). The time between the two temporal locations can be any of the Z values detailed above depending on the embodiment.

In an exemplary embodiment where the action of determining whether or not there is blood and/or a clot in the cochlea includes determining that there is blood in the cochlea, method 1900 can further include determining a location of an origin of the blood in the cochlea. By way of example only and not by way of limitation, referring to FIG. 21, because the impedances highest at about the location of electrode 9 or 10, a determination can be made that the origin of the blood in the cochlea is at a location proximate those electrodes. This can be the case based on a scenario where FIG. 21 represents the impedances taken with a stationary electrode two or three minutes etc., after full insertion, or where FIG. 21 represents impedances taken as the electrodes pass by the location where the blood is entering into the cochlea.

In an exemplary embodiment, the action of determining whether or not there is blood and/or a clot in the cochlea includes determining that there is blood in the cochlea, and method 1900 further includes determining a location of an origin of the blood in the cochlea based on a comparison of the second data to at least third data indicative of electrical properties at a spatial location away from the location, the third data being obtained at effectively the same time as the second data, wherein the second data is obtained after the first data. In an exemplary embodiment, such as where FIG. 21 represents data obtained at different temporal locations for each of the data points, a comparison can be made between the data obtained at the location at the $16^{th}$ electrode, which would be the third data, and a comparison can be made to the data obtained at the $9^{th}$ or $10^{th}$ or $11^{th}$ or $12^{th}$ electrode etc., and thus a determination can be made the difference in the impedances indicates that the location of the origin of blood in the cochlea is at a location proximate the $9^{th}$ or $10^{th}$ or $11^{th}$ or $12^{th}$ electrode etc.

In an exemplary embodiment of utilizing impedances obtained at read electrodes, the location of trauma or otherwise blood entry into the cochlea can be considered to be the section of the cochlea wall that is closest to the read electrodes that indicate the heightened impedances.

In an exemplary embodiment of method 1900, the action of applying at first and second temporal locations respective electrical currents to the one or more electrodes located in a cochlea of a recipient is executed using a cochlear implant electrode array four point impedance technique. In an exemplary embodiment, the temporal change is a change in impedance within the cochlea, and method 1900 further includes evaluating the change in the impedance relative to a time period (e.g., any of the Z values above, as applicable) and the action of determining whether or not there is blood and/or a clot in the cochlea includes differentiating between blood and the clot based on the evaluated change relative to the time period. In an exemplary embodiment, a relatively longer time period will indicate a clot as compared to blood.

In another exemplary embodiment, with respect to method 1900, again where the action of applying at first and second temporal locations respective electrical currents to the one or more electrodes located in a cochlea of a recipient is executed using a cochlear implant electrode array four point impedance technique, and where the temporal change is a change in impedance within the cochlea, method 1900 can further include evaluating the change in the impedance, wherein the action of determining whether or not there is blood and/or a clot in the cochlea includes differentiating between blood and the clot based on the change in impedance. In an exemplary embodiment, a relatively larger change in impedance will indicate a clot as compared to blood.

Figure 28:
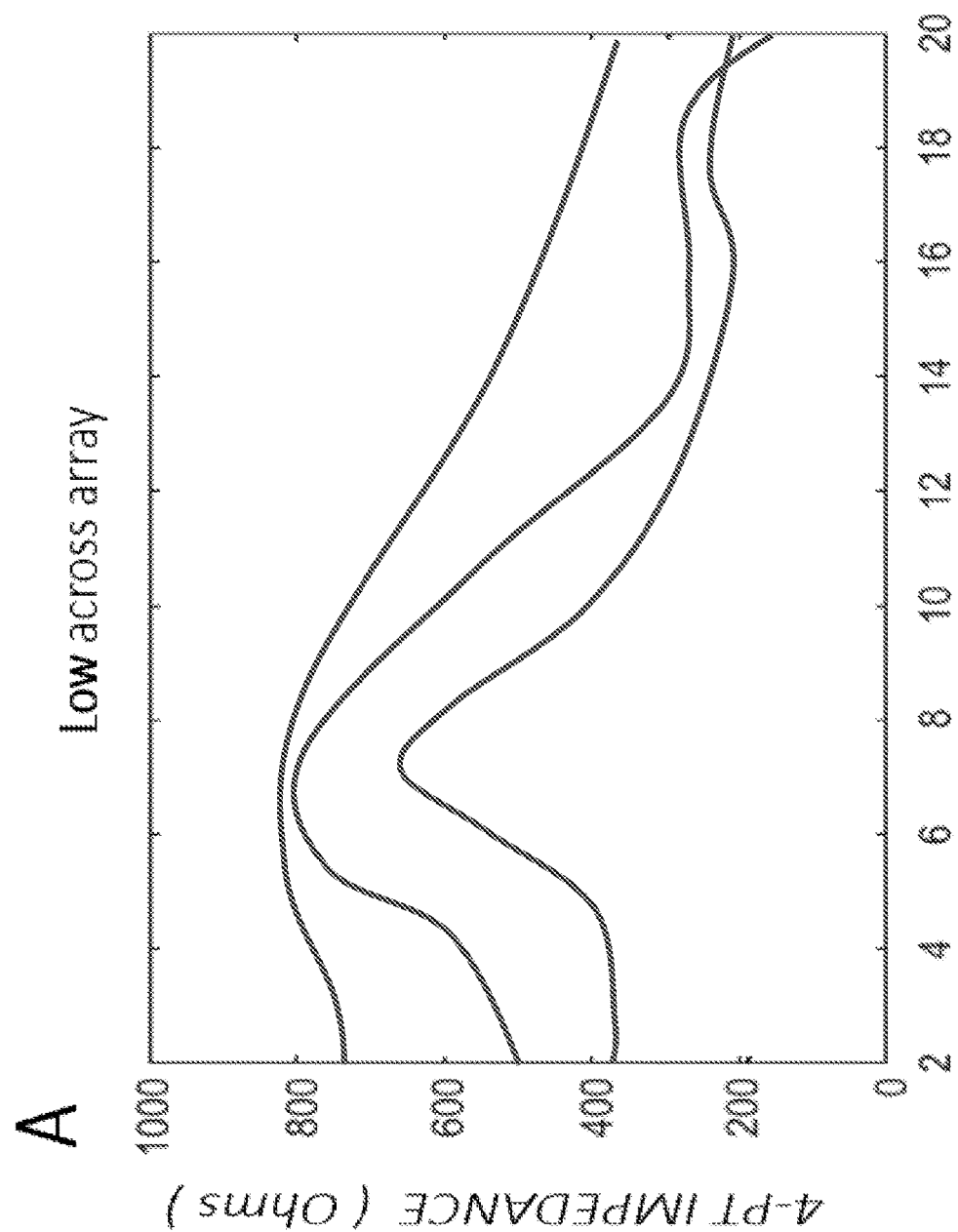

Still further, in an exemplary embodiment of method 1900, the action of determining whether or not there is blood and/or a clot in the cochlea includes determine that there is blood in the cochlea and the method further includes monitoring spread of the blood in the cochlea based on impedance measurements between electrodes inside the cochlea. FIGS. 22-26 respectively present plots of impedances obtained along the electrode array after full insertion at different temporal periods after full insertion, with time progressing from FIGS. 22 to 26. As can be seen, the impedances tend to consistently show a highest level at around electrodes 7 to 10, but over time, the impedances at the other electrodes increases to about the same as those electrodes, indicating the spread of the blood within the cochlea to those other locations, where the origin of the blood is probably around electrodes 7 to 10. It is noted that these plots show a gradual increase over time. In an alternate embodiment, the data near the entry of the blood can show a rapid increase at locations proximate the blood entry location, such as the bottom curve of FIG. 28, and then subsequent increases at that location are less rapid, while the other locations increase at a more rapid rate as the blood diffuses (the three curves represent data obtained at increasing temporal locations (with increasing y-axis value at electrode 2) from that which resulted in the data of FIG. 22). Accordingly, an exemplary embodiment can include evaluating the rate of change of electrical properties at given locations along the electrode array to monitor the spread of blood, and can include comparing the rate of changes to that of other locations etc., to deduce phenomenon occurring in the cochlea.

Figure 29:
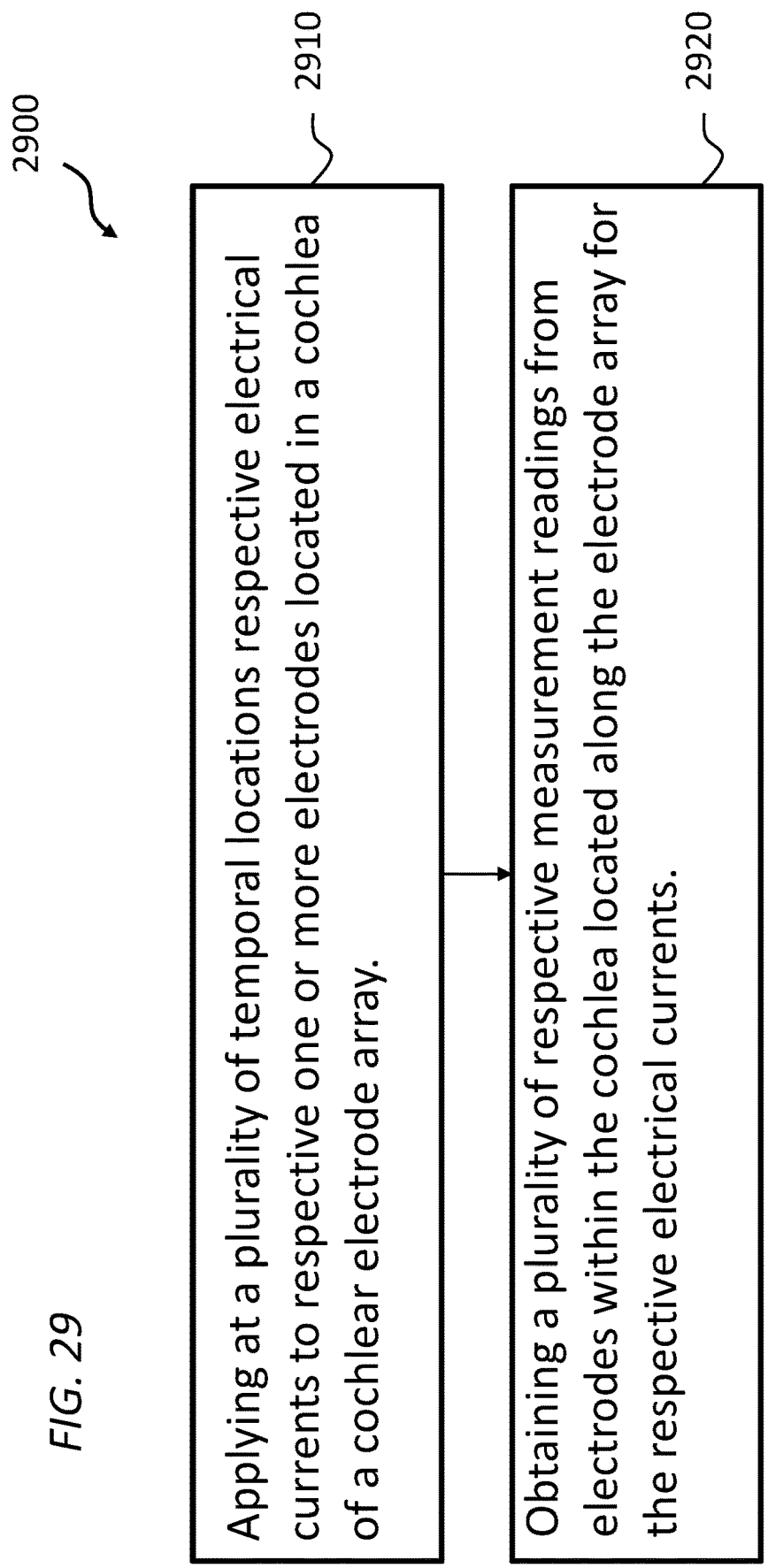
FIGS. 29 and 30 present exemplary algorithms for exemplary methods.

FIG. 29 presents another algorithm for another exemplary method, method 2900, which includes method action 2910, which includes applying at a plurality of temporal locations respective electrical currents to respective one or more electrodes located in a cochlea of a cochlear electrode array, and method 2920 which includes obtaining a plurality of respective measurement readings from electrodes within the cochlea located along the electrode array for the respective electrical currents. In this exemplary embodiment, the method includes moving the electrode array in the cochlea, and the action of obtaining the plurality of respective measurement readings is executed such that the readings are focused at a same location within the cochlea relative to other locations within the cochlea. Again, by way of example only and not by way of limitation, the movement can be the movement of the insertion of the electrode array into the cochlea, and the focusing can be the focus on the first basal turn. Thus, according to an exemplary embodiment, the plurality of temporal locations can be the temporal locations where the read electrodes of the electrode array first become proximate to the location of interest. Again, in an exemplary embodiment, as the electrode array is being inserted in the cochlea, electrodes 22 and 19 can be utilized as the source and sink, and electrodes 20 and 21 can be the read electrodes at a temporal location where electrodes 20 and 21 are the most proximate to the basal turn, and then electrodes 21 and 18 can be utilized as a source and sink, and electrodes 19 and 20 can be utilized as the read electrodes at the temporal location where electrodes 19 and 20 are the most proximate to the basal turn, and then electrodes 20 and 17 can be utilized as a source and sink, and electrodes 18 and 19 can be utilized as the read electrodes at the temporal location where electrodes 18 and 19 by the most proximate to the basal turn, etc. Accordingly, in an exemplary embodiment of method 2900, thus same location within the cochlea is a location at or proximate a basal turn of the cochlea, and/or the method is executed during the electrode array insertion into the cochlea.

In an exemplary embodiment of method 2900, the method is executed during electrode array insertion into the cochlea, and during the period when the electrode array is being driven into the cochlea, with respect to the electrodes of the electrode array, at least effectively only electrodes at or proximate the same location are used as measurement electrodes to obtain the respective measurement readings. By way of example only and not by way of limitation, in an exemplary embodiment, such as where the only location of interest is the basal turn of the cochlea, the measurement electrodes utilize are those that are located proximate or at the basal turn, and the other electrodes are not utilized, at least not effectively (perhaps some instances all of the electrodes are utilized, but the bulk of the data collection is based on only those electrodes that are at or proximate the location). In an exemplary embodiment, more than 20, 25, 30, 35, 40, 45, 50, 55, 60, 65, 70, 75, 80, 85, 90, 91, 92, 93, 94, 95, 96, 97, 98, or 99% of the data collected comes from electrodes that are at or proximate the location with respect to data collected during insertion of the electrode array and/or for a temporal. That extends beyond (including or starts after) full insertion of the electrode array. In an exemplary embodiment, the temporal period can be any of the Z values detailed above from the point where the electrode array first enters the cochlea and/or from the point where the electrode array is fully inserted into the cochlea. It is also noted that the aforementioned percentages can be also applicable to the energized electrodes. That is, the aforementioned percentages can correspond to the percentage of current that is applied to the electrodes at or proximate the location of interest for the aforementioned insertion and/or for the aforementioned time periods. It is noted that in at least some exemplary embodiments, other locations of interest can be included in method 2900. In an exemplary embodiment, effectively only electrodes at or proximate to the same locations or three of the same locations are used as measurement of electrodes, with the aforementioned percentages or qualifiers being applicable thereto in at least some exemplary embodiments.

In an exemplary embodiment, again where method 2900 is executed during electrode array insertion into the cochlea, and during the period when the electrode array is being driven into the cochlea, with respect to the electrodes of the electrode array, other than for neural response detection, at least effectively only electrodes at or proximate the same location are used as measurement electrodes to obtain the respective measurement readings. Some additional details of the neural response detection will be described below (ECoG, and NRT). It is noted that in at least some exemplary embodiments, the aforementioned percentages and qualifiers applied to this embodiment as well.

In an exemplary embodiment, again where method 2900 is executed during electrode array insertion into the cochlea, during the period when the electrode array is being driven into the cochlea, with respect to the electrodes of the electrode array, at least effectively only electrodes at or proximate the same location are supplied with electrical current.

In an exemplary embodiment, the electrodes that are used as read electrodes and/or energized electrodes fall within a distance of no more than 0.5, 0.75, 1, 1.25, 1.5, 1.75, 2, 2.5, 3, 3.5, 4, 5, 6, 7, 8, 9, 10, 11, 12, 13, 14, or 15 millimeters from a line taken normal to a tangent at the beginning of the first basal turn at the lateral wall.

Consistent with the embodiments detailed above with respect to limiting the read electrodes to those at or proximate the given location, in an exemplary embodiment of the method 2900, the electrode array includes at least X plus 5 electrodes (e.g., 6, 7, 8, 9, 10, 11, 12, etc.), the method is executed during electrode array insertion into the cochlea and the action of obtaining a plurality of respective measurement readings from electrodes within the cochlea located along the electrode array for the respective electrical currents is executed for electrodes that become at or proximate the same location as the electrode array is inserted into the cochlea and not doing so for electrodes that are not proximate to the location. In an exemplary embodiment, during insertion of the electrode array, the pattern of utilization of electrodes as read electrodes and/or the pattern of applying electrical current to electrodes is such that the most apical electrodes are first utilized before electrodes basal thereto, and then electrodes basal to the most apical utilized, and so on, without using again electrodes apical to an electrode that is used as a read and/or energized electrode again during insertion.

In an exemplary embodiment, method 2900 further includes the actions of obtaining additional measurement readings from electrodes, whether within the cochlea or not, determining location of the electrode array in the cochlea based on the additional measurements and focusing the readings based on the determined location.

Some other embodiments include a method that includes the action of applying an electrical current to one or more electrodes of an electrode array located in a cochlea of a recipient, obtaining data indicative of impedances between a plurality of groups of two electrodes corresponding respectively to different locations along the electrode array, evaluating electrical conductivity between the respective electrodes of the respective groups, determining the existence of an impedance change between the respective electrodes of the respective groups; and determining a location, density and temporal feature of the impedance change.

Utilizing embodiments based on the timing between changes if any, of the electrical properties can, in some embodiments, reduce or otherwise eliminate or otherwise enable the detection of false positives. In this regard, impedance changes occur for a host of reasons, including, as noted above, fibrous tissue growth, spatial location relative to the cochlea walls, etc. By evaluating changes in impedance based on temporal aspects, a determination can be made that a given impedance change is indeed indicative of trauma to the cochlea in general, and, specifically, the introduction of blood into the cochlea.

It is briefly noted that the term trauma does not include the foreign body response that results from a typical insertion of the electrode array. By way of example only and not by way of limitation, calcification or the growth of fibrous tissue owing to the presence of a foreign body, such as the implant, is not a trauma. Conversely, a laceration inside the cochlea would be trauma.

Figure 30:
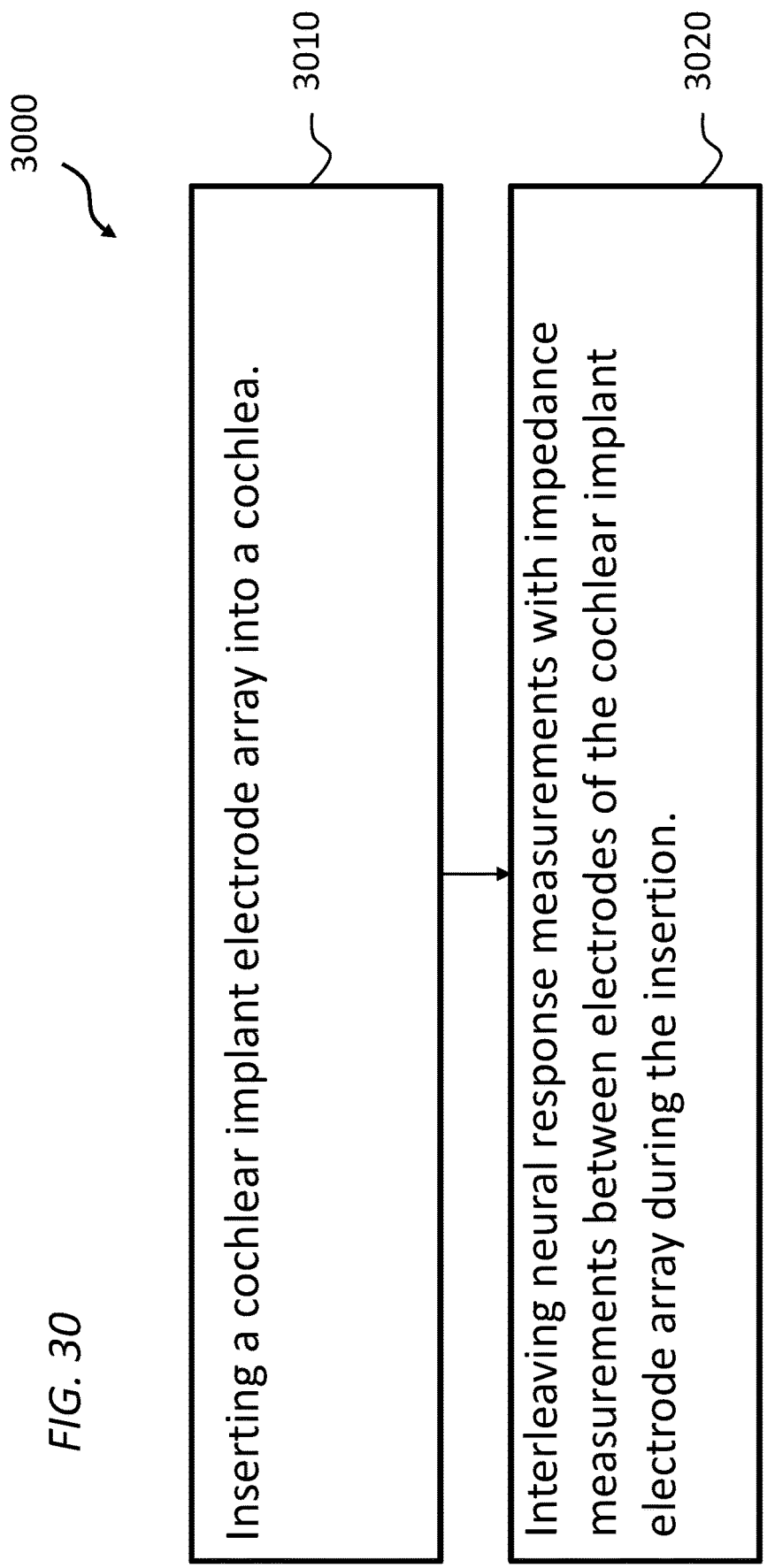

FIG. 30 presents an exemplary algorithm for another exemplary method, method 3000, which includes method action 3010, which includes the action of inserting a cochlear implant electrode array into a cochlea (the actual movement of the array), and method action 3020, which includes the action of interleaving neural response measurements with impedance measurements between electrodes of the cochlear implant electrode array during the insertion. In an exemplary embodiment, the neural response measurements are one or both of NRT (Neural Response Telemetry) or ECoG and/or the impedance measurements are four point impedance measurements.

In an exemplary embodiment of method 3000, the impedance measurements between electrodes of the cochlear implant electrode array are limited to those associated with electrodes proximate the basal turn of the cochlea during insertion, or are otherwise limited as detailed above. In an exemplary embodiment, the impedance measurements between electrodes of the cochlear implant electrode array are limited to those associated with electrodes proximate no more than three different locations within the cochlea during insertion or are limited as detailed above.

Figure 31:
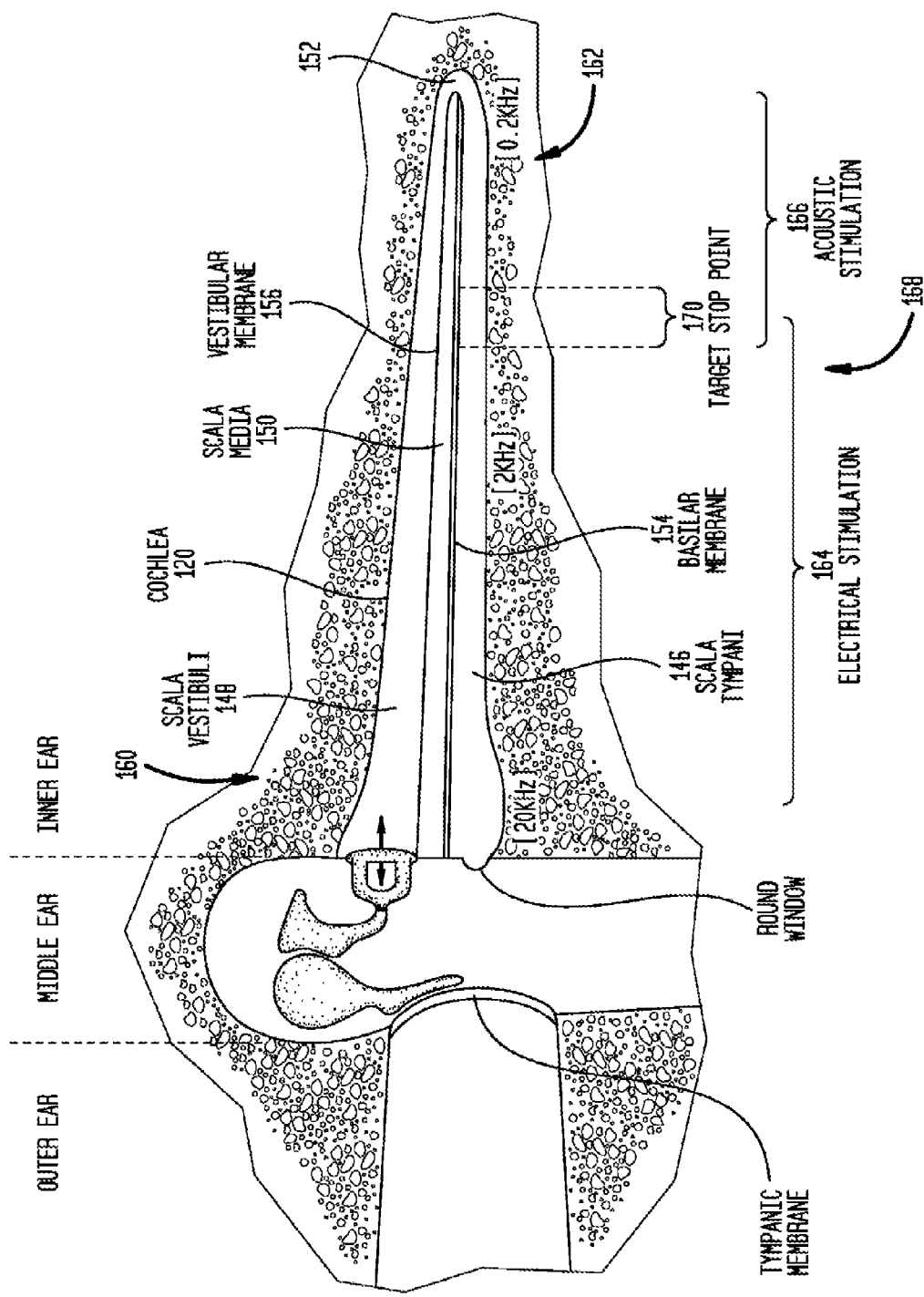
FIG. 31 presents an exemplary schematic useful for explaining an embodiment.
Figure 32:
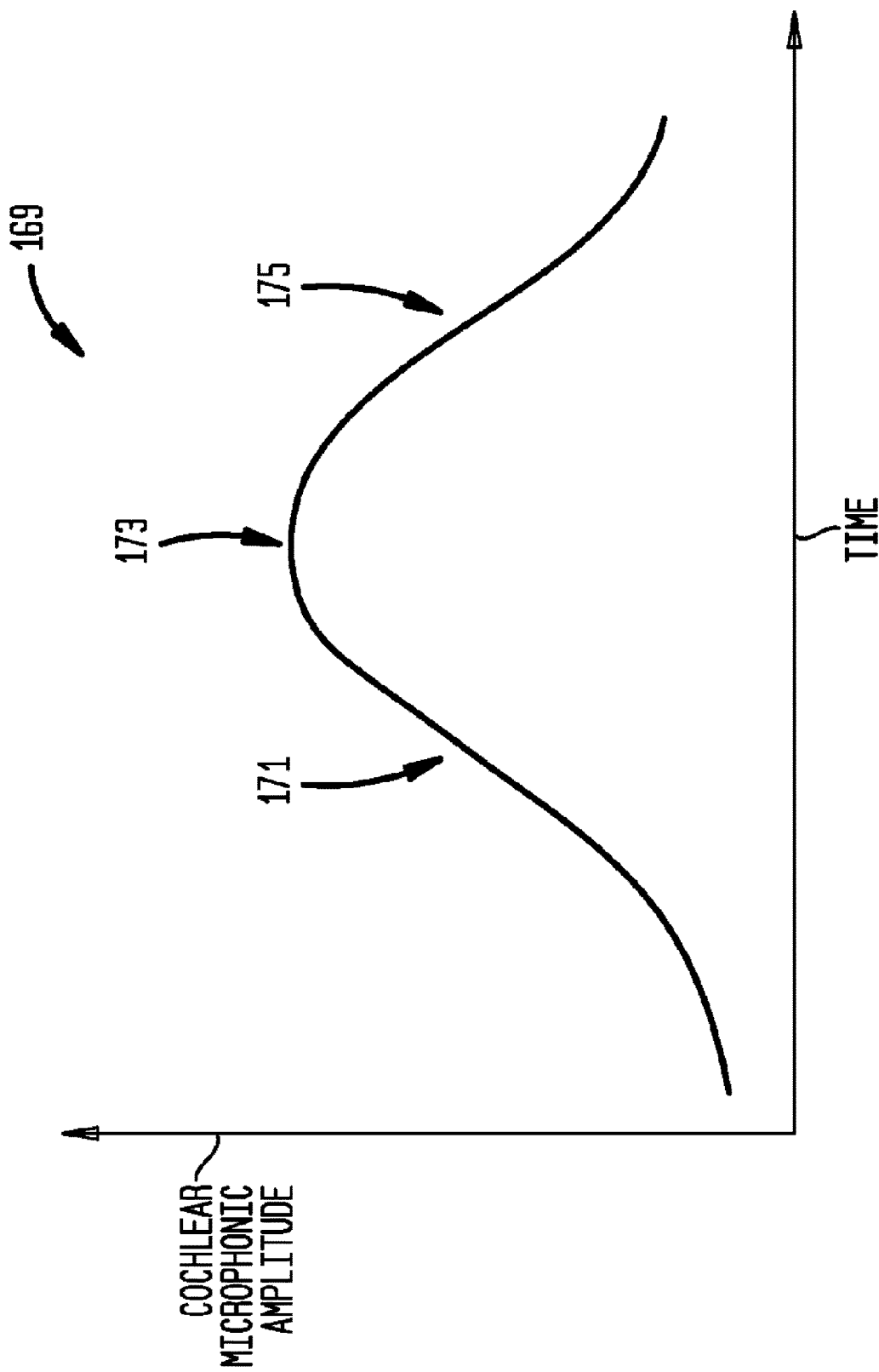
FIG. 32 presents exemplary data according to some embodiments.

As noted above, the teachings detailed herein can be combined with neural response measurements. In this regard, a recipient's cochlea 120 is a conical spiral structure comprising three parallel fluid-filled canals or ducts, collectively and generally referred to herein as canals. For ease of illustration, and all the following reference numbers refer to those of FIGS. 31, 32, and 33, and thus cannot be confused with reference numbers from FIGS. 1A to 30, FIG. 31 illustrates cochlea 120 in an "unrolled" arrangement. The cochlea canals comprise the tympanic canal 146, also referred to as the scala tympani, the vestibular canal 148, also referred to as the scala vestibuli, and the median canal 150, also referred to as the scala media. Cochlea 140 spirals about a recipient's modiolus (not shown) several times and terminates at cochlea apex 152. Separating the cochlea canals are various membranes and other tissue. In particular, toward a lateral side of the scala tympani 146, a basilar membrane 154 separates the scala tympani 146 from the scala media 150. Similarly, toward lateral side of the scala vestibuli 148, a vestibular membrane 156, also referred to as the Reissner's membrane, separates the scala vestibuli 148 from the scala media 150. The scala tympani 146 and the scala vestibuli 148 are filled with a fluid, referred to herein as perilymph, which has different properties than that of the fluid which fills the scala media 148, referred to as endolymph, and which surrounds the organ of Corti (not shown). Sound entering the auricle of a recipient's ear causes pressure changes in cochlea 120 to travel through the fluid-filled tympanic and vestibular canals 146, 148. The organ of Corti, which is situated on basilar membrane 154 in scala tympani 146, contains rows of 16,000-20,000 hair cells (not shown) which protrude from its surface. Above them is the tectorial membrane which moves in response to pressure variations in the fluid-filled tympanic and vestibular canals 146, 148. Small relative movements of the layers of the tectorial membrane are sufficient to cause the hair cells in the endolymph to move thereby causing the creation of a voltage pulse or action potential which travels along the associated nerve fiber to the auditory areas of the brain for processing. The place along basilar membrane 154 where maximum excitation of the hair cells occurs determines the perception of pitch and loudness according to the place theory. Due to this anatomical arrangement, cochlea 120 has characteristically been referred to as being "tonotopically mapped." That is, regions of cochlea 120 toward basal region 160 are responsive to higher frequency signals, while regions of cochlea 120 toward apical region 162 are responsive to lower frequency signals. For example, the proximal end of the basal region 160 is generally responsible to 20 kilohertz (kHz) sounds, while the distal end of the apical region is responsive to sounds at around 200 hertz (Hz). In hearing prosthesis recipients, residual hearing most often is present within the lower frequency ranges (i.e., the more apical regions of the cochlea) and little or no residual hearing is present in the higher frequency ranges (i.e., the more basal regions of the cochlea). This property of residual hearing is exploited in electro-acoustic hearing prostheses where the stimulating assembly is inserted into the basal region and is used to deliver electrical stimulation signals to evoke perception of higher frequency sounds. Ideally, insertion of the stimulating assembly is terminated before reaching the functioning regions of the cochlea where there is residual hearing so that remaining hair cells are able to naturally perceive lower frequency sounds that cause movement of the perilymph. This concept is illustrated in FIG. 31 where reference 164 illustrates the region of the cochlea 120 to which electrical stimulation is delivered to evoke hearing perception, while reference 166 illustrates the region of the cochlea 120 that utilizes acoustic stimulation to evoke a hearing perception. The tonotopic region of the cochlea 120 where the sound or stimulation output transitions from the acoustic stimulation to the electric stimulation is called the cross-over frequency region, and is illustrated in FIG. 31 by reference 168. Recipients of electro-acoustic hearing prosthesis may have different residual hearing characteristics and, accordingly, different cross-over frequency regions (i.e., transitions occur at different tonotopic regions of the cochlea). Additionally, insertion of the distal end of a stimulating assembly into and/or past the cross-over frequency region can interfere with, or damage, the recipient's residual hearing. Therefore, as noted above, an objective of the techniques presented herein is to provide a surgeon with objective measurements that enable insertion of a stimulating assembly to be halted at a depth, referred to elsewhere herein as the target stop point, that does not interfere with or damage the recipient's residual hearing. The target stop point, which is defined as a specific frequency or a specific frequency range (pre-operatively defined insertion stop frequency), is represented in FIG. 31 by reference 170. Also as noted elsewhere herein, a target stop condition occurs when the distal end or other portion of a stimulating assembly is inserted to a location (depth) within the cochlea that corresponds to (i.e., at or near) the pre-operatively defined insertion stop frequency (i.e., the specific frequency or a specific frequency range of the target stop point). As noted above, the intra-operative system 105 may utilize any of a number of different types of inner ear potential measurements to determine when the stimulating assembly 126 has encountered an insertion stop or warning condition. FIG. 32 is a graph 169 illustrating how inner ear responses in the form of cochlear microphonic amplitudes can be used to determine when a measurement contact approaches, reaches, and passes a tonotopic region of the cochlea associated with a target stop point. The graph 169 of FIG. 32 has a vertical axis that represents the amplitude of a measured cochlear microphonic amplitudes and a horizontal axis that represents time. In the example of FIG. 32, the cochlea 120 of the recipient is stimulated with an acoustic input having at least one selected frequency that is associated with (i.e., corresponds to) a specific tonotopic region of the cochlea 120. As the stimulating assembly 126 is inserted into the cochlea 120, at least one contact of the stimulating assembly 126 (i.e., the measurement contact) is used to obtain ECoG measurements, which include the cochlear microphonic amplitude. As shown by reference 171 in FIG. 32, the amplitude of the cochlear microphonic gradually increases as the measurement contact approaches the tonotopic region of the cochlea associated with the frequency of the acoustic input. As shown by reference 173, the amplitude of the cochlear microphonic peaks when the measurement contact is located at the tonotopic region of the cochlea associated with the frequency of the acoustic input. Finally, as shown by reference 175, the amplitude of the cochlear microphonic gradually decreases as the measurement contact moves away from the tonotopic region of the cochlea associated with the frequency of the acoustic input.

As noted above, an objective of the insertion process is to stop insertion of the stimulating assembly 126 when a portion of the stimulating assembly (e.g., a distal end of the stimulating assembly and/or one or more stimulating contacts) reaches, but does not pass, a tonotopic region corresponding to the pre-operatively defined insertion stop frequency (i.e., the target stop point). Therefore, FIG. 32 is merely illustrative and does not represent cochlear microphonic amplitudes that would be measured in all embodiments. Instead, when the cochlear microphonic amplitude is measured at the pre-operatively defined insertion stop frequency, the insertion could stop at points 171 or, ideally, 173 of FIG. 32 (i.e., before the measurement contact passes the target stop point). In addition to a target stop condition, embodiments presented herein are also configured to monitor insertion of a stimulating assembly for warning conditions or an error stop condition. An error stop condition occurs when a stimulating assembly physically contacts or otherwise interferes with the organ of corti (including the basilar membrane 154) at any point along the stimulating assembly. Contact or interference may be due to, for example, over insertion, cochlea morphology, improper surgical trajectory, etc. Further details for detection of target stop conditions, an error stop conditions, and warning conditions are provided below.

Figure 33:
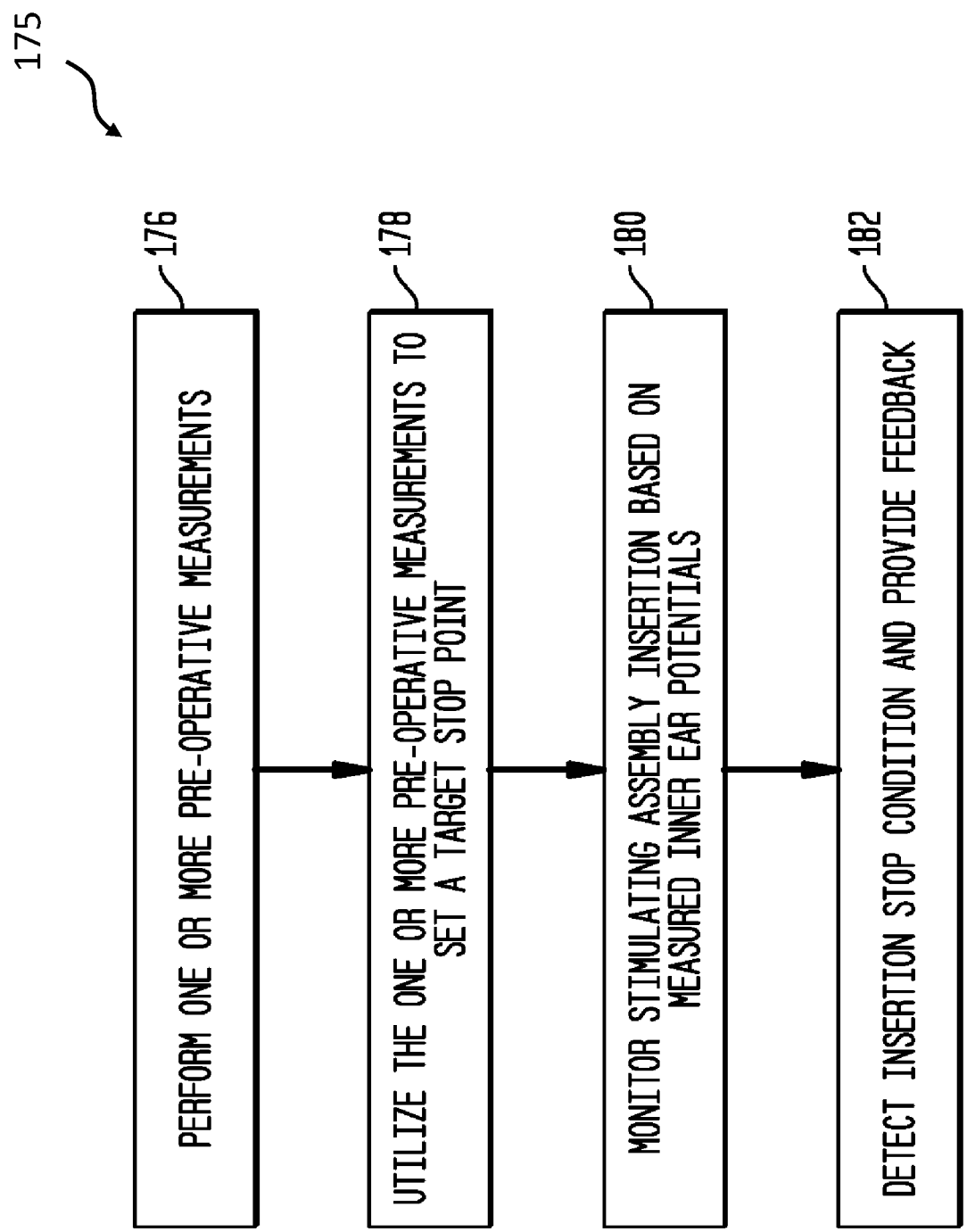
FIG. 33 presents an exemplary algorithm for an exemplary method.

FIG. 33 is a flowchart illustrating operations associated with detection of one or more stop conditions in accordance with embodiments presented herein. For ease of illustration, the method of FIG. 33 is described with reference to an intra-operative system and a hearing prosthesis descried above. The method 175 of FIG. 3 begins at 176 where one or more pre-operative tests/measurements are performed on the recipient to assess the function of cochlea 120 (i.e., the cochlea in which the stimulating assembly 126 is to be implanted). The one or more pre-operative tests can include an audiogram measurement of the recipient's cochlea 120 in order to record the recipient's residual hearing (i.e., to determine the frequency and/frequency range where the recipient's residual hearing begins). An audiogram measurement refers to a behavioral hearing test, sometimes referred to as audiometry, which generates an audiogram. The behavioral test involves the delivery of different tones, presented at a specific frequency (pitch) and intensity (loudness), to the recipient's cochlea and the recording of the recipient's subjective responses. The resulting audiogram is a graph that illustrates the audible threshold for standardized frequencies as measured by an audiometer. In general, audiograms are set out with frequency in Hertz (Hz) on the horizontal (X) axis, most commonly on a logarithmic scale, and a linear decibels Hearing Level (dBHL) scale on the vertical (Y) axis. In certain arrangements, the recipient's threshold of hearing is plotted relative to a standardized curve that represents 'normal' hearing, in dBHL. The audiogram is used to determine the frequency and threshold of hearing for the recipient's cochlea. In addition to an audiogram measurement, the pre-operative tests can also include one or more imaging tests, such as a high resolution computed tomography (CT) scan, X-ray, Magnetic resonance imaging (MRI), etc. of the recipient's cochlea. In certain embodiments, the high resolution CT scan, and possibly the MRI, is employed clinically to determine if there are anatomical abnormities or bone growth (meningitis) prior to the surgery. The MRI can also be used to determine the viability of the auditory nerve. Moreover, the size of the cochlea may be assessed (estimated) via high resolution CT scans that measure the anatomical landmarks, which can be used to assist with the prediction of insertion depth angle.

The one or more pre-operative tests can also include an initial inner potential measurement, such as an ECoG measurement, that is performed from outside of the cochlea (e.g., the round window). The inner potential measurements can be taken pre-operatively, using a measurement electrode that is inserted through the tympanic membrane, or intra-operatively before beginning insertion of the stimulating assembly 126 (i.e., before drilling the cochleostomy or making the incision in the round window). In the case of an ECoG measurement, ECoG responses are evoked using an acoustic input at a number of different frequencies and a fixed presentation level (e.g., supra-threshold). As such, a pre-operative ECoG measurement provides a baseline recording of the ECoG responses at each of a number of different frequencies along the length of the cochlea 120, along with the relative magnitude information between each frequency to indicate a region where maximum ECoG amplitude can be expected for each frequency.

At 178, the results of the pre-operative measurements (e.g., audiogram, CT scan, initial inner potential measurement, etc.) are used to set a target stop point for the stimulating assembly 126. As noted above, a target stop point is a cochlea frequency or frequency range, sometimes referred to herein as a pre-operatively defined insertion stop frequency, to which a distal end 133 of the stimulating assembly 126 is expected to be inserted so as to be located at or near the tonotopic region where the recipient's residual hearing begins. In certain embodiments, the target stop point is set at a conservative frequency or frequency range that would minimize the probability of causing either unrecoverable or permanent damage to the residual hearing. As such, the target stop depth is a type of predictive estimate or target that, as described below, is monitored and possibly refined during the insertion process.

In certain embodiments, normative statistics generated based on prior implantations for similar recipients can be used to further refine the target stop point (i.e., revise the target stop depth based on information determined from other recipients having similar characteristics/attributes to the subject recipient). For example, the refinement based on normative statistics can be made by taking into account the recipient's age (i.e., refine based on implantation results from similarly aged recipients), the one or more imaging tests (e.g., based on implantation results for recipient's having similar X-rays, CT scans, etc.), hearing loss, etiology or other shared characteristics.

In addition to the target stop point, the results of the pre-operative measurements can also be used to set a minimum insertion depth. The minimum insertion depth defines the depth to which the distal end 133 of the stimulating assembly 126 is estimated to be implanted in the cochlea in order to provide acceptable electrical only hearing performance (e.g., based on existing clinical evidence). This minimum insertion depth would take into account anatomical differences (e.g., smaller cochlea sizes, malformations, etc.) identified by the pre-operative measurements. In general, the minimum insertion depth could be specified as a frequency, frequency range, or an angle. Defining the minimum insertion depth as an angle takes into account the variations in the cochlea anatomical size and the electrode type (modiolar or lateral wall), etc.

In general, it has been determined that for electrical-only hearing (i.e., only electrical stimulation) with a full length array, there is a minimum insertion depth where maximum clinical benefit can be obtained. Any insertion depth that is under this is distance, again for electrical-only hearing, will have a poor clinical outcome. It is also expected that, for some recipients, residual acoustic hearing will eventually reduce, leaving only the electrical hearing abilities. For recipient's likely willing to undergo revision surgery (e.g., children), the minimum insertion depth may be an insertion depth where it is ensured that the acoustic hearing is fully unperturbed by the introduction of the stimulating assembly. For recipient's unlikely to undergo an additional surgery (e.g., older recipients), the minimum insertion depth may be a depth where it is determined that, when the residual acoustic hearing deteriorates, the implanted stimulating assembly will still provide acceptable electrical-only performance.

After setting the target stop point and the minimum insertion depth, the surgeon begins implantation of the stimulating assembly (e.g. opens the cochleostomy or incises the round window and inserts the distal end into the cochlea). At 180, the insertion of the stimulating assembly 126 is monitored using objective inner ear potentials measured, in real-time, via one or more stimulating contacts 138. For example, in certain embodiments one or more acoustic tones (e.g., pure tone(s)) at a selected frequency or frequencies are delivered to the recipient's outer ear using, for example, the receiver 142. The acoustic signals delivered by the receiver 142 cause displacement waveforms that travel along the basilar membrane. These waves grow in amplitude and reach a maximum at the characteristics frequency (CF) as a function of frequency along the cochlea. These vibrations along the cochlea give rise to an inner ear potential. Therefore, in response to the delivered acoustic signals, one or more of the stimulating contacts 128 and the integrated amplifier(s) 143 of the cochlear implant capture one or more windows of the evoked activity (i.e., perform ECoG measurements) to generate inner ear response measurements (e.g., ECoG response measurements) that are provided to the intra-operative system 105. In other words, the intra-operative system 105 monitors the inner ear response at one or more of the stimulating contacts 138.

In certain examples, the acoustic signals delivered by the receiver 142 are selected based on the results of the one or more pre-operative tests. For example, the acoustic signals can have a frequency that is the same as, or close to, the frequency of the target stop point (e.g., at a frequency where the augmented hearing (electrical and acoustic) offers the maximal clinical benefit, around a predetermined cutoff frequency where acoustic hearing starts, etc.,) determined from the pre-operative audiogram. At 182, an insertion stop condition is detected and, in response to the detection, a feedback mechanism is initiated/triggered. As noted above, an insertion stop condition can include a target stop condition, meaning that the intra-operative system 105 has determined that a selection portion of the stimulating assembly 126 (e.g., distal end 133, one or more contacts 138, etc.) has reached the tonotopic region corresponding to the frequency defining the target stop point. If the target stop condition is detected, insertion of the stimulating assembly 126 should be terminated to prevent damage to the recipient's residual hearing.

Also as noted above, an insertion stop condition can also be an error stop condition, meaning that the stimulating assembly 126 has interfered with (e.g., come into physical contact with) an intra-cochlea structure, such as the basilar membrane. For example, it is possible that the stimulating assembly can move outwards towards the scala wall, at points other than the apical region of the stimulating assemble (e.g., a modiolar hugging array, which is flexible, can reach a point in the insertion when it meets physical resistance and bows outwards to the scala wall, riding up the wall to eventually make physical contact with the basilar membrane). If an error stop condition is detected, corrective action should be initiated.

In accordance with the embodiments presented herein, the insertion stop or warning conditions can be detected in a number of different manners. More specifically, referring first to the detection of a target stop condition, one or more objective inner ear potential measurements, such as ECoG measurements, are continually performed in real-time while the stimulating assembly 126 is inserted into the cochlea 120 (i.e., as the stimulating assembly 126 is moved in an apical direction). The intra-operative system 105 analyzes the measured real-time inner ear potentials relative to one another to determine if a change in the measured response occurs. The change may be, for example, an expected change in the magnitude/amplitude, phase, shape of the response/waveform (morphology), frequency, or other aspects of the responses. For example, in one embodiment, an expected change indicative of a target stop condition comprises the detection of a peak or near peak in acoustically-evoked inner ear potentials (e.g., CM components of ECoG responses).

Again, in accordance with embodiments presented herein, the real-time inner ear potential measurements can be made in a number of different manners at one or more locations (e.g., simultaneously, sequentially, etc.) within the cochlea. In certain embodiments, inner ear potential measurements can be used to monitor or track the progression of the stimulating assembly 126 within the cochlea 120 using one or more complex acoustic inputs (sound signals) comprising multiple frequencies. In other words, inner ear potential measurements can be performed based on several different acoustic frequencies and/or at different contacts of the stimulating assembly (i.e., multi-frequency acoustic inputs and/or multi-electrode/contact recording). The complex acoustic inputs may comprise, for example, a frequency sweep signal, a series of sound chirps, etc. More specifically, the intra-operative system 105 can be configured to perform inner ear potential measurements at any of a number of contacts (in response to the same or different acoustic input), and then perform a comparison relative to another and/or against previous time points (e.g., pattern matching, correlation, etc.). Signal features that can be compared at, for example, different time points (cross-time point comparison) include phase, amplitude, morphology, etc. Based on the comparisons, the intra-operative system 105 could determine, for example, current insertion depth, location relative to the predicted depth, basilar membrane contact, stimulating assembly deformation (e.g., bowing), tonotopic mapping in the cochlea, changes to the acoustic resonant properties of the cochlea, etc.

In summary, the inner ear potential measurements in accordance with embodiments presented herein may make use of multi-electrode recording, complex acoustic inputs, cross-time comparisons, and/or cross-electrode comparisons. These variations could, for example, enable the system to gauge the current tonotopic position of the measurement contact(s) (e.g., apical electrode) and/or to set a baseline that makes early stage detection of a "shift" in the cochlea microphonic (such as a change in resonant frequency) easier to detect.

In certain embodiments, one or more complex acoustic inputs (e.g., a frequency sweep signal or a series of sound chirps) are used to correlate the position of one or more contacts with a frequency response as the array advances within the cochlea. That is, the one or more complex acoustic inputs enable the intra-operative system 105 to detect the current tonotopic position of one or more contacts and, accordingly, the position of the stimulating assembly 126. In one such example, one or more complex acoustic inputs are delivered to the cochlea 120 to evoke responses along the cochlea at tonotopic locations preceding the target frequency (i.e., frequencies that are higher than the target stop point). Using these responses, the intra-operative system 105 can then determine when the measurement contacts (e.g., the apical contact) approaches, reaches, and passes the tonotopic region of the cochlea associated with each of the frequencies. As noted above, FIG. 32 illustrates an example of a cochlear microphonic amplitude measured as a measurement contact approaches, reaches, and passes the tonotopic region of the cochlea 120 that corresponds to the frequency of an acoustic input.

In an exemplary embodiment, method 3000 includes the action of interleaving any one or more of the actions just detailed above, such as those detailed with respect to FIGS. 31, 32, and/or 33, with any one or more of the impedance measurement techniques detailed herein. As noted above, some embodiments include interleaving neural response measurements with the aforementioned impedance measurements, and such can utilize any of the neural response actions just detailed. In an exemplary embodiment, the impedance measurements are taken in an alternating manner with the neural response measurements. In an exemplary embodiment, an exemplary method can include first taking neural response measurements, then taking impedance measurements, then taking neural response measurements, then taking impedance measurements, then taking neural response measurements, then taking impedance measurements, and so on, where this cycle (neural response measurement followed by impedance measurements or vice versa) is executed at the least every second or every 2 seconds or 3 seconds or 4 or 5 or 6 or 7 or 8 or 9 or 10 seconds during the insertion of the electrode array, or every time a new electrode is inserted into the cochlea, or based on some other indicator, etc. It is also noted that in some exemplary embodiments, the cycle can vary such that there can be one or two or three or more impedance actions in between every neural response measurement action or vice versa.

Thus, method 3000 can include the action of, during insertion of a stimulating assembly into a cochlea of a recipient, monitoring, at an intra-operative system, acoustically-evoked inner ear potentials (and/or neural response based on stimulation of the nerves with the cochlear implant electrode array—NRT) obtained from the cochlea of the recipient while also monitoring, at the intra-operative system, impedance measurements obtained from within the cochlea. In an exemplary embodiment, to reduce the time utilized by the impedance measurements (ECoG and NRT can take longer to achieve utilitarian information and then that required to obtain utilitarian information from impedance measurements), the impedance measurements can be focused at areas of importance, such as the basal turn, in accordance with the teachings detailed above, while other locations are ignored or otherwise relegated to secondary status (e.g., the amount of time that impedance measurements are taken at some locations is much lower than the amount of time that impedance measurements are taken at other locations).

In an exemplary embodiment, method 300 further includes the action of, at the intra-operative system, detecting, based on the acoustically-evoked inner ear potentials (and/or NRT), an insertion stop condition, and responsive to detection of an insertion stop condition, initiating, at the intra-operative system, a feedback mechanism to stop insertion of the stimulating assembly into the cochlea, and/or, detecting based on the impedance measurements, an insertion stop condition, and responsive to detection of an insertion stop condition, initiating, at the intra-operative system, a feedback mechanism to stop insertion of the stimulating assembly into the cochlea.

An exemplary embodiment of this method can include initiating a feedback mechanism to stop insertion of the stimulating assembly comprises at least one of: stopping automated insertion of the stimulating assembly, or generating a stop notification for a surgeon to stop insertion of the stimulating assembly, and/or at the intra-operative system, detecting, based on the acoustically-evoked inner ear potentials, an insertion warning condition and responsive to detection of an insertion warning condition, initiating a feedback mechanism to slow insertion of the stimulating assembly into the cochlea. Further, an exemplary method can include detecting an insertion stop condition by detecting an error stop condition comprising a change in the acoustically-evoked inner ear potentials indicative of a mechanical impedance change of the basilar membrane, and wherein the method further comprises initiating a feedback mechanism indicating that the stimulating assembly has interfered with a basilar membrane of the cochlea. In an exemplary embodiment, the action of detecting an insertion stop condition comprises detecting a target stop condition comprising a relative change in the acoustically-evoked inner ear potentials, indicating that one or more stimulating contacts of the stimulating assembly are located at a tonotopic position corresponding to a pre-operatively defined insertion stop frequency, and wherein the method further comprises initiating a feedback mechanism indicating that the stimulating assembly has been inserted to a target insertion depth. In an exemplary embodiment, the action of detecting a target stop condition comprises detecting a peak or near peak in an attribute of the acoustically-evoked inner ear potentials associated with the insertion stop frequency.

It is noted that in an exemplary embodiment includes a method of inserting an electrode array into a cochlea and while the electrode array is being pushed into the cochlea, a tone or sound or otherwise acoustic stimulation is applied as part of an ECoG method. This sound can be continuous or semicontinuous during the insertion process. In an exemplary embodiment, the sound is used to stimulate the tissue and evoke the neural response for the amount of time that is at least 10, 15, 20, 25, 30, 35, 40, 45, 50, 55, 60, 65, 70, 75, 80, 85, 90, 95 or 100% of the time between the first electrode entering the cochlea until the last electrode enters the cochlea and/or the electrode array is fully inserted into the cochlea/until the electrode array reaches a location that corresponds to the furthest the electrode array is ever inserted into the cochlea. In an exemplary embodiment, the impedance measurements are taken while the aforementioned sound is stimulating the tissue/evoking the neural responses. In an exemplary embodiment, the ECoG measurements are taken while the aforementioned sound the stimulating the tissue/evoking mineral responses. Again, in an exemplary embodiment, the method of inserting the electrode array into the cochlea is executed while the sound is being played and otherwise evoking the neural responses, and during this time, the electrodes are being used to take the impedance measurements and/or the ECoG measurements. Accordingly, in an exemplary embodiment, there is a method that includes executing a portion of an ECoG method in general, and specifically, executing the acoustic stimulus to evoke the neural response, and while this neural response is occurring, taking the impedance measurements to execute one or more or all of the actions associated with the impedance measurements detailed herein.

In view of the above, an exemplary embodiment includes a method where, while the sound is applied, the ECOG measurements are interleaved with the impedance measurements.

Note also that while in some embodiments, the sound is constantly played, in other embodiments, the sound is played for only those portions of the insertion where it is more likely than not that the ECOG measurements will be utilitarian. For example, the sound could be begun to be played at a location somewhere before the do not exceed location such that there is very little likelihood that the electrode array will reach that location while the sound is not played. This will results, in some embodiments, to the sound being played during times where the ECOG measurements are not needed or otherwise less valuable than at other areas.

In an exemplary embodiment, the methods herein and the systems herein are such that the electrodes that are energized for the impedance measurements are not used as measurement electrodes for the ECOG measurements. In an exemplary embodiment, an exemplary method includes executing both ECOG measurements and impedance measurements during insertion, where the most distal electrode is not used as a source or sink. In an exemplary embodiment, an exemplary method includes executing both ECOG measurements and impedance measurements during insertion of the electrode array, where the second and or third and/or fourth most distal electrodes are never utilized as a source and/or a sink electrode. In an exemplary embodiment of this embodiment, the most distal electrode is used as a source and/or a sink.

An exemplary embodiment includes utilizing electrodes that are utilized as a source and/or a sink during impedance measurements as measurement electrodes for the ECOG measurements, except that the time period between the utilization of such as a source and/or a sink and the utilization as a measurement electrode is such that any polarization or otherwise charge buildup is reduced relative to that which would be the case if the electrodes were used as a source and a sink and a measurement electrode in a shorter time period.

Thus, in view of the above, there is a method that includes executing neural response measurements N times, where N equals 1, 2, 3, 4, 5, 6, 7, 8, 9, or 10 or more, followed by the execution of impedance measurements P times, where P equals 1, 2, 3, 4, 5, 6, 7, 8, 9, or 10 or more, followed by the execution of neural response measurements Q times, where Q equals 1, 2, 3, 4, 5, 6, 7, 8, 9, or 10 followed by the execution of impedance measurements T times, where T equals 1, 2, 3, 4, 5, 6, 7, 8, 9 or 10 followed by the execution of neural response measurements U times, where U equals 1, 2, 3, 4, 5, 6, 7, 8, 9, or 10 followed by the execution of impedance measurements V times, where V equals 1, 2, 3, 4, 5, 6, 7, 8, 9, or 10 followed by the execution of neural response measurements R times, where R equals 1, 2, 3, 4, 5, 6, 7, 8, 9, or 10 followed by the execution of impedance measurements S times, where S equals 1, 2, 3, 4, 5, 6, 7, 8, 9, or 10 followed by the execution of neural response measurements W times, where W equals 1, 2, 3, 4, 5, 6, 7, 8, 9, or 10 followed by the execution of impedance measurements F times, where F equals 1, 2, 3, 4, 5, 6, 7, 8, 9, or 10, wherein the first measurement of the action of interleaving can be an impedance measurement or a neural response measurement.

Further, in view of the above, there is a method that includes executing neural response measurements any number of times equal to an integer between 1 and 100 followed by executing impedance measurements any number of times equal to an integer between 1 and 100, and repeating this process in full or in part an integer number of times equal to 1 and 100.

In an exemplary embodiment, there is a method detailed above, wherein the action of interleaving comprises executing one or more complete neural response measurements followed by the execution of focused impedance measurements followed by the execution of one or more complete neural response measurements followed by the execution of focused impedance measurements followed by the execution of one or more complete neural response measurements followed by the execution of focused impedance measurements followed by the execution of one or more complete neural response measurements followed by the execution of focused impedance measurements. In an exemplary embodiment, there is a method detailed above, wherein the action of interleaving comprises executing one or more complete neural response measurements followed by the execution of focused impedance measurements, wherein this is repeated, in whole or in part, any number of times equal to an integer between 1 and 100.

Any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, unless such is otherwise noted.

Any disclosure herein of a method of making a device herein corresponds to a disclosure of the resulting device. Any disclosure herein of a device corresponds to a disclosure of making such a device.

Any one or more elements or features disclosed herein can be specifically excluded from use with one or more or all of the other features disclosed herein.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
    energizing one or more electrodes of a cochlear electrode array to induce a current flow in the cochlea at a plurality of temporal locations;
    measuring one or more electrical properties at one or more locations in the cochlea resulting from the induced current flow at the plurality of different temporal locations;
    determining whether or not trauma has occurred based on a change between the measured one or more electrical properties from a first temporal location to a second temporal location of the plurality of different temporal locations; and
    at least one of:
        a. analyzing the change in the measured one or more electrical properties to identify indications of blood in the cochlea and upon a determination that an indication that blood in the cochlea is present, determining that trauma has occurred; or
        b. analyzing the change in the measured one or more electrical properties to identify indications of a clot in the cochlea and upon a determination that an indication that a clot in the cochlea is present, determining that trauma has occurred.

2. The method of claim 1, comprising:
    analyzing the change in the measured one or more electrical properties to identify indications of blood in the cochlea; and
    upon a determination that an indication that blood in the cochlea is present, determining that trauma has occurred.

3. The method of claim 1, comprising:
    analyzing the change in the measured one or more electrical properties to identify indications of a clot in the cochlea; and
    upon a determination that an indication that a clot in the cochlea is present, determining that trauma has occurred.

4. The method of claim 1, further comprising:
    evaluating a time period between the first temporal location and the second temporal location of the plurality of different temporal locations; and
    based on the evaluation of the time period, determining that trauma has occurred.

5. The method of claim 1, further comprising:
    evaluating a time period between the first temporal location and the second temporal location of the plurality of different temporal locations; and
    based on the evaluation of the time period, determining that trauma has not occurred.

6. The method of claim 1, further comprising:
    determining that trauma has occurred; and
    executing source localization techniques to identify an anatomical location of the trauma within the cochlea.

7. A method, comprising:
    energizing one or more electrodes of a cochlear electrode array to induce a current flow in the cochlea at a plurality of temporal locations;
    measuring one or more electrical properties at one or more locations in the cochlea resulting from the induced current flow at the plurality of different temporal locations;
    determining whether or not trauma has occurred based on a change between the measured one or more electrical properties from a first temporal location to a second temporal location of the plurality of different temporal locations;
    analyzing the change in the measured one or more electrical properties to identify indications of blood in the cochlea; and
    upon a determination that an indication that blood in the cochlea is not present, determining that trauma has not occurred.

8. A method, comprising:
    causing current to flow from a first electrode of an intra-cochlea electrode array to a second electrode of the intra-cochlea electrode array at a plurality of temporal locations;
    measuring, at a third electrode and a fourth electrode of the intra-cochlea electrode array, respective voltages induced by the flowing current at the plurality of temporal locations;
    determining that a change between the voltage measurements at the third electrode and the fourth electrode has occurred between the temporal locations;
    determining a time period between the temporal locations; and
    determining whether or not a phenomenon has occurred within the cochlea based on the determined time period.

9. The method of claim 8, wherein:
    the phenomenon is blood entry into the cochlea.

10. The method of claim 8, wherein:
    the phenomenon is trauma to the cochlea due to electrode array insertion.

11. The method of claim 8, wherein:
    the determined time period is a period between about 1 and about 4 minutes, and the method further includes determining that the phenomenon has occurred based on that time period.

12. The method of claim 8, wherein:
the change in voltage measurements results from an increase in impedance between the electrodes; and
the determined time period is a period between about 1 and about 4 minutes, and the method further includes determining that the phenomenon has occurred based on that time period.

13. The method of claim 8, wherein:
the determined time period is longer than 7 minutes, and the method further includes determining that the phenomenon has not occurred based on the determined time period.

14. The method of claim 8, wherein:
the determined time period is longer than 7 minutes, and the method further includes determining that the phenomenon has not occurred based on the determined time period; and
the phenomenon is blood entry into the cochlea.

15. The method of claim 8, wherein:
the determined time period is a period between about 1 and about 6 minutes.

16. The method of claim 8, wherein:
the determined time period is a period longer than a minute.

17. The method of claim 8, wherein:
the determined time period is a period longer than 10 minutes.

18. The method of claim 8, wherein:
the determined time period is a period between about 1 and about 6 minutes and the method further includes determining that the phenomenon has occurred based on that time period.

19. The method of claim 8, wherein:
the determined time period is a period longer than 3 minutes.

20. A method, comprising:
applying at first and second temporal locations respective electrical currents to one or more electrodes located in a cochlea of a recipient;
obtaining first and second data indicative of an electrical property at a location within the cochlea, the first and second data corresponding to data obtained, respectively, at the first and second temporal locations; and
evaluating whether or not there is an existence of a temporal change in the electrical property within the cochlea at the location based on the obtained data; and
determining whether or not there is blood and/or a clot in the cochlea based on the temporal change in the electrical property.

21. The method of claim 20, wherein:
the action of determining whether or not there is blood and/or a clot in the cochlea includes determining that there is blood in the cochlea; and
the method further includes determining a location of an origin of the blood in the cochlea.

22. The method of claim 20, wherein:
the action of determining whether or not there is blood and/or a clot in the cochlea includes determining that there is blood in the cochlea; and
the method further includes determining a location of an origin of the blood in the cochlea based on a comparison of the second data to at least third data indicative of electrical properties at a location away from the location, the third data being obtained at effectively the same time as the second data, wherein the second data is obtained after the first data.

23. The method of claim 20, wherein:
the action of applying at first and second temporal locations respective electrical currents to the one or more electrodes located in a cochlea of a recipient is executed using a cochlear implant electrode array four point impedance technique;
the temporal change is a change in impedance within the cochlea; and
the method further includes:
evaluating the change in the impedance relative to a time period, wherein
the action of determining whether or not there is blood and/or a clot in the cochlea includes differentiating between blood and the clot based on the evaluated change relative to the time period.

24. The method of claim 20, wherein:
the action of applying at first and second temporal locations respective electrical currents to the one or more electrodes located in a cochlea of a recipient is executed using a cochlear implant electrode array four point impedance technique;
the temporal change is a change in impedance within the cochlea; and
the method further includes:
evaluating the change in the impedance, wherein
the action of determining whether or not there is blood and/or a clot in the cochlea includes differentiating between blood and the clot based on the change in impedance.

* * * * *